United States Patent
Galindo et al.

(10) Patent No.: US 8,420,311 B2
(45) Date of Patent: Apr. 16, 2013

(54) METHOD TO BLOCK THE INFECTION BY FLAVIVIRUSES, MOLECULES AND USES

(75) Inventors: Vivian Huerta Galindo, Havana (CU); Glay Chinea Santiago, Havana (CU); Noralvis Fleitas Salazar, Havana (CU); Alejandro Miguel Martin Dunn, Havana (CU); Monica Sarria Nunez, Havana (CU); Osmany Guirola Cruz, Havana (CU); Patricia Gabriela Toledo Mayora, Havana (CU); Aniel Sanchez Puente, Havana (CU); Vladimir Armando Besada Perez, Havana (CU); Osvaldo Reyes Acosta, Havana (CU); Hilda Elisa Garay Perez, Havana (CU); Ania Cabrales Rico, Havana (CU); Alexis Musacchio Lasa, Havana (CU); Gabriel Ramon Padron Palomares, Havana (CU); Luis Javier Gonzalez Lopez, Havana (CU)

(73) Assignee: Centro de Ingenieria Genetica y Biotecnologia, Ciudad de La Habana (CU)

( * ) Notice: Subject to any disclaimer, the term of this patent is extended or adjusted under 35 U.S.C. 154(b) by 714 days.

(21) Appl. No.: 12/298,808

(22) PCT Filed: Apr. 26, 2007

(86) PCT No.: PCT/CU2007/000014
§ 371 (c)(1),
(2), (4) Date: May 12, 2009

(87) PCT Pub. No.: WO2007/124698
PCT Pub. Date: Nov. 8, 2007

(65) Prior Publication Data
US 2011/0212105 A1    Sep. 1, 2011

(30) Foreign Application Priority Data
Apr. 28, 2006    (CU) .................................. 2006-0091

(51) Int. Cl.
*C12Q 1/70*        (2006.01)
*A61K 39/12*       (2006.01)

(52) U.S. Cl.
USPC ............................................ 435/5; 424/218.1

(58) Field of Classification Search ........................ None
See application file for complete search history.

(56) References Cited

U.S. PATENT DOCUMENTS
2004/0242483 A1 * 12/2004 Lee et al. ......................... 514/12

FOREIGN PATENT DOCUMENTS
WO    WO2004016586 A2    2/2004
WO    WO 2005/056600 A2 *  6/2005

OTHER PUBLICATIONS

Deubel et al., Virology, 1986, 155:365-377.*
Cabrera-Henandez et al., "Mammalian Dengue Virus Receptors", Dengue Bulletin 2005 India, vol. 29, pp. 119-135 (2005).
Schlegel et al., "Amantadine and Dansyl Cadaverine Inhibit Vesicular Stomatitis Virus Uptake and Receptor Mediated Endocytosis of Alpha-2 Macro Globulin", Proceedings of the National Academy of Sciences of the United States of America, vol. 79, No. 7, pp. 2291-2295 (1982).
Koff et al., "Inhibition of Dengue Virus Replication by Amantadine Hydro Chloride", Antimicrobial Agents and Chemotherapy, American Society for Microbiology, Washington DC, vol. 18, No. 1, pp. 125-129 (1980).
Database Geneseq [online], "West Nile Virus Envelope Protein Ectodomain Peptide 39", XP002453298, retrieved from EBI accession No. GSP:AEF13619, p. 1, (2006).
Database Geneseq [online], "Den1 E Glycoprotein (373-398)", XP002453499, retrieved from EBI accession No. GSP: AAR25390, p. 1 (1992).
M. Simm, International Search Report for corresponding application PCT/CU2007/000014, p. 1-2, (2007).

* cited by examiner

*Primary Examiner* — Stacy B. Chen
(74) *Attorney, Agent, or Firm* — Hoffmann & Baron, LLP

(57) ABSTRACT

The present invention is related to a method for blocking the infection of cells by dengue virus, based on interfering the direct interaction of the viral envelope protein with a cellular receptor or its indirect interaction with said cellular receptor through a carrier protein, as well as related uses; wherein said cellular receptor is the alpha-2 macroglobulin receptor, also known as the low density receptor-related protein or as CD91, and said carrier protein is human alpha-2 macroglobulin.

8 Claims, 20 Drawing Sheets

A

Figure 1:
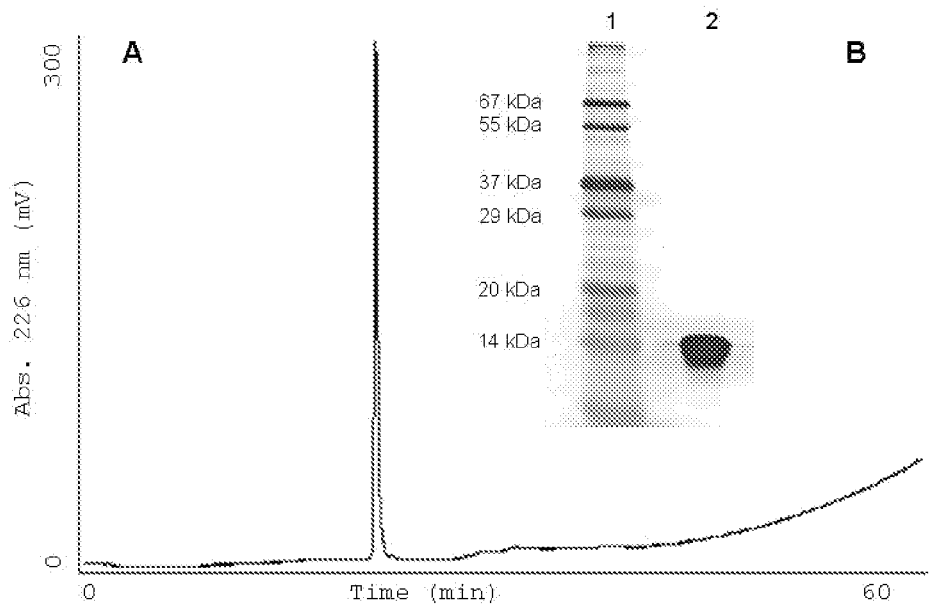
Figure 2:
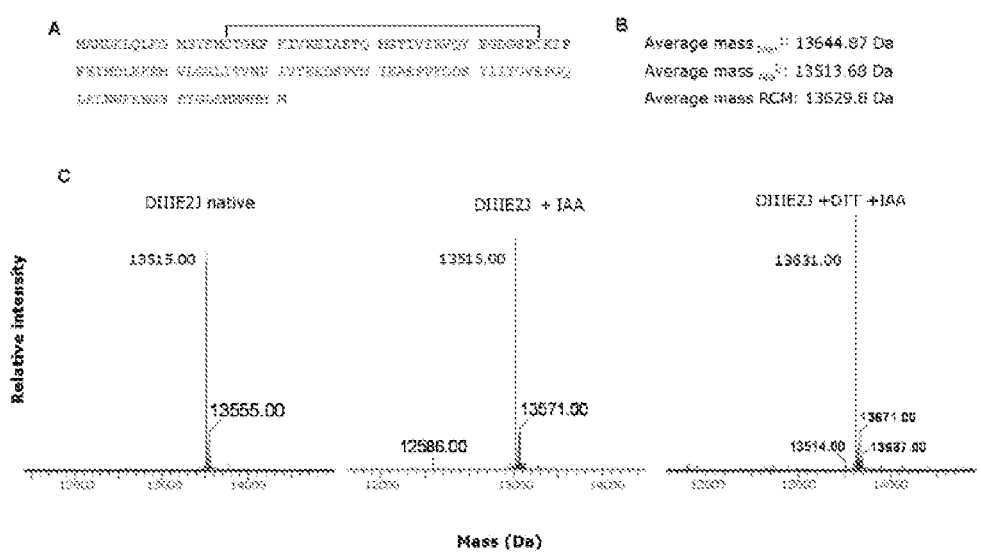
Figure 2:
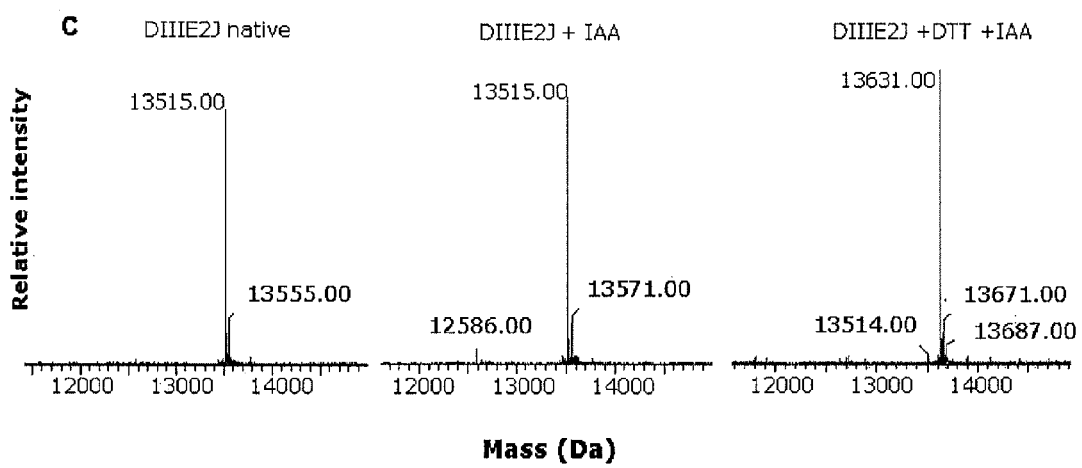

MAMDKLQLKG MSYSMCTGKF KIVKEIAETQ HGTIVIRVQY EGDGSPCKIP FEIMDLEKRH
VLGRLITVNP IVTEKDSPVN IEAEPPFGDS YIIIGVEPGQ LKLNWFKKGS SIGLEHHHHH H

B Average mass $_{Met}{}^{1}$: 13644.87 Da

Average mass $_{Ala}{}^{2}$: 13513.68 Da

Average mass RCM: 13629.8 Da

FIGURE 9

```
                                ↓ ↓↓↓
                 *        *    *   *:   .*.  **       *
SEQ ID. 32   A1  KTCS-------P-KQ-FA-CRD-QITCISKG-WRCDGERDCPDGSDEA-P--BICPQ   42
SEQ ID. 33   A2  QRCQ-------P-NE-HN-CLG-TELCVPMS-RLCNGVQDCMDGSDE--G--PHCRE   41
SEQ ID. 34   A3  PQCQ-------P-GE-PA-CA--NSRCIQBR-WKCDGDNDCLDNSDEA-P--ALCHQ   41
SEQ ID. 35   A4  HTCP-------S-DR-FK-CE--NNRCIPHR-WLCDGDNDCGNSEDES-N--ATCSA   41
SEQ ID. 36   A5  RTCP-------P-NQ-FS-CA--SGRCIPIS-WTCDLDDDCGDRSDES----ASCAY   40
SEQ ID. 37   A6  PTCF-------PLTQ-FT-CN--NGRCIHIN-WRCDNDNDCGDNSDE-----AGCSH   40
SEQ ID. 38   A7  HSCS-------S-TQ-FK-CN--SGRCIPBH-WTCDGDNDCGDYSDET-H--ANCTN   41
SEQ ID. 39   A8  GGCH-------T-DE-PQ-CRL-DGLCIPLR-WRCDGDTDCMDSSDE-----KSCEG   40
SEQ ID. 40   A9  HVCD-------P-SVKFG-CKD-SARCISKA-WVCDGDNDCEDNSDE-----ENCES   41
SEQ ID. 41   A10 LACR-------P-PS-HP-CANNTSVCLPPD-KLCDGNDDCGDGSDE--G--BLC--   40
SEQ ID. 42   A11 SSCR-------AQDE-FE-CA--NGECINFS-LTCDGVPHCKDKSDEKPS---YCNS   42
SEQ ID. 43   A12 RRCK-------KTFR--Q-CS--NGRCVSHM-LWCNGADDCGDGSDEIP-----CNK   39
SEQ ID. 44   A13 TACG--------VGE-FR-CR--DGTCIGNS-SRCNQFVDCEDASDEMN-----CSA   39
SEQ ID. 45   A14 TDCSSYPRLGVK-GVLFQPCER-TSLCYAPS-WVCDGANDCGDYSDE-----RDCPG   49
SEQ ID. 46   A15 PRCP-------L-NY-FA-CP--SGRCIPMS-WTCDKEDDCEHGEDE-----THCNK   39
SEQ ID. 47   A16 KFCS-------E-AQ-FE-CQN-HR-CISKQ-WLCDGSDDCGDGSDEA-A--H-CEG   40
SEQ ID. 48   A17 KTCG-------P-SS-FS-CPG-THVCVPBR-WLCDGDKDCADGADESIA--AGCLY   43
SEQ ID. 49   A18 STCD-------D-RE-FM-CQN-RQ-CIPKH-FVCDHDRDCADGSDES-P--B-CEY   40
SEQ ID. 50   A19 PTCG-------P-SE-FR-CA--NGRCLSSRQWECDGEHDCHDQSDEA-PKNPHCTS   44
SEQ ID. 51   A20 HKCN-------ASSQ-PL-CS--NGRCVABA-LLCNGQDDCGDSSDERG-----CH-   39
SEQ ID. 52   A21 SNCT-------A-SQ-FV-CKN-D-KCIPPW-WKCDTEDDCGDHSDEP-P--D-CPE   40
SEQ ID. 53   A22 PKCR-------P-GQ-FQ-CS--TGICTHPA-FICDGDNDCQDNSDE-----ANCDI   39
SEQ ID. 54   A23 HVCL-------P-SQ-FK-CTN-TNRCIPGI-FRCNGQDNCGDGEDE-----RDCPE   40
SEQ ID. 55   A24 VTCA-------P-NQ-FQ-CS--ITKRCIPRV-WVCDRDHDCVDGSDE--P--ANCTQ  41
SEQ ID. 56   A25 MTCG-------V-DB-FR-CKD-SGRCIPAR-WKCDGEDDCGDSDEP-K--EECDE   42
SEQ ID. 57   A26 RTCE-------P-YQ-FR-CK--NHRCVPGR-WQCDYDHDCGDNSDEE-S----CTP   39
SEQ ID. 58   A27 RPCS-------E-SE-FS-CA--NGRCIAGR-WKCDGDHDCADGSDEK-D----CTP   39
SEQ ID. 59   A28 PRCD-------M-DQ-FQ-CK--SGHCIPLR-WRCDADADCMDGSDE-----BACGT   39
SEQ ID. 60   A29 RTCP-------L-DE-FQ-CNN-T-LCKPLA-WKCDGEDDCGDNSDEN-P--EECAR   41
SEQ ID. 61   A30 FVCP-------P-NRPFR-CKN-DRVCLWIG-RQCDGTDNCGDGTDE-----EDCEP   41
SEQ ID. 62   A31 THCK-------DKKE-FL-CR--NQRCLSSS-LRCNMFDDCGDGSDEBD-----CSI  40
                 1........10........20........30........40........50........
```

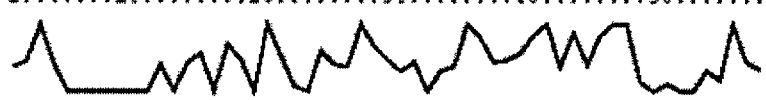

FIGURE 11
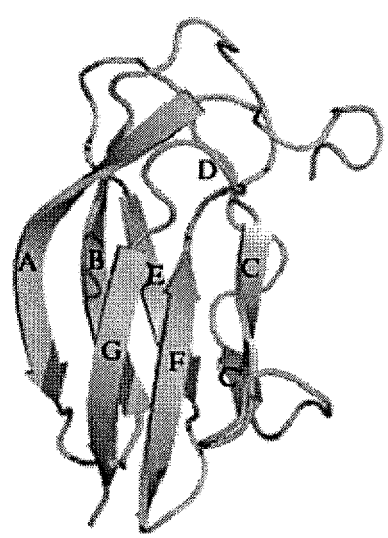 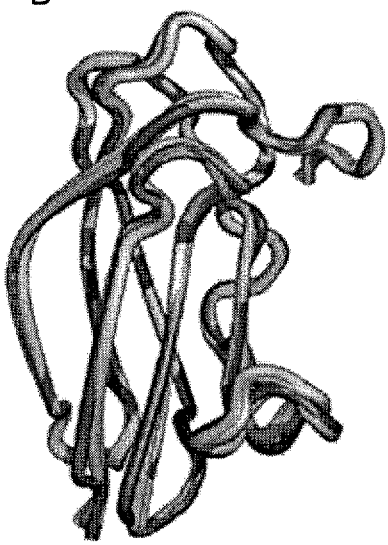
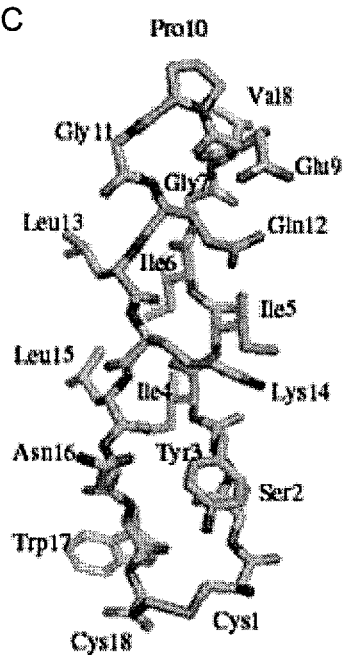
HDIII2CL
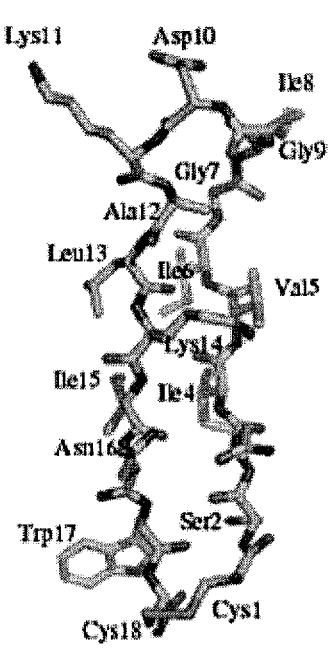
HDIII3CL

FIGURE 12
A
| SEQ ID. No | Peptide | Sequence | Corresponding region in the domain III of VD2 |
|---|---|---|---|
| Seq ID 4 | HIII2Cs | CIIGVEPGQLKC | 379-388 |
| Seq ID 28 | pepDIII-1 | GCGVEPGQC | 381-386 |
| Seq ID 91 | pepDIII-2 | KGMSYSMCTGKFKngQYEGDGSPCKIP | 295-307/325-336 |
B
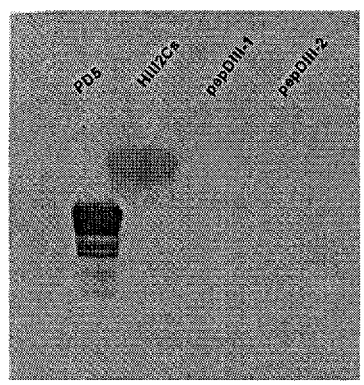
C
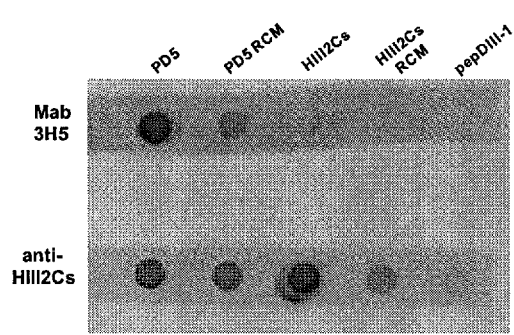

```
DV1     SYIVVGAGEKALKLSW
DV2     SYIIIGVEPGQLKLNW
DV3     SNIVIGIGDKALKINW
DV4     SYIVIGVGNSALTLHW
YFV     SYIIVGRGDSRLTYQW
WNV     SYIVVGRGEQQINHHW
MVE     SYIVVGRGDKQINHHW
KUNJ    SYIVVGRGEQQINHHW
JAE     SYIVVGRGDKQINHHW
SLE     SYIVVGRGTTQINYHW
TBE     NIIYVGE----LSHQW
LAN     NIIYVGD----LNHQW
POW     NIIYVGD----LSQQW
```

FIGURE 18

| | | |
|---|---|---|
| SEQ ID.64 | DV1 | SYIVVGAGEKALKLSW |
| SEQ ID.68 | DV2 | SYIIIGVEPGQLKLNW |
| SEQ ID.69 | DV3 | SNIVIGIGDKALKINW |
| SEQ ID.70 | DV4 | SYIVIGVGNSALTLHW |
| SEQ ID.81 | YFV | SYIIVGRGDSRLTYQW |
| SEQ ID.80 | WNV | SYIVVGRGEQQINHHW |
| SEQ ID.74 | MVE | SYIVVGRGDKQINHHW |
| SEQ ID.72 | KUNJ | SYIVVGRGEQQINHHW |
| SEQ ID.71 | JAE | SYIVVGRGDKQINHHW |
| SEQ ID.78 | SLE | SYIVVGRGTTQINYHW |
| SEQ ID.79 | TBE | NIIYVGE----LSHQW |
| SEQ ID.73 | LAN | NIIYVGD----LNHQW |
| SEQ ID.77 | POW | NIIYVGD----LSQQW |

METHOD TO BLOCK THE INFECTION BY FLAVIVIRUSES, MOLECULES AND USES

This application is the U.S. National Phase of, and Applicants claim priority from, International Application Number PCT/CU2007/000014 filed 26 Apr. 2007 and Cuban Application bearing Serial No. CU 2006-0091 filed 28 Apr. 2006, which are incorporated herein by reference.

SCOPE OF THE INVENTION

The present invention is related to the fields of virology, biotechnology and the pharmaceutical industry. Particularly, this invention is related to methods for modulating or blocking the infection by dengue virus (DV), based on blocking the interaction of the virus with its cellular receptor. Dengue virus (DV) uses the Alfa 2-macroglobulin receptor (A2MR) for its entry into mammalian cells, and that it may use the Alfa 2-macroglobulin (A2M) as a carrier protein that facilitates its interaction with this receptor. The present invention establishes the presence of a direct interaction with human A2M and defines a region of the E protein from the virus that is involved in this interaction. Additionally, the present invention defines peptides derived from protein E that interfere with the interaction of the virus with its cellular receptor, A2MR, and which inhibit the infection of mammalian cells by the virus. These molecules constitute, therefore, potential pharmacological agents for the prevention and treatment of the disease caused by the infection with DV.

STATE OF THE ART

El virus Dengue (DV) belongs to the Flaviviridae family, genus *Flavivirus* (FV). There are four types of DV which are genetically related but are recognized as different serotypes (DV1, DV2, DV3 and DV4) (Henchal E. A. and Putnak J. R. 1990 *The dengue viruses. Clin. Microbiol. Rev.* 3: 376-396). The degree of whole-genome sequence homology between the four serotypes is approximately 70%. A primary infection by a strain from one viral serotype confers long-lasting immunity against subsequent infections by strains belonging to the homologous serotype, but not against strains belonging to the remaining serotypes. Secondary infections with heterologous serotypes are common, and are associated with the appearance of much more severe symptoms of the disease (Halstead, S. B. *Neutralization and antibody-dependent enhancement of dengue viruses.* (2003) *Adv. Virus Res.* 60:421-67., 421-467. Hammon WMc. (1960) *New haemorragic fever in children in the Philippines and Thailand. Trans Assoc Physicians;* 73: 140-155). Therefore, when developing a vaccine against DV it is imperative to guarantee that it provides protection against all four serotypes. However, due to the degree of antigenic variation found even between strains from the same serotype, sometimes the antibodies elicited by the infection with one strain are not protective against an infection by a second strain of the same serotype, thus turning the development of an effective, safe and low-cost vaccine into a major challenge. Therefore, the use of molecules with antiviral activity represents an attractive therapeutic alternative to vaccination.

The replication cycle of the DV virions starts with their entry to the host cell. In mammalian hosts the virions enter the cells using a mechanism of receptor-mediated endocytosis (Hase T., Summers P. L. and Eckels K. H. (1989) *Flavivirus entry into cultured mosquito cells and human peripheral blood monocytes. Arch Virol.* 104: 129-143). The drop in pH that is produced in the endosomes triggers an irreversible conformational change on the virions that induces their fusion to the endosomal membrane and their disassembly (Mukhopadhyay S., Kuhn R. J. and Rossmann M. G. (2005) *A structural perspective of the flavivirus life cycle. Nat Rev Microbiol.* 3: 13-22).

The viral genome thus released to the cytoplasm is translated into a single polyprotein which is co- and post-translationally processed by viral and cellular proteases. The assembly of new virions takes places on the surface of the endoplasmic reticulum, from which the structural proteins and the genomic RNA molecules enter the lumen and continue through the Golgi complex. The virions exit the Golgi complex as mature viral particles inside intracellular vesicles whose contents are released to the extracellular milieu by exocytosis (Mukhopadhyay S., Kuhn R. J. and Rossmann M. G. (2005) *A structural perspective of the flavivirus life cycle. Nat Rev Microbiol.* 3: 13-22).

The entry of DV to the host cell depends on its interaction with specific receptor molecules on the cellular surface. A number of surface molecules have been identified for which there is evidence supporting their involvement in virion entry to the cell, and which are therefore considered as putative viral receptors. Experimentally, the initial steps of a productive DV-cell interaction have been split into a first stage of virus adsorption by interaction with surface molecules, which can take place at 4° C., and another stage during which receptor-mediated endocytosis occurs, and which requires the incubation of the cells at 37° C. as a prerequisite (Hung S L, Lee P L, Chen H W, Chen L K, Kao C L, King C C (1999) *Analysis of the steps involved in Dengue virus entry into host cells Virology;* 257:156-67). These stages involve different regions of the viral envelope protein and different molecules of the cellular surface (Crill W D, Roehrig J T (2001) *Monoclonal antibodies that bind to domain III of dengue virus E glycoprotein are the most efficient blockers of virus adsorption to Vero cells. J Virol.* 75:7769-73).

Among the surface molecules important for this process which have been identified so far are proteoglycans (Chen Y., Maguire T., Hileman R. E., Fromm J. R., Esko J. D., Linhardt R. J. and Marks R. M. (1997) *Dengue virus infectivity depends on envelope protein binding to target cell heparan sulfate. Nat. Med.* 3: 866-871), which have been proposed to be involved in the concentration of the viral particles on the cellular surface for their subsequent interaction with other specific, high-affinity receptors (Halstead S. B., Heinz F. X., Barrett A. D. and Roehrig J. T. (2005) *Dengue virus: molecular basis of cell entry and pathogenesis,* 25-27 Jun. 2003, Vienna, Austria. *Vaccine.* 23: 849-856). Proteins associated to CD14 have also been described as possible receptors in macrophages and monocytes (Chen Y. C., Wang S. Y. and King C. C. (1999) *Bacterial lipopolysaccharide inhibits dengue virus infection of primary human monocytes/macrophages by blockade of virus entry via a CD14-dependent mechanism. J Virol.* 73: 2650-2657). Other molecules tentatively proposed as DV receptors are GRP78/Bip (Jindadamrongwech S. and Smith D R. (2004) *Virus Overlay Protein Binding Assay (VOPBA) reveals serotype specific heterogeneity of dengue virus binding proteins on HepG2 human liver cells. Intervirology.* 47: 370-373. Reyes-Del Valle J., Chavez-Salinas S., Medina F and Del Angel R M. (2005) *Heat shock protein 90 and heat shock protein 70 are components of dengue virus receptor complex in human cells. J Virol.* 279: 4557-4567) and the laminin receptor (Thepparit C. and Smith D. R. (2004) *Serotype-specific entry of dengue virus into liver cells: identification of the 37-kilodalton/67-kilodalton high-affinity laminin receptor as a dengue virus serotype* 1 *receptor. J Virol.* 278: 12647-12656. Tio P. H., Jong W. W. and Cardosa M. J. (2005) *Two dimensional VOPBA reveals laminin receptor (LAMR1) interaction with dengue virus serotypes 1, 2 and 3. Virol J.* 2: 25).

The DC-SIGN protein plays a very important role in the entry of DV virions into immature dendritic cells. However, this protein seems, likewise, to be involved in concentrating the viral particles on the cell surface rather than in their endocytosis (Tassaneetrithp B., Burgess T. H., Granelli-Piperno A., Trumpfheller C., Finke J., Sun W., Eller M. A., Pattanapanyasat K., Sarasombath S., Birx D. L. Steinman R. M., Schlesinger S., and Marovich M. A. (2003) *DC-SIGN (CD209) mediates Dengue Virus infection of human dendritic cells. J. Exp. Med.* 197: 823-829. Navarro-Sanchez E., Altmeyer R., Amara A, Schwartz O, Fieschi F, Virelizier J L., Arenzana-Seisdedos F. and Despres P. (2003) *Dendritic-cell-specific ICAM3-grabbing non-integrin is essential for the productive infection of human dendritic cells by mosquito-cell-derived dengue viruses. EMBO Rep.* 4: 723-728. Lozach P Y, Burleigh L, Staropoli I, Navarro-Sanchez E, Harriague J, Virelizier J L, Rey F A, Despres P, Arenzana-Seisdedos F, Amara A (2005) *Dendritic cell-specific intercellular adhesion molecule 3-grabbing non-integrin (DC-SIGN)-mediated enhancement of dengue virus infection is independent of DC-SIGN internalization signals. J Biol Chem.* 280:23698-708).

The envelope protein (E) of DV and other FV plays a fundamental role in binding to cellular receptors, membrane fusion and virion assembly. Consequently, it constitutes one of the main determinants for host range and virulence, and for the induction of protective immunity (Heinz F. X. (1986) *Epitope mapping of flavivirus glycoproteins. Adv Virol. Res.* 31: 103-168. Modis Y., Ogata S., Clements D. and Harrison S. C. (2005) *Variable surface epitopes in the crystal structure of dengue virus type 3 envelope glycoprotein. J Virol.* 79: 1223-1231). This protein, with a molecular mass of 53 to 54 kDa, is the most conserved of the DV structural polypeptides, being 40% identical in its amino acid sequence among the different FV (Mukhopadhyay S., Kuhn R. J. and Rossmann M. G. (2005) *A structural perspective of the flavivirus life cycle. Nat Rev Microbiol.* 3: 13-22). X-ray crystallography (Modis Y., Ogata S., Clements D. and Harrison S. C. (2003) *A ligand-binding pocket in the dengue virus envelope glycoprotein. Proc Natl Acad Sci USA.* 100: 6986-6991) and electron cryomicroscopy studies (Kuhn R. J., Zhang W, Rossmann, M. G., Pletnev S. V., Corver J., Lenches E., Jones C. T., Mukhopadhyay S., Chipman P. R., Strauss E. G., Baker T. S. and Strauss J. H. (2002) *Structure of Dengue Virus: Implications for Flavivirus Organization, Maturation, and Fusion. Cell.* 108: 717-725) have revealed that, in a fashion similar to other FV, the E protein from DV is found as dimers in the surface of mature virions.

The N-terminal ectodomain of the E protein is formed by 80% of the approximately 500 aminoacid residues of the whole molecule. The remaining residues constitute a transmembrane region that anchors the protein to the lipid envelope surrounding the virus. There are 12 strictly conserved Cys residues in the primary structure of protein E, which are involved in the formation of 6 disulphide bridges (Nowak T. and Wengler G. (1987) *Analysis of the disulphides present in the membrane protein of the West Nile flaviviruses. Virology.* 156: 127-137. Hahn Y. S., Daller R., Hunkapiller T., Dalrymple J. M., Strauss J. H., and Strauss E. G. (1988) *Nucleotide sequence of Dengue 2 RNA and comparison of the encoded proteins with those of other flaviviruses. Virology.* 162: 167-180) that play a very important role in the formation of the antigenic epitopes of this molecule (Roehrig J. T., Volpe K. E., Squires J., Hunt A. R., Davis B. S. and Chang G. J. (2004) *Contribution of disulfide bridging to epitope expression of the dengue type 2 virus envelope glycoprotein. J Virol.* 78: 2648-2652).

The polypeptide chain forming the soluble ectodomain from protein E folds into three structural domains: A central pleated-sheet domain (domain I), an elongated dimerization domain (domain II) and a third, immunoglobulin-like domain (domain III) (Rey F. A, Heinz F. X, and Mandl C. (1995) *The envelope glycoprotein from tick-borne encephalitis virus at 2 Å resolution. Nature.* 375: 291-298. Modis Y., Ogata S., Clements D. and Harrison S. C. (2003) *A ligand-binding pocket in the dengue virus envelope glycoprotein. Proc Nat Acad Sci USA.* 100: 6986-6991).

Domain III from the E Protein of DV

Domain III (DIII) is of major functional importance in protein E. Many mutations determining escape to neutralizing antibodies or mediating alterations to viral phenotype (attenuation or virulence determinants) map to the upper and lateral surfaces of this domain. DIII is found on the C-terminal region of each protein E monomer, and comprises aminoacids 294 to 392. This domain constitutes the most prominent region on the virions, in which it exposes its lateral face and is located around the 5× and 3× symmetry axes, having each 60 DIII molecules (Kuhn R. J., Zhang W., Rossmann, M. G., Pletnev S. V., Corver J., Lenches E., Jones C. T., Mukhopadhyay S., Chipman P. R., Strauss E. G., Baker T. S. and Strauss J. H. (2002) *Structure of Dengue Virus: Implications for Flavivirus Organization, Maturation, and Fusion. Cell.* 108: 717-725).

The structure of DIII is similar to that of the constant region of immunoglobulins. It is formed by a β-barrel with two antiparallel beta sheets, one composed by strands A, B, C', D and E, and the other by strands C, F and G. The tertiary structure of DIII depends, to a large extent, on the presence of a single disulphide bridge, formed between 2 Cys residues which are strictly conserved among all FV. The reduction of this bridge decreases or eliminates binding by neutralizing antibodies specific for DIII. A wealth of data, obtained from the structural analysis of protein E and DV virions, as well as from direct experimentation, indicate that DIII is part of the region in protein E that interacts with the cellular receptors (Hung J J, Hsieh M T, Young M J, Kao C L, King C C, Chang W (2004) *An external loop region of domain III of dengue virus type 2 envelope protein is involved in serotype-specific binding to mosquito but not mammalian cells. J Virol.* 78:378-88, Crill W D, Roehrig J T (2001) *Monoclonal antibodies that bind to domain II of dengue virus E glycoprotein are the most efficient blockers of virus adsorption to Vero cells. J Virol.* 75:7769-73, Thullier P, Demangel C, Bedouelle H, Megret F, Jouan A, Deubel V, Mazie J C, Lafaye P (2001) *Mapping of a dengue virus neutralizing epitope critical for the infectivity of all serotypes: insight into the neutralization mechanism J Gen Virol.* 82(Pt 8):1885-92).

The studies on structure-function relationships of DIII have also employed synthetic peptides. For example, peptide 386-397, which includes the G beta strand from DIII of DV2, is recognized by the 3H5 neutralizing monoclonal antibody, which is known to interfere with binding of the virus to the cells and inhibits erythrocyte hemagglutination (Roehrig J T, Bolin R A, Kelly R G (1998) *Monoclonal antibody mapping of the envelope glycoprotein of the dengue 2 virus, Jamaica Virology.* 246:317-28). However, several mutations in this region of protein E are not detrimental for binding of 3H5 (Hiramatsu K, Tadano M, Men R, Lai C J (1996) *Mutational analysis of a neutralization epitope on the dengue type 2 virus (DEN2) envelope protein: monoclonal antibody resistant DEN2/DEN4 chimeras exhibit reduced mouse neuroviru-* lence. *Virology*. 1996, 224:437-45), whereas, mutations of residues E383, P384 and G385 abrogate this binding. It has also been shown that peptide 380-389, corresponding to the F-G loop and part of strand G, can block the interaction of DIII with mosquito cells but not, however with mammalian cells (Hung J J, Hsieh M T, Young M J, Kao C L, King C C, Chang W (2004) *An external loop region of domain III of dengue virus type 2 envelope protein is involved in serotype-specific binding to mosquito but not mammalian cells. J Virol.* 78:378-88). On the other hand, peptide 306-314 from DV1, corresponding to the A beta strand, is recognized by the 4E11 neutralizing antibody (Thullier P, Demangel C, Bedouelle H, Megret F, Jouan A, Deubel V, Mazie J C, Lafaye P (2001) *Mapping of a dengue virus neutralizing epitope critical for the infectivity of all serotypes: insight into the neutralization mechanism J Gen Virol.* 82(Pt 8):1885-92). This peptide is capable of inhibiting viral infection in Vero cells when used at high concentrations (approximately 500 µM).

Alpha 2-macroglobulin (A2M)

The human A2M belongs to the family of the alpha macroglobulins, whose members share the characteristic of being able to bind a wide range of peptides, proteins and particles, thus serving as a humoral line of defense in the plasma and tissues of vertebrates. There are human A2M homologues in the circulation of vertebrates and invertebrates, as well as in the egg white from birds and reptilians (Borth W (1992) *Alpha 2-macroglobulin, a multifunctional binding protein with targeting characteristics*. 6:3345-53).

Human A2M is a glycoprotein formed by four subunits 180 kDa each, forming a 720 kDa homotetramer. This protein is synthesized in different cell types, e.g. lung fibroblasts, monocytes/macrophages, hepatocytes and astrocytes. There are five reactive sites per subunit: 1) The "bait" region, a stretch of 25 aminoacids located approximately in the middle of each subunit, which can be cleaved by proteases belonging virtually to any mechanistic class, produced by the host or any incoming microorganism; 2) A thioester bond between the side chains of a cysteine and a glutamine, which can be cleaved either by high temperatures, the presence of small nucleophiles such as primary amines, reducing agents or water; 3) The receptor binding site, comprised by C-terminal amino acids from each subunit, which is exposed only after cleavage of the thioester bond; 4) A transglutaminase binding site, located 20 aminoacids before the "bait" region and 5) A $Zn^{2+}$-binding site.

Human A2M inhibits a large number of proteolytic enzymes involved in a wide range of biological processes such as fibrinolysis, coagulation, digestion, the immune response and invasive tissue growth. Cleavage of the "bait" region by a protease induces a conformational change in A2M which is tightly coupled to the hydrolysis of the thioester bond, as a result of which A2M entraps the protease within its new conformation. The net result of this process is that A2M prevents the access of large substrates to the active site of the protease. This conformational change also exposes the receptor binding region in each subunit of the tetramer, and therefore the A2M-protease complexes are quickly eliminated from the circulation by receptor-mediated endocytosis (Gonias S L, Balber A E, Hubbard W J, Pizzo S V (1983) *Ligand binding, conformational change and plasma elimination of human, mouse and rat alpha-macroglobulin proteinase inhibitors. Biochem J.* 1. 209:99-105).

Besides its role as a proteolytic regulator, A2M is also involved in many processes, due to its ability for binding a number of different molecules and then release this cargo at different stages along the endocytic pathway. The functions of A2M as a carrier protein have been associated to the transport from the endocytic pathway to the cytoplasm, transcytosis and degradation with or without the involvement of the antigen presentation machinery (Pizzo Salvatore V, Gron Hanne (2004) *Immune response modulator alpha-2 macroglobulin complex*, U.S. Pat. No. 6,403,092).

The nature of the chemical interaction with A2M has been found to be a key determinant for the final cellular destination of the cargo peptide or protein. Reversible interactions allow the cargo to assume a biological role once dissociated from the complex in the early stages of the endocytic pathway, whereas irreversibly bound proteins or peptides usually reach the lysosomal compartments, where they are degraded (Borth W (1992) *Alpha 2-macroglobulin, a multifunctional binding protein with targeting characteristics The FASEB journal* 6:3345-53).

The Alpha-2 Macroglobulin Receptor

The A2M receptor (A2MR), also known as low-density lipoprotein receptor-related protein (LRP1) and as CD91, has been linked to numerous physiological roles of vital importance, such as the metabolism of lipids, hemostasis, the activation of lysosomal enzymes and neurotransmission.

A2MR is a heterodimer formed by an extracellular 500 kDa α chain, non-covalently bonded to a transmembrane 85 kDa β chain. The α chain contains four clusters of 2, 8, 10 and 11 complement-like Cys-rich ligand binding sites. After each cluster of ligand binding sites there is an EGF-like domain formed by Cys-rich regions and YWTD domains. The cytoplasmic tail of the β chain has two NPxY motifs that are recognized by adaptor proteins involved in signaling and endocytosis (Herz J, Strickland D K. (2001) *LRP: a multifunctional scavenger and signaling receptor. J Clin Invest.* 108:779-84).

A2MR recognizes at least 30 different ligands belonging to different protein families including lipoproteins, proteases, protease-inhibitor complexes, extracellular matrix proteins, bacterial toxins, viruses and several intracellular proteins. The studies aimed at detailing the characteristics of the interactions of these molecules with A2MR have revealed that the capacity of the receptor for recognition of such a wide array of ligands is provided by the presence of the 31 ligand binding sites, each presenting a unique interaction surface. A high-affinity interaction with the receptor, therefore, involves simultaneous binding to several ligand binding sites.

The human A2MR also recognizes ligands from other species, with affinity constants similar to those displayed for the endogenous ligands.

DETAILED DESCRIPTION OF THE INVENTION

The interaction of viruses with their cellular receptors is a prime determinant of infectivity. The obtention of compounds that block virus-receptor interactions can lead to the development of potent antiviral drugs.

In the case of DV, it has been shown that there is a high correlation between viremia and the severity of the disease. The obtention of an effective antiviral drug able to decrease viral loads in the infected patients is, therefore, a very attractive strategy for the control of the severe forms of the disease. However, the development of antiviral drugs for DV based on the blocking of the virus-receptor interactions has been hampered by the lack of knowledge of the identity of the receptor that mediates virus endocytosis, the nature of the interaction, and the determinants for recognition.

The present invention is based on the findings that DIII from protein E of DV2, strain Jamaica (Seq. ID.1) can form reversibly bound complexes with A2M from human plasma (Seq. ID. 2), and that blocking the A2MR receptor (Seq. ID.

3) by means of anti-receptor antibodies or competitive ligands can inhibit the infection by DV of mammalian cells. The former suggests that A2M, in this setting, functions as a carrier protein from the virus to the A2MR receptor, serving as one of the means for viral entry to the cell through endocytosis mediated by this receptor.

A2M and its receptor, A2MR, are widely distributed throughout different tissues and organisms, where homologues for these proteins have been found. Both molecules (A2M and A2MR) have evolved from ancestral protein families. Since there is a high degree of structural and aminoacid sequence homology between the members of each family, the activity of these molecules as DV receptors is potentially present in a large variety of cell types and organisms. Also, given the high similarity between the ligand binding domains of the different members of the LDL receptor family, it is possible to infer the existence of an interaction between DV and other receptors belonging to this family.

As an example, the members of the minor family of the rhinoviruses use different members of the LDL receptor family as cellular receptors; in this case they are the low-density lipoprotein receptor, the very low density lipoprotein receptor, and LRP1 (Hofer F, Gruenberger M, Kowalski H, Machat H, Huettinger M, Kuechler E, Blass D (1994) *Members of the low density lipoprotein receptor family mediate cell entry of a minor-group common cold virus. Proc Natl Acad Sci* 1; 91:1839-42). It is known that the surface proteins of this viral family that interact with their receptors are able to bind, with varying affinities, to members of the LDL receptor family from primate and murine cells, and it has been established that such interactions mediate viral entry in these cell types.

There is also a high degree of structural and sequence homology between the E proteins from different FV and, therefore, other FV might use the A2MR or other receptors from the LDL receptor family. The *Flavivirus* genus comprises more than 70 viruses, many of which are potent human pathogens. The diseases caused by flaviviral infections are characterized by febrile symptoms that can have haemorrhagic manifestations, encephalitis and hepatic complications. Besides the four serotypes of DV, other conspicuous members of the genus with importance for human health are the Yellow Fever Virus, the Japanese Encephalitis Virus, the Tick-borne Encephalitis Virus, the Murray Valley Encephalitis Virus, and the West Nile Virus.

Based on the findings mentioned above, one object of the present invention is a method for blocking the infection of cells by DV based on the interference of the interaction of the virus with the A2MR receptor. Alternatively, it is possible to modulate the DV infection by interfering the interaction with human A2M. In this context, interfering the interaction with the receptor or with A2M means either reducing or increasing this interaction. The reduction of the interaction would abort viral infection at a very early stage, since the virus would not enter the cell; on the other hand, increasing or potentiating this interaction would prevent the release of the endocytosed virus at the beginning of endosomal acidification, affecting the events of membrane fusion and release of the viral RNA. Both types of interference have been effective for the neutralization of the infectivity of other viruses.

The binding of DV to the cells can be interfered by molecules interacting with either of the two surfaces implicated in this event: the interacting surface of protein E or the interacting surface of the A2MR receptor. Likewise, it is possible to interfere with the union of DV to the cells by using molecules that bind the surface of interaction of the human A2M with the viral protein.

Specifically, the present invention shows that the protein known as Receptor-Associated Protein (that will be referred to as RAP henceforth), which constitutes one of the natural ligands of A2MR, as well as antibodies against this receptor, are capable of inhibiting the infection by DV of Vero cells.

Therefore, an agent for interfering the interaction of DV with the A2MR receptor may consist of a receptor ligand purified from natural sources or obtained by means of recombinant DNA techniques; or may consist of a purified soluble variant of the receptor comprising its extracellular portion (the region comprised between residues 20 to 4419 in the sequence referred to in the sequence listing as Seq. ID. 3) or a fragment derived from this portion that is still capable of binding to DV. Preferably, such a fragment would comprise a segment corresponding to one of the ligand binding domains of this receptor (regions comprised between residues 25 to 66, or 70 to 110, or 852 to 892, or 893 to 933, or 934 to 973, or 974 to 1013, or 1014 to 1053, or 1060 to 1099, or 1102 to 1142, or 1143 to 1182, or 2522 to 2563, or 2564 to 2602, or 2603 to 2641, or 2642 to 2690, or 2694 to 2732, or 2733 to 2771, or 2772 to 2814, or 2816 to 2855, or 2856 to 2899, or 2902 to 2940, or 3332 to 3371, or 3372 to 3410, or 3411 to 3450, or 3451 to 3491, or 3492 to 3533, or 3534 to 3572, or 3573 to 3611, or 3612 to 3649, or 3652 to 3692, or 3693 to 3733, or 3739 to 3778, of the sequence identified in the sequence listing as Seq. ID. 3). An interfering agent can also consist of a synthetic ligand, developed for this purpose. An example of the latter would be a synthetic peptide developed using methods known in the art, based on the information provided by the present invention.

Informatics-based methods have become powerful tools for drug design. These methods have the advantage of being able to evaluate large numbers of compounds, consequently providing for great savings in time and experimental work. The successful use of these methods requires the availability of data on the three-dimensional structure of the proteins and ligands involved in the interaction to be affected. Any experimental data that help to define the surface of interaction in any of the reacting molecules are also an invaluable aid in this context.

Considering the state of the art in computational techniques for drug development based on molecular docking, the findings described in the present invention about the role of A2M and its receptor A2MR in the cellular entry of DV provide a target for experiments of virtual screenings for compounds inhibiting this interaction, as potential antiviral drugs or leads for their development. The three-dimensional structures of the ectodomain of protein E and of the DV virion are available, and so are the structural coordinates of the domain mediating the binding of A2M to A2MR, as well as those of several ligand binding domains from members of the LDL receptor family. On the other hand, the present invention also defines aminoacids involved in the interaction of DV with its cellular receptor, and provides information about the structural determinants for this interaction.

Therefore, one mean for obtaining the sequences of synthetic peptides and/or the structure of small molecules that can interfere the interaction of DV with the A2MR receptor may be the use of theoretical methods that implicitly employ one or several methods of computational modeling and models of the three-dimensional structure of DIII, as well as of any of the ligand binding domains of the A2MR receptor. Employing any of these methods for computational modeling, and based on the spatial coordinates for the structure of DIII, it is possible to model the backbone of a polypeptide chain forming an anti-parallel beta hairpin that includes a beta turn in the connecting chain between both strands. Additionally, it is possible to model the side chains of the polypeptide in such a way that the chemical identity of these chains, as well as their conformation, lead to energetically favorable atomic contacts. It is also possible to computationally explore the sequence space, as well as the conformational space of the peptide, the rotamers of the side chains, and to select the most favorable side chains using as a criterion an energy evaluation of the models, which is predictive of a higher affinity for the peptide-protein interaction.

The coordinates of the model of interaction of DIII with one and/or several ligand binding domains of the A2MR receptor can be obtained through experimental means, using X-ray diffraction and/or NMR techniques, or by using computational modeling.

It is also possible to use a computational method of molecular docking to reproduce the atomic details of the interaction between the peptides corresponding to the FG beta hairpin from DIII of protein E from different flaviviruses and the ligand binding domains from the A2MR receptor. Likewise, it is possible to select from a database of molecular structures those compounds which reproduce the characteristics of this interaction, which would therefore constitute prospective inhibitors for blocking flaviviral infections.

Other interfering agents can be obtained by using an antibody or an antibody fragment selected through any of the methods available in the art, e.g. by selection of phage-displayed antibody libraries. In the latter case, the selection can be implemented in such a way that it propitiates the obtention of a specific response against the regions involved in the DV-A2MR or DV-A2M interactions. If the selection is implemented in such a way that a response against the region of interaction of A2MR or A2M is selected, the selection must allow the discrimination between interference of this interaction and interference with the physiological functionality of these molecules.

An object of the present invention is also a method for blocking the infection of cells by DV, based on the use of an agent that interferes with the expression of the A2MR receptor. Using the available methodology in the state of the art for the development of antiviral drugs, it is possible to deduce that one example would be the use of a short interfering RNA (siRNA) that temporarily decreases or eliminates the expression of the A2MR receptor.

Another embodiment of the present invention is a method for the prevention or treatment of the disease caused by DV infection, comprising the administration of an effective amount of a molecule with antiviral activity that interferes with the interaction of DV with a cellular receptor, wherein said cellular receptor is the A2MR cellular receptor. The molecule with antiviral activity, formulated in acceptable conditions according to the current regulations for pharmaceutical preparations, can be administered in an effective dose before the infection or after the appearance of the symptoms of the disease, having a confirmatory laboratory diagnosis for DV infection.

The molecule with antiviral activity against DV may be employed as a prophylactic drug before exposure in high-risk areas for DV infection. A high-risk area for DV infection is a geographical region known to harbor the vector for transmitting DV, that is, the Aedes mosquito, and where detectable circulation of any DV serotype is taking place.

Another embodiment of the present invention is a method to prevent and/or treat the disease caused by DV, which comprises the use of an agent that interferes the interaction of the virus with human A2M.

The present invention is also related to a method for predicting the susceptibility of a specific cell type for DV infection. This prediction can be made by testing for the presence of the gene coding for the A2MR receptor, where the term gene includes the segment of DNA involved in the production of the polypeptide chain, as well as preceding and succeeding regions and intervening sequences (introns) between the coding sequences (exons).

The method comprises the use of 20-50 base pairs-long polynucleotides which hybridize to selected target regions on the sequence of the gene coding for the A2MR receptor and which shall henceforth be denominated as a probe, in conditions allowing the detection of hybridizing targets with 80 to 95% sequence identity to the probe. The procedures used for achieving higher stringency (i.e. detection of regions with only 95% or higher sequence identity to the probe) are well known in the art. The probe used for hybridization can potentially be able to determine whether the gene codes for a protein that still retains all the functionality of a DV receptor. The present invention also comprises the use of molecules which have been developed for interference of the interaction of DV with its receptor, for estimating the susceptibility of a specific cell type to DV infection. The method consists on the detection of the A2MR protein on the cell surface. For example, in may comprise the use of an antibody recognizing the A2MR receptor, or one of its ligands, or a synthetic peptide which interacts with the receptor, which are incubated with the cells to be tested, after which their binding to the cell surface is detected by means of any of the current techniques in the state of the art, such as fluorophore-assisted flow cytometry. Among the ligands that can be used for this embodiment are A2M and RAP.

Another embodiment of the present invention comprises a method for estimating the susceptibility of a specific cell type to DV infection, based on the detection of the A2MR protein. The method involves the obtention of a preparation containing the totality of cellular proteins or a subcellular fraction. The proteins, previously fractioned by electrophoresis in acrylamide gels or not, are transferred to a nitrocellulose membrane, and the presence of the A2MR receptor is detected by means of an antibody that specifically recognizes this molecule, followed by the detection of the bound antibody. Alternatively, the nitrocellulose membrane containing the transferred proteins is incubated in a solution containing one of the ligands of the receptor, e.g. A2M or RAP, and the bound ligand is detected later.

The present invention is also related to a method for screening and identifying a compound which protects against DV infection, comprising the determination of the capacity of the compounds under evaluation to block the interaction of DV with the A2MR receptor. A method based on this principle can employ preparations containing DV virions or, alternatively, the ectodomain from the E protein of DV, or a recombinant protein comprising DIII from said protein. The method involves the incubation of the A2MR receptor jointly with a preparation containing DV and the compound whose blocking capacity is to be evaluated, followed by the estimation of the amount of bound virus and its comparison with the amount of bound virus in the absence of the tested compound. The detection is performed, preferably, by using the receptor bound to or immobilized on a solid phase, adding the mixture of virions and the evaluated compound in solution.

The A2MR preparation can consist of a sample purified from natural sources, where the A2MR receptor accounts, preferably, for at least 75% of the total protein contents of the sample. Some examples of natural sources are cell/tissue homogenates, or culture supernatants from cell culture, or human plasma. The A2MR preparation can also consist of a recombinant protein comprising the α chain of the receptor or a fragment thereof, which retains the functionality as DV receptor.

The present invention also comprises a method for screening and identifying a compound that can protect against DV infection, based on determining the capacity of the compounds under evaluation to block the interaction of DV with human A2M. A method based on this principle may, alternatively, employ the ectodomain from the E protein of DV, or a recombinant protein comprising DIII from said molecule. In order to evaluate the activity of the compounds being screened, the substance under evaluation is incubated with A2M and its capacity to interfere the interaction with DV, or the ectodomain from protein E, or DIII from protein E, is estimated.

FIGURE DESCRIPTION

FIG. 1. Characterization of the purified preparation of DIIIE2J. (A) 45 μg of DIIIE2J were loaded on a reversed phase C4 column. The chromatographic run was performed at 37° C., using a high performance liquid chromatography system fitted with 2 pumps and a controller. The elution of the protein was achieved by applying a 10 to 60% (v/v) linear gradient of acetonitrile in 0.1% (v/v) trifluoroacetic acid at a flow of 0.8 mL/min, detecting at 226 nm. (B) Analysis by 15% SDS-PAGE. Lane 1: Molecular weight markers. Lane 2: 12 μg of the purified preparation of DIIIE2J, diluted 1:1 in non-reducing sample buffer. The protein bands were stained following the methodology described by Heukeshoven, J. and Dernick, R., (1985). *Simplified method for silver staining of proteins in polyacrylamide gels and the mechanism of silver staining. Electrophoresis* 6: 103-112.

FIG. 2. Determination of the molecular mass and of the status of the disulphide bridge by mass spectrometry. (A) Amino acid sequence predicted from the DNA sequence of the cloned fragment (SEQ ID. 22). (B) Expected average mass calculated from the predicted aminoacidic sequence of the protein, assuming that the N-terminal methionine is not removed (Met1) or completely removed (Ala2). RCM: Expected average mass of the Ala2 protein after the incorporation of iodoacetamide in each cysteine residue. (C) Deconvoluted mass spectra for DIIIE2J. Native: Unmodified protein, collected from rp-HPLC. +IAA: Protein incubated for 30 min. at 25° C. with iodoacetamide. +DTT +IAA: Protein incubated for 2 hours at 37° C. with 10 mM DTT, followed by 30 min. incubation at 25° C. with iodoacetamide.

FIG. 3. Dot blotting for the analysis of the antigenicity of DIIIE2J with murine and human antibodies. The rows contain the different preparations used to sensitize the nitrocellulose membrane, whereas the columns represent the arrangement of the different antibody preparations. $C^+$: Preparations of viral antigen from serotype 2, obtained by the sucrose-acetone method (Clarke D. H. and Casals J. (1958). *Techniques for hemagglutination and hemagglutination inhibition with arthropod-borne viruses. Amer. J. Trop. Med. Hyg.* 7: 561-573) from brain homogenates of intracranially inoculated OF1 suckling mice. $C^-$: Brain homogenates from non-inoculated OF1 suckling mice, processed by the sucrose-acetone method.

FIG. 4. Recognition of DIIIE2J, covalently immobilized to a chromatographic gel, by anti-DV2 antibodies. Twenty microliter aliquots of the affinity gel with DIIIE2J as the ligand were incubated with different antibody preparations for 30 min at 25° C. The unbound fraction was removed by low-speed centrifugation, and the gel was washed extensively with PBS pH 7.4, 0.1% Tween-20.

FIG. 5. Direct binding between A2M and DIIIE2J with both proteins in solution. (A) Analysis of the quality of the preparation of purified A2M used in the direct binding experiments. SDS-PAGE (10%) in non-denaturing, non-reducing conditions. Lane 1: Staining with Coomassie Blue. Lane 2: Western blotting immunoidentification, employing a polyclonal anti-human A2M preparation (Sigma, USA). (B-F): Chromatographic profiles of the gel filtration runs used for separating the different species. A Superdex 200 HR 10/30 column, equilibrated in $NaHPO_4$ 50 mM pH 7.0, 300 mM NaCl buffer, was employed throughout. The run was performed at a flow of 0.4 mL/min, and was monitored at 280 nm. The samples were loaded in a volume of 200 μL. (A) 100 μg of DIIIE2J. (B) 70 μg of non-activated A2M. (C) 100 μg of DIIIE2J incubated for 1 hour at 25° C. with 70 μg of non-activated A2M. (D) 70 μg of A2M_MeNH$_2$. (E) 100 μg of DIIIE2J incubated for 1 hour at 25° C. with 70 μg of A2M A2M_MeNH$_2$. The arrows indicate, in each chromatogram, the fractions that were collected for later analysis by SDS-PAGE. The asterisk marks the time corresponding to the elution of one total column volume. (G): Analysis by 12.5% SDS-PAGE of the protein species present in the fractions collected from the different chromatographic runs. The samples collected from each run were precipitated with acetone, and the pellets were resuspended in 15 μL of buffer sample and electrophoresed. The letter of the corresponding chromatogram, as well as the description of the loaded sample, is indicated on top of each lane. The arrow indicates the position of the DIIIE2J band in the gel.

FIG. 6. Direct binding between DIIIE2J and A2M, measured by Biacore. Response curves obtained during and after the injection of (B) Monoclonal antibodies against DV serotype 2 (3H5) and against all FV (4G2); (C) Polyclonal mouse antibody preparations obtained by immunization with DV1 and DV2, including pre-immune sera and (D) A2M dilutions, at concentrations from 0.3 μMol/L to 3 μMol/L. The run was performed on PBS pH 7.4 at 25° C. The different A2M dilutions were loaded at a flow of 5 μL/min for 20 min. The response is represented in resonance units (RU) corrected for unspecific binding using the response from the channel without immobilized protein (less than 5% of the specific signal).

FIG. 7. Inhibition of the binding of DIIIE2J to Vero cells by A2M and RAPR13. The pre-fixed cells were incubated with the fluoresceinated proteins, and the intensity of the fluorescence due to binding of the fluoresceinated ligands to the cells was measured by flow cytometry. Each experimental point represents data gathered from a minimum of 20 000 cells. (A) Binding of A2M and RAPR13 to the cells. The depicted values correspond to the average of the intensity of the fluorescence at each point of the assay minus the fluorescence obtained with untreated cells. (B) and (C) The cells were incubated with fluoresceinated DIIIE2J in the presence or absence of the non-fluoresceinated ligands, using the molar ratio indicated on each case. The % binding was calculated from the ratio of the average intensity of the fluorescence of the cells incubated with the mixture of fluoresceinated DIIIE2J plus the proteins, between that of the cells incubated only with fluoresceinated DIIIE2J.

FIG. 8. Effect of recombinant RAP on the infection of Vero cells with DV2, strain S16803. Vero monolayers at 90% confluence were pre-incubated with different dilutions of RAPR13 or BSA, for 1 hour at 37° C., followed by the addition of the viral preparation at a multiplicity of infection of 1 and another incubation at 37° C. for 1 hour. After eliminating the unbound viruses, MEM medium supplemented with non-essential aminoacids, 1% FCS and 1% CMC was added, and the cells were incubated for 5 days at 37° C. The lytic plaques were visualized by staining the monolayer with Naphtol Blue Black. The assays were performed in 24-well plates, using duplicates for each point of the assay.

FIG. 9. Multiple sequence alignment of the ligand binding domains of the A2MR receptor (SEQ ID. 3, LRP1_human at the SwissProt databank). The alignment was performed using the ClustalX application (Higgins D., Thompson J., Gibson T. Thompson J. D., Higgins D. G., Gibson T. J. (1994). *CLUSTAL W: improving the sensitivity of progressive multiple sequence alignment through sequence weighting, position-specific gap penalties and weight matrix choice. Nucleic Acids Res.* 22:4673-4680). The arrows denote the residues belonging to the ligand binding patches. The lower part of the figure shows a schematic representation of the degree of conservation per residue.

Figure 10:
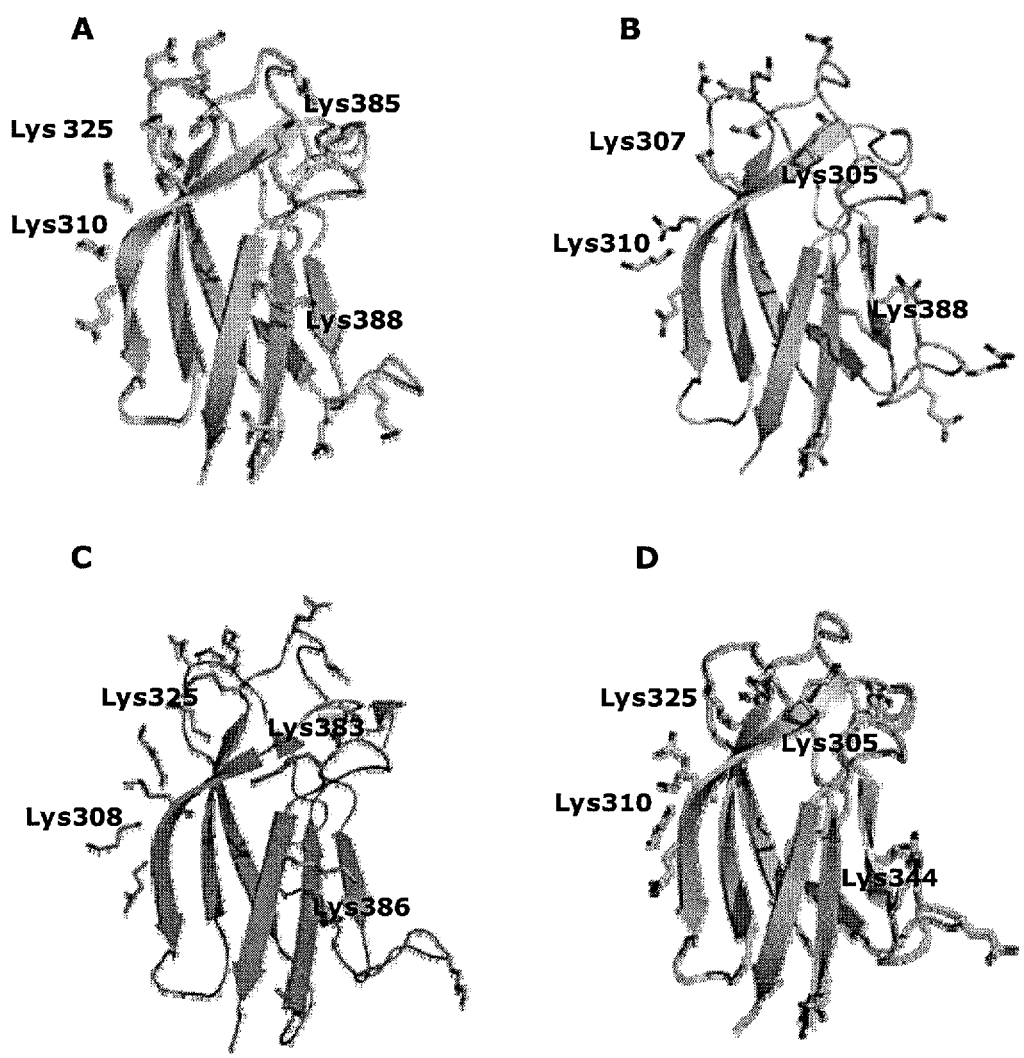

FIG. 10. Three-dimensional model of the structure of DIII from protein E of DV. (A) DV1, (B) DV2, (C) DV3, and (D) DV4. The positively charged patches on the surface of DIII are shadowed, using oval patches in two gray tones: Dark gray on the surface of the beta sheet defined by strands A, B, C', D and E, and light gray for the patches on the surface corresponding or adjacent to the FG beta hairpin (see FIG. 10A).

FIG. 11. Design of the peptides for blocking the infection by DV, based on the FG beta hairpin. (A) Schematic representation of the three-dimensional structure of DIII from DV2. The scheme emphasizes secondary structure elements. (B) Structural superposition of the models for the tertiary structure of DIII from the four serotypes of DV. The models are represented with varying gray tones for the different serotypes of the virus. (C) and (D) Three-dimensional models of the structure of peptides HDIII2CL and HDIII3CL, respectively.

FIG. 12. (A) Sequence of the peptides designed to mimic different regions on the surface of DIII. The residue numbering corresponds to the sequence for protein E of DV serotype 2, strain Jamaica 1409, available from the Swiss-Prot databank with access number P07564. The underlined residues are not present in protein E and were introduced during design. The cysteine residues are used to restrict the structural mobility of the peptide by a disulphide bridge. (B) Recognition of the HDIII2Cs peptide by the neutralizing antibody 3H5 in a Western blotting assay. 50 μg of the BSA-peptide conjugates and 20 μg of the recombinant protein PD5 were electrophoresed on a 12.5% SDS-PAGE gel and transferred to a nitrocellulose membrane. After blocking, the membrane was incubated with a dilution (30 μg/mL) of the 3H5 mAb for 2 hours at 25° C. The bound antibody was detected with an anti-mouse IgG-peroxidase conjugate, and the blots were developed using chemiluminescence. (C) Two pieces of nitrocellulose membrane were sensitized in parallel with 10 μg of each variant of the protein and of the peptides. One membrane was incubated with mAb 3H5 at a concentration of 30 ng/mL, and the second was incubated with pooled sera from mice immunized with an HDIII2Cs-KLH conjugate. The detection of the bound antibodies was performed in the same conditions used for the Western blotting assay. RCM: reduced and carbamidomethylated protein/peptide.

Figure 13:
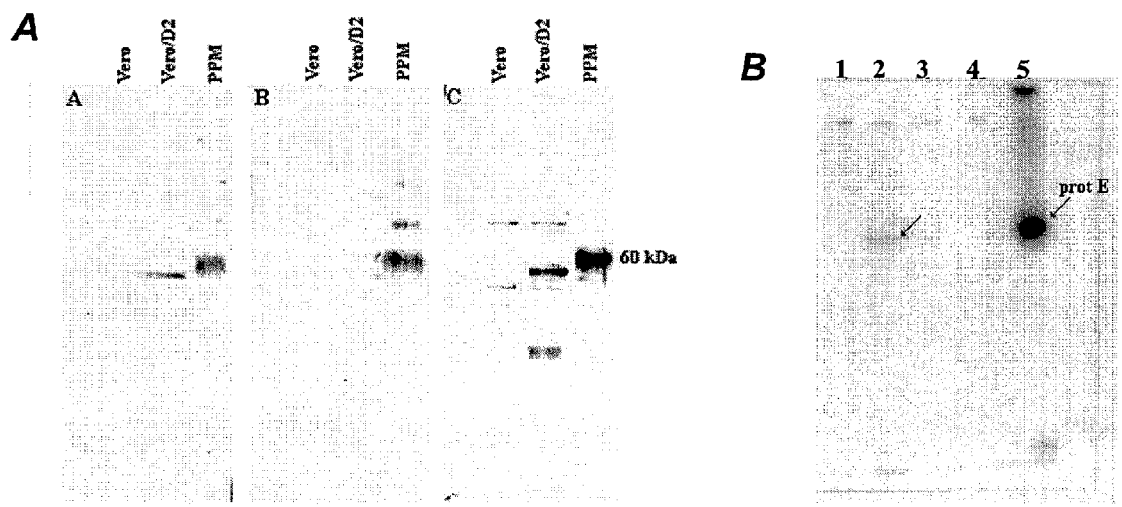

FIG. 13. Recognition of the virus by the anti-HDIIIE2Cs serum. (A) Homogenates of Vero cells, infected with DV2 or uninfected, were electrophoresed by 10% SDS-PAGE and transferred to a nitrocellulose membrane. After blocking, the membranes were incubated with the following antibody preparations: (A.A) mAb 3H5 at 30 μg/mL, (A.B) Preimmune sera from the mice immunized with the HDIIIE2Cs-KLH conjugate, diluted 1/100 and (A.C) Sera from mice immunized with five doses of the HDIIIE2Cs-KLH conjugate, diluted 1/100. (B) Immunoprecipitation of $^{35}S\_DV2$ with sera from mice immunized with different DIII peptides. A 1/100 dilution of the pooled sera from mice immunized with the peptide-KLH conjugates (After the fifth dose) was used. Lane 1. anti-pepDIII-1 sera. Lane 2. anti-HDIIIE2Cs sera. Lane 3. anti-pepDIII-2 sera. Lane 4. Immunoprecipitation buffer, without sample, and Lane 5. Pooled human sera reactive with DV2.

Figure 14:
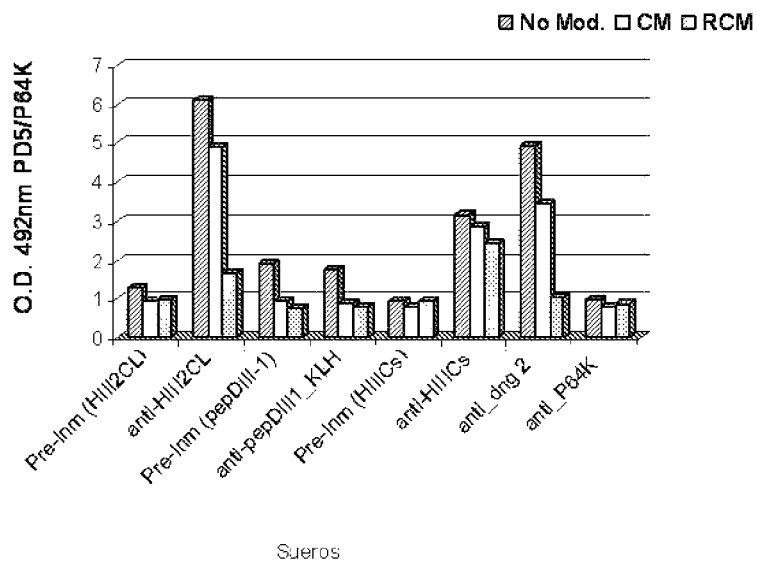

FIG. 14. Recognition of the PD5 protein by the sera obtained from mice immunized with peptide-KLH conjugates. Multiwell plates were coated with 0.5 pg/well of total protein from the different variants: unmodified (unmod.), reduced and carbamidomethylated (RCM) and carbamidomethylated without previous reduction of its disulphide bridges (CM). Pooled sera from each group, diluted 1:100, were incubated for 2 hours at 37° C. in PBS-T pH 7.4. Both assays were developed with an anti-mouse IgG-HRP conjugate (diluted 1:1000), using $H_2O_2$/OPD as substrates for the peroxidase. The enzymatic reaction was stopped after 20 min. by the addition of 2.5 Mol/L $H_2SO_4$, and the absorbance was measured at 492 nm. The data about the sequence of the peptides and the region of DIII from DV that they comprise can be found on FIGS. 9 and 11.

Figure 15:
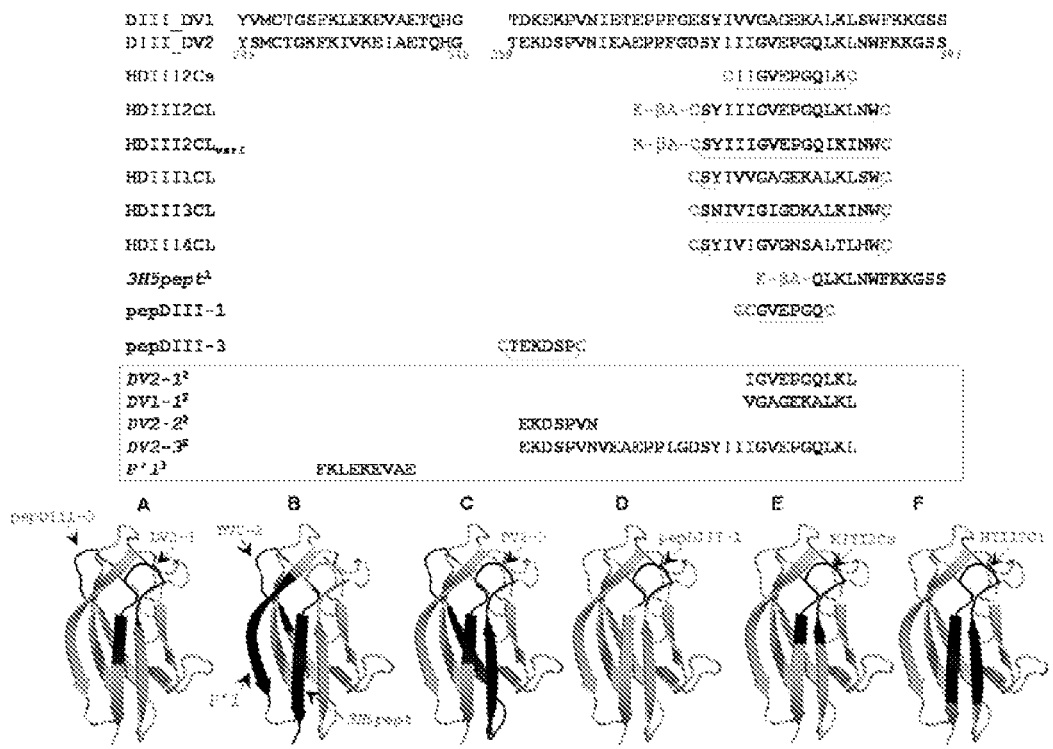
Figure 15:
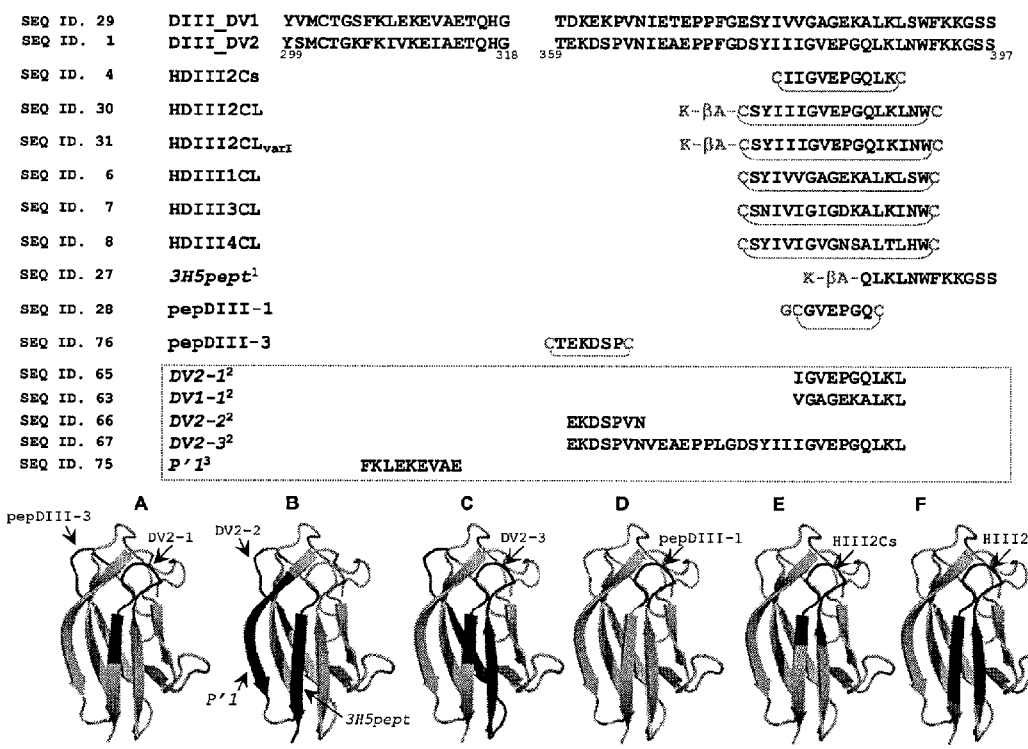

FIG. 15. Representation of the region of DIII from protein E of DV included in the designed peptides. The represented sequences are those corresponding to aminoacids 299-318 and 359-397 (sequence numbering from DV2) of DIII from DV1 (DIII_DV1) and DV2 (DIII_DV2). 3H5pept is a peptide reported in the literature as part of the epitope recognized by mAb 3H5 (Trirawatanapong T, Chandran B, Putnak R, Padmanabhan R (1992) *Mapping of a region of dengue virus type-2 glycoprotein required for binding by a neutralizing monoclonal antibody. Gene.* 116:139-50). Additional aminoacids, not present in the original sequence but introduced during design, are represented in gray. Two cysteine residues were used for introducing a disulphide bridge that would restrict the conformational freedom of the peptide. The N-terminal lysine was introduced for allowing the covalent conjugation of the peptides to carrier proteins, and the β-alanine residue was included as a spacer. Included in the grayed box are the sequences of linear peptides used in precedent reports in the literature, DV2-1, DV1-1, DV2-2, DV2-3 (Hung J J, Hsieh M T, Young M J, Kao C L, King C C, Chang W (2004) *An external loop region of domain III of dengue virus type 2 envelope protein is involved in serotype-specific binding to mosquito but not mammalian cells. J Virol.* 78:378-88) and P'1 (Thullier P, Demangel C, Bedouelle H, Megret F, Jouan A, Deubel V, Mazie J C, Lafaye P (2001) *Mapping of a dengue virus neutralizing epitope critical for the infectivity of all serotypes: insight into the neutralization mechanism J Gen Virol.* 82(Pt 8):1885-92). A three-dimensional representation of the region spanned by the peptides (highlighted in black) on the structure of DIII is found at the bottom of the picture.

Figure 16:
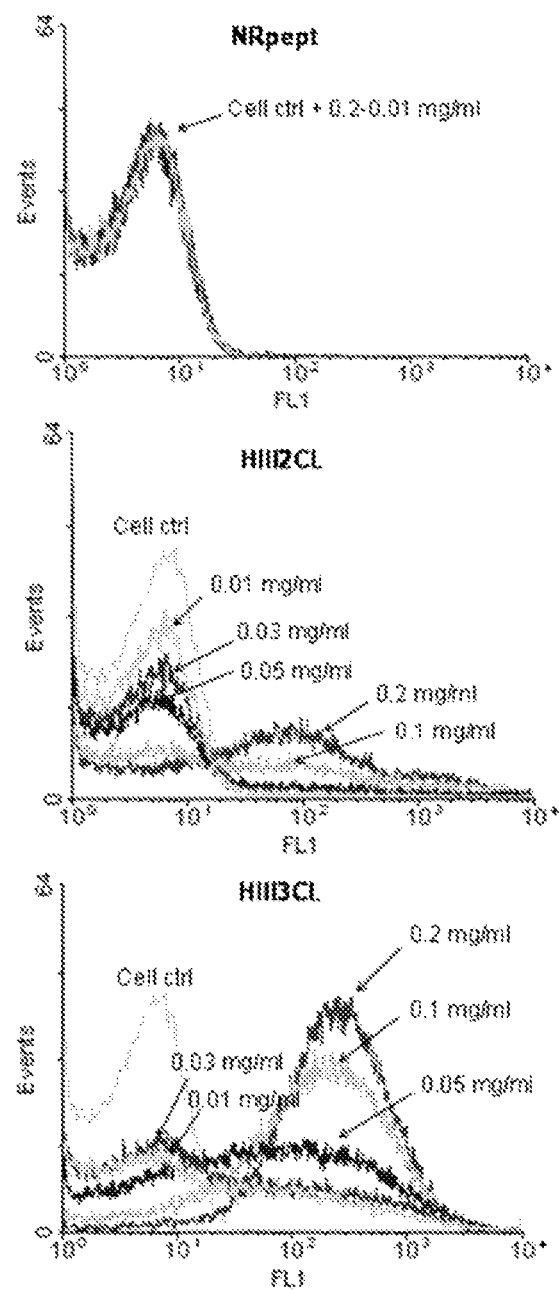

FIG. 16. Binding of peptides HDIII2CL (SEQ ID. 5) and HDIII3CL (SEQ ID. 7) to the surface of white cells from peripheral human blood. The cells, isolated by erythrocyte lysis, were washed with PBS pH 7.4, 1% bovine serum albumin (BSA), 0.01% $NaN_3$, 1 mM $CaCl_2$, 1 mM $MgCl_2$ and fixed with 1% paraformaldehyde in PBS pH 7.4. After washing, the cells were incubated with the peptide dilutions for 30 min. at 4° C. in PBS pH 7.4, 1% BSA. Binding of the peptides was detected with a streptavidin-FITC conjugate, using flow cytometry. Cell control: Fixed cells not treated with peptide or conjugate.

Figures 17, 18:
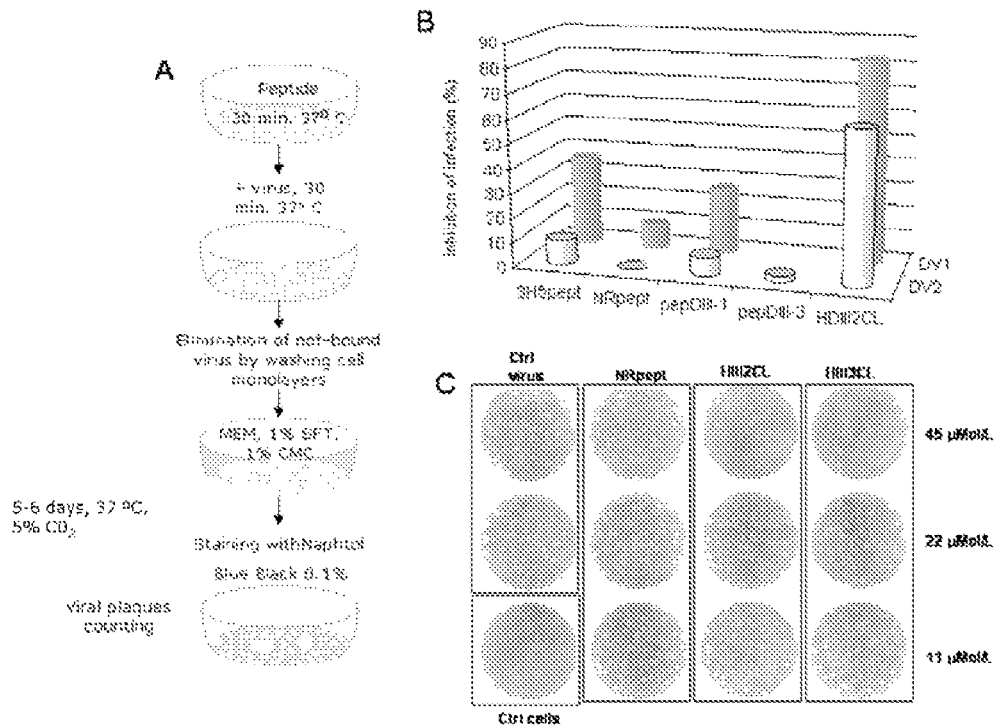

FIG. 17. Inhibition of the infection of Vero cells with DV1 and DV2. (A) Six-well plates with a monolayer at approximately 90% confluence were incubated for 30 min. at 37° C. with dilutions of the peptides in MEM medium. A dilution of either DV1 strain West Pac 74 or DV2 strain S16803 was then added, calculated so as to obtain an average of 100 lytic plaques per well, and the plates were incubated for 30 min. at 37° C. with the virus/peptide mixture. After the incubation the cells were washed twice, received the addition of MEM medium supplemented with non-essential amino acids, 1% fetal calf serum, 1% CMC, and finally were incubated for 5 days at 37° C. under a CO2 atmosphere. (B) Inhibitory effect of the peptides at 100 μMol/L. NRpep: Non-related peptide. Data on the sequence of the peptides 3H5pept (SEQ ID. 27), pepDIII-1 (SEQ ID. 28), HIII2CL (SEQ ID. 5) and HIII3CL (SEQ ID. 7), as well as on the region they span on DIII from DV, can be obtained from FIG. 11. The calculation of the inhibition percentages is described in Materials and Methods. (C) Inhibition of DV2 infection by using varying peptide concentrations. The viral plaques were visualized by staining with Naphtol Blue Black. Cell control: Untreated cells. Virus control: Cells incubated with the virus, but without peptide. For both peptides a 50% inhibition is obtained at concentrations from 22 to 45 μMol/L.

FIG. 18. Multiple sequence alignment of the residues corresponding to the FG beta hairpin from FV of interest for human and animal health. (YFV) Yellow Fever Virus, (WNV) West Nile Virus, (JAE) Japanese Encephalitis virus, (TBE) Tick-Borne Encephalitis virus, (KUNJ) Kunjin virus, (POW) Powasan virus, (LAN) Langat virus, (MVE) Murray Valley Encephalitis virus and (SLE) Saint Louis Encephalitis virus.

FIG. 19. Effect produced on the binding of A2M and RAPR13 to the surface of Vero cells by simultaneous incubation with the peptides. The fluoresceinated A2M and RAP13 proteins were incubated for 30 min. at 4° C. with pre-fixed Vero cells in the presence of varying concentrations of HIII2CL and 3H5pept in order to reach the indicated molar peptide/protein ratios. The binding of the labeled ligands was detected by flow cytometry.

FIG. 20. Inhibition of the infection of Vero cells with DV by pre-incubation with A2M. Viral preparations were incubated 1 h at 25° C. (A and C) or the indicated time (B) with the proteins i. e. activated A2M (A2Mact), non-activated A2M (A2M no act) and a non-related protein (NR). The mixtures of the proteins with the virus were added to monolayers of Vero cells and incubated for 1 h at 37° C. The cell monolayers were washed to eliminate non-bound virus. Next, medium MEM supplemented with non-essential amino acids and 1% FBS, 1% CMC was added and the cells were incubated for 5 days at 37° C. in a $CO_2$ incubator. To visualize the viral plaques, Vero cells were stained using Naphtol Blue Black. All experimental points were performed on duplicates.

FIG. 21. Chromatographic profile of the purification of the A2MR using affinity chormatography with immobilized A2M (A) and SDS-PAGE analysis of fractions eluted using a 5-15% gradient gel (B). Effect of the pre-incubation of chromatography fractions with DV2 on the infection of Vero cells (C). The plaque reduction neutralization assay was performed as described in FIG. 20. (D) Mice protection assay using the DV-induced encephalitis model.

FIG. 22. Mice protection assay using the DV-induced encephalitis model. PepNR GAGs binding: peptide formed by a sequence fragment of binding to glycosaminoglycans and a non-related sequence fragment.

EXAMPLES

Materials and Methods

Denaturing Protein Electrophoresis (SDS-PAGE)

Polyacrylamide gels were used according to the standard conditions described by Laemmli (Laemmli, U. K., (1970). *Cleavage of structural proteins during the assembly of the head of bacteriophage T*4. *Nature* 227: 680-685). The protein samples were diluted in sample buffer (1% SDS, 0.3 M Tris-HCl, pH 6.8). For analysis under reducing conditions the same procedure was followed, but adding β-mercaptoethanol to a final concentration of 2 mM to the sample buffer, and heating the samples for 2 min. at 95° C. The electrophoretic runs were performed at 20 mA in 0.25 M Tris-HCl, 1.92 M glycine buffer, pH 8.3 and 1% SDS. The standard methodologies for staining with Coomassie blue or silver were employed. The gels intended for the electrophoretic separation of proteins to be later analyzed by mass spectrometry were stained following the procedure for silver staining without glutaraldehyde, which is downstream-compatible with this technique (Shevchenko, A., Willm, M., Vorm, O. y Mann, M., (1996). *Anal. Chem.* 68: 850-858).

Western Blotting

The proteins, once separated by electrophoresis, were transferred from the gel to 0.45 μm Hybond-ECL nitrocellulose membranes (Amersham, UK) in an underwater transfer cell (Towbin H., Staehelin T. and Golden J. (1979). *Electroforetic transfer of protein from polyacrylamide gel to nitrocellulose sheets: procedure and some applications. Proc. Natl. Acad. Sci.* 76: 4350-4354). After transfer the membranes were blocked with 5% (w/v) skimmed milk in PBS pH 7.4, 0.1% Tween-20 by incubation for 1 hour at 25° C., under constant shaking. Afterwards, they were incubated overnight at 4° C. with the corresponding antibody diluted in PBS pH 7.4, 0.1% Tween-20, 5% skimmed milk. After rinsing with plenty of PBS pH 7.4, 0.1% Tween-20, the membrane was then incubated for 1 h at 25° C. with the proper peroxidase conjugate, depending on the species from which the antibodies had been obtained. The conjugates in all cases were obtained either from Amersham (UK) or Sigma (USA). The peroxidase substrate used for visualizing the reactive species is indicated in the respective figure captions.

Dot Blotting

Two pieces of nitrocellulose membrane were sensitized with equimolar amounts of DIIIE2J and BSA for 1 hour at 25° C. Both membranes included, as a control for the anti-virus reactivity of the antibodies, a preparation of viral antigen from DV serotype 2 with its corresponding negative control. The membranes were blocked for 1 hour, under constant shaking, at 25° C. in PBS, 0.1% Tween-20 containing 5% skimmed milk. The incubation with the different antibody preparations was performed in PBS, 0.01% Tween-20, 5% skimmed milk for 2 h at 25° C. At the end of the incubation the membranes were washed extensively with PBS, 0.01% Tween-20 and incubated with an anti-mouse IgG-peroxidase conjugate (Amersham, UK) in the case of murine antibodies, or an anti-human IgG-peroxidase conjugate (Sigma, USA) for those of human origin, during 1 h at 25° C. in both cases. After washing extensively the membrane for a second time, the membranes were developed using the ECL Western Blotting Analysis System (Amersham, UK) with CP-G PLUS (AGFA, Belgium) film in an FBXC 810 autoradiography cassette (Fisher Biotech, USA). The films were developed in an automatic processor for autoradiographic films (Hyperprocessor, Amersham, UK).

Protein Immobilization into Chromatographic Gels

A 10 mg aliquot of purified protein was dialyzed against 0.1 Mol/L $NaHCO_3$ pH 8.3, 0.5 Mol/L NaCl. Coupling of the protein to a chromatographic gel was achieved by incubation with 1 mL of CNBr-activated Sepharose (Amersham, UK) for 2 hours at 25° C. The uncoupled protein was removed from the gel by centrifugation at 500×g for 5 min. The coupling efficiency was estimated by comparison of the protein concentration of the solution before and after the reaction. In all cases, approximately 95% of the protein was immobilized.

Assay for Protein Concentration

The assays for the determination of protein concentration were carried out using a bicinchoninic acid-based kit (Pierce, USA), following the instructions of the manufacturer for assays in 96-well plates. The standard curve was prepared with different dilutions (0.025-2 mg/mL) of bovine serum albumin (BSA) (Sigma, USA).

Covalent Immobilization onto cm5 Chips

A cm5 chip (Biacore, Sweden) was used for the covalent immobilization of the DIIIE2J and LRP1 proteins. The immobilization was carried out at 25° C., with a flow of 5 µL/min and using HBS (Biacore, Sweden) as running buffer. The surface of the chip was activated by loading 35 µL of 0.2 Mol/L N-ethyl-N'-(3-diethylamino-propyl)carbodiimide (EDC) and 0.05 Mol/L N-hydroxysuccinimide (NHS). Afterwards the proteins, dissolved in 10 mM sodium acetate buffer pH 4.5, were loaded into the system. At the end of the immobilization, 35 µL of 1 M ethanolamine pH 8 were loaded into the system in order to block any remaining free activated groups. The channel to be used as a negative control in each case received only the activating injections with the EDC: NHS solution and the blocking with ethanolamine, employing the same flow and injection volume. The results were analyzed using the BIAevaluation ver. 4.1 software application package (Biacore, Sweden).

Analysis by Mass Spectrometry

The mass spectra were acquired with a hybrid mass spectrometer with octagonal geometry QTOF-2TM (Micromass, UK), equipped with a Z-spray electronebulization ionization source.

The software used for the acquisition and processing of the spectra was MassLinx, ver. 3.5 (Waters, USA). The ESI-MS spectrum of the mixture of tryptic peptides was deconvoluted using MaxEntropy ver. 3.0 (Micromass, UK). The identification software applications employed were MASCOT and SeqTag.

Obtention of DIII from Protein E of DV2 Genotype Jamaica (DIIIE2J)

Domain III from the E protein of DV2 was obtained by recombinant DNA techniques, expressing in the bacterium *Escherichia coli* a gene fragment coding for this polypeptide. For this goal, two oligonucleotides with the sequences CATATGGCCATGGACAAACTACAGCTC (SEQ ID. 19) and CTCGAGGCCGATGGAACTTCCTTT (SEQ ID. 20), carrying in their 5' ends the recognition sequences for the restriction enzymes Nde I and Xho I respectively (in bold in the sequences), were synthesized using the phosphoramidite method (Beaucage S L, Caruthers M H, *Deoxynucleoside phosphoramidites—A new class of key intermediates for deoxypolynucleotide synthesis., Tetrahedron Letters*, (1981), 22, 1859).

With this oligonucleotides, and using as a template the p30-VD2 plasmid (Deubel V, Kinney R M, Trent D W, *Nucleotide sequence and deduced amino acid sequence of the structural proteins of dengue type* 2 *virus, Jamaica genotype. Virology*, (1986), 155, 365) containing the first 2469 nucleotides from the genome of the Jamaica 1409 strain of DV2, a DNA fragment coding for DIII of the E protein was amplified by PCR (Saiki R K, Scharf S, Faloona F, Mullis K B, Horn G T, Erlich H A, Arnheim N, *Enzymatic amplification of beta-globin genomic sequences and restriction site analysis for diagnosis of sickle cell anemia. Science* (1985), 230, 1350). This fragment was cloned into the pMOSBlue vector using the pMOSBlue blunt-ended cloning kit from Amersham, UK (RPN 5110), and then purified by digestion of the resulting plasmid with the enzymes Nde I and Xho I (Promega Benelux, b.v., The Netherlands) according to the instructions of the manufacturer, followed by electrophoresis on low melting temperature agarose gels (Sambrook, J.; Fritsch, E. F.; Maniatis, T. *Molecular Cloning: A Laboratory Manual* (1989), Cold Spring Harbor Laboratory Press, New York, USA). This fragment was then ligated to the pET22b+ plasmid (Novagen Inc., USA) digested identically, using T4 DNA ligase (Promega Benelux, b.v., The Netherlands) under the conditions specified by the manufacturer.

The obtained mixtures were transformed into the *E. coli* strain XL-1 Blue (Bullock W O, Fernández J M, Short J M. *XL-1Blue: A high efficiency plasmid transforming recA Escherichia coli K*12 *strain with beta-galactosidase selection. Biotechniques* 1987; 5:376-8) according to Sambrook et al. (Sambrook J, Fritsch EF, Maniatis T. *Molecular cloning: A laboratory manual*. New York, USA: Cold Spring Harbor Laboratory Press; 1989), and the resulting plasmids present in the colonies obtained after growth in selective medium were screened by restriction analysis. The sequence of several recombinant plasmids was verified by automatic Sanger sequencing, and a representative molecule whose sequence matched the expected sequence was chosen and denominated pET-iDIIIE2_J (SEQ ID. 21). This plasmid codes for the intracellular synthesis, in *E. coli*, of DIII from protein E of DV serotype 2, strain Jamaica 1409, under control of the T7 promoter. The obtained protein, denominated DIIIE2J (SEQ ID. 22), contains a sequence of 6 consecutive histidines at its C-terminus, introduced as a tag for facilitating its purification by immobilized metal affinity chromatography (IMAC) (Sulkowski, E. (1985) *Purification of proteins by IMAC. Trends Biotechnol.* 3, 1-7).

In order to purify DIIIE2J, the pET-iDIIIE2_J plasmid was transformed (Sambrook J, Fritsch E F, Maniatis T. *Molecular cloning: A laboratory manual*. New York, USA: Cold Spring Harbor Laboratory Press; 1989) into the BL21(DE3) *E. coli* strain (Studier, F. W and B. A. Moffatt. "*Use of bacteriophage T7 RNA polymerase to direct selective high-level expression of cloned genes.*" *J. Mol. Biol.* 189.1 (1986): 113-30), and a well-isolated colony was used to inoculate a 50 mL Luria Bertani culture supplemented with 50 μg/mL ampicillin (LBA). The culture was grown for 12 hours at 30° C. at 350 r.p.m. and then used to inoculate 1 L of LBA medium at a starting optical density of 0.05 at 620 nm, which was then grown for 8 h at 28° C. until the late exponential phase and induced by the addition of isopropylthiogalactoside (IPTG). Growth was resumed under the same conditions for 5 further hours.

The induced culture was centrifuged at 5000×g for 30 min. at 4° C. and the resulting biomass was resuspended in 30 mL of PBS and ruptured using 3 cycles on a French press at 1500 $kg/cm^2$. After centrifugation of the homogenate at 10 000×g for 30 min. at 4° C. the pellet, containing the protein as inclusion bodies, was solubilized in 30 mL of PBS, 6 M guanidinium hydrochloride and DIIIE2J was refolded by dilution into PBS/10 mM imidazole at a final protein concentration of 100 μg/mL.

The refolded DIIIE2J was purified by immobilized metal affinity chromatography (Sulkowski, E. (1985) *Purification of proteins by IMAC. Trends Biotechnol.* 3, 1-7) using Ni-NTA agarose (Qiagen Benelux B. V., The Netherlands). After binding, the protein was eluted by successively washing the column with 50,100 and 300 mMol/L solutions of imidazole in PBS pH 7.4, 0.3 Mol/L NaCl as buffer. The obtained protein has a purity higher to or equal to 90% as assessed by the analysis of digital scans of Coomassie Blue-stained SDS-PAGE gels run under denaturing conditions, using the densitometric routines of the ImageJ ver. 1.35d software application (Rasband W, http://rsb.info.nih.gov/ij/).

Purification of Human A2M

Human A2M was purified from 380 mL of human plasma, obtained by pooling plasma samples from healthy donors who were 30 to 40 years old. The plasma was dialyzed against deionized water with frequent changes for 72 hours at 4° C., the insoluble material was pelleted by centrifugation at 10000×g for 30 min, and the supernatant was dialyzed against PBS pH 6 and loaded into an XK 50/30 column (Amersham, UK) packed with 65 mL of Chelating Sepharose Fast Flow (Amersham, UK) previously loaded with $Zn^{2+}$ and equilibrated with PBS pH 6. The column was then washed with PBS pH 6 until the absorbance of the eluate at 280 nm decreased to baseline levels, and the bound protein was eluted with 10 mMol/L sodium acetate buffer pH 5, 150 mM NaCl. The eluted protein was concentrated by ultrafiltration using a membrane with a MWCO of 300 kDa and then loaded at a flow of 2 mL/min into a gel filtration column (26×51 cm) packed with Superdex 200 (Amersham, UK) and equilibrated with PBS pH 7.8. The presence of the protein in the fraction with the highest molecular weight was checked by a western blotting assay, using a polyclonal anti-human A2M antibody preparation (Sigma, USA). The activation of the purified A2M was achieved by incubation with 200 mMol/L of methylamine in 50 mMol/L sodium phosphate, 150 mMol/L NaCl, pH 7.4. The obtained $A2M\_MeNH_2$ was dialyzed extensively against 50 mMol/L sodium phosphate, 0.5 Mol/L NaCl pH 7.8.

Obtention of the Recombinant Human LRPAP1 (RAP) Protein

The human protein associated to the LRP1 receptor, known as LRPAP1 or, more commonly in the scientific literature, as RAP, was obtained by recombinant DNA techniques, expressing in the bacterium Escherichia coli a gene fragment coding for this molecule. For this goal, total RNA was purified from the human monocytic cell line THP-1 (Tsuchiya, S.; Yamabe, M.; Yamaguchi, Y.; Kobayashi, Y.; Konno, T.; Tada, K. (1980) Establishment and characterization of a human acute monocytic leukemia cell line (THP-1), Int. J. Cancer 26(2):171) using the protocol described by Chomczynsky and Sacchi (Chomczynski, P.; Sacchi, N. (1987) Single-step method of RNA isolation by acid guanidinium thiocyanate-phenol-chloroform extraction. Analytical Biochemistry 162 (1):156); and this RNA was reverse-transcribed into cDNA with the GeneAmp RNA PCR Core Kit from Perkin-Elmer (USA, N808-0143), using random hexamers. The gene for the LRPAP1 (RAP) protein was amplified from the cDNA by PCR (Saiki, R. K.; Scharf, S.; Faloona, F.; Mullis, K. B.; Horn, G. T.; Erlich, H. A.; Arnheim, N. (1985) Enzymatic amplification of beta-globin genomic sequences and restriction site analysis for diagnosis of sickle cell anemia. Science 230(4732):1350), using the GeneAmp RNA PCR Core Kit (Perkin-Elmer, USA, N808-0143) and the oligonucleotides CATATGTACTCGCGGGAGAAGAACCAG (SEQ ID. 23) and CTCGAGTCAGAGTTCGTTGTGC (SEQ ID. 24), bearing on their 5' end the recognition sequence for the restriction enzymes Nde I and Xho I, respectively (in boldface in the sequence), which had been previously synthesized by phosphoramidite chemistry (Beaucage S L, Caruthers M H, Deoxynucleoside phosphoramidites—A new class of key intermediates for deoxypolynucleotide synthesis., Tetrahedron Letters, (1981), 22, 1859).

The amplified fragment was cloned into the pGEM-T vector (Promega Benelux b.v., The Netherlands) using the pGEM-T Vector System I Kit (Promega Benelux b.v., The Netherlands, A3600), and isolated later by digestion with Nde I and Xho I (Promega Benelux, b.v., The Netherlands) under the conditions specified by the manufacturer, followed by electrophoresis on low melting temperature agarose gels (Sambrook, J.; Fritsch, E. F.; Maniatis, T. Molecular Cloning: A Laboratory Manual (1989), Cold Spring Harbor Laboratory Press, New York, USA). This fragment was then ligated to the pET28a+ plasmid (Novagen Inc., USA), previously digested with Nde I and Xho I, using T4 DNA ligase (Promega Benelux, b.v., The Netherlands) under the conditions specified by the manufacturer. The reaction mixtures were transformed into the Escherichia coli strain XL-1 Blue (Bullock W O, Fernández J M, Short J M. XL-1Blue: A high efficiency plasmid transforming recA Escherichia coli K12 strain with beta-galactosidase selection. Biotechniques 1987; 5:376-8) according to Sambrook et al. (Sambrook J, Fritsch E F, Maniatis T. Molecular cloning: A laboratory manual. New York, USA: Cold Spring Harbor Laboratory Press; 1989) and the plasmids from the colonies obtained after growth in selective medium were screened by restriction analysis. The sequences from several of the resulting recombinant plasmids were verified by automated Sanger sequencing, and a representative clone matching the expected sequence was chosen and denominated pET-RAP (SEQ. ID. 25). This plasmid codes for the intracellular synthesis, in E. coli, of the human protein LRPAP1 (RAP) under control of the T7 promoter. The recombinant protein, denominated RAPR13 (SEQ ID. 26), contains a tag of 6 consecutive histidines at the N-terminus for its later purification through immobilized metal affinity chromatography (IMAC) (Sulkowski, E. (1985) Purification of proteins by IMAC. Trends Biotechnol. 3, 1-7), separated from the remainder of the protein by a thrombin cleavage site.

The purification of RAPR13 was achieved by transforming the pET-RAP plasmid (Sam brook J, Fritsch E F, Maniatis T. Molecular cloning: A laboratory manual. New York, USA: Cold Spring Harbor Laboratory Press; 1989) into the E. coli strain BL21(DE3) (Studier, F. W. and B. A. Moffatt. "Use of bacteriophage T7 RNA polymerase to direct selective high-level expression of cloned genes." J.Mol.Biol. 189.1 (1986): 113-30) and inoculating, from a well isolated colony, a 50 mL culture of ZYM5052 medium (Studier,F. W (2005) Protein production by auto-induction in high density shaking cultures. Protein Expression and Purification 41(1):207) supplemented with kanamycin at 100 µg/mL in a 1 L Erlenmeyer flask which was then incubated for 16 hours at 28° C. and 350 r.p.m. The induced culture was centrifuged at 5000×g for 30 min. at 4° C., and the resulting biomass was resuspended in 30 mL of PBS and ruptured by 3 passes on a French press at 1500 kg/cm². After centrifugation of the resulting homogenate at 10 000×g for 30 min. at 4° C., the protein was purified from the supernatant by immobilized metal affinity chromatography (Sulkowski, E. (1985) Purification of proteins by IMAC. Trends Biotechnol. 3, 1-7) using Ni-NTA agarose (Qiagen Benelux B. V., The Netherlands), with a linear gradient of 10 to 300 mM imidazole in PBS/0.3 M NaCl as running buffer for the elution. The purified protein has a purity equal to or higher than 90%, as estimated by analyzing digital scans of Coomassie Blue-stained denaturing polyacrylamide electrophoresis gels (SDS-PAGE) of the samples, using the densitometric routines of the ImageJ ver. 1.35d software application package (Rasband W.)

Peptide Synthesis

The peptides were obtained by solid phase synthesis on an Fmoc-AM-MBHA resin, using the Fmoc/tBu strategy (Barany, G. and Merrifield, R. B. J Am Chem Soc. 99 (1977) 7363-7365). The aminoacids were coupled by activation with DIC/HOBt, monitoring the completion of the coupling reaction by the ninhydrin assay (Kaiser, E., Colescott, R. L., Bossinger, C. D., Cook, P. I. *Anal Biochem.* 34 (1970) 595-598). The synthesized peptides were detached from the resin by treatment with a solution of TFA/EDT/$H_2O$/TIS (94%/2.5%/2.5%/1%), precipitated with ether, and lyophilized during 72 h. Peptide cyclization by forming a disulphide bridge was achieved by oxidation with DMSO (Andreu, D., Albericio, F., Solé, N. A., Munson, M. C., Ferrer, M. and Barany, G., Pennington, M. W and Dunn, B. M. (Eds), *Peptide Synthesis Protocols, Methods in Molecular Biology*, Totowa, N.J., 1994, pp. 91-169). In all cases, the peptides were purified by RP-HPLC and the collected fractions were analyzed again by analytical RP-HPLC. The final preparation of each peptide was obtained by pooling the fractions with a chromatographic purity equal to or higher than 99%. The mass of the peptide on each final preparation was verified by ESI-MS mass spectrometry.

Assay for the Binding of Fluoresceinated Proteins to the Cellular Surface

Mononuclear peripheral blood cells were obtained by erythrocyte lysis of total blood samples from healthy donors, which had been obtained by venipuncture into BD Vacutainer $K_3$ EDTA vials. The lysis solution (0.3 Mol/L $NH_4Cl$, 20 mMol/L $KHCO_3$, 20 μMol/L $Na_2EDTA$) was added to the blood, using 2 ml per each 100 μl of blood, and the samples were then incubated approximately for 15 min. at 25° C., shaking the samples at 3-min. intervals. The reaction was stopped by chilling to 4° C., and the cells were separated from the lysis solution by centrifugation at 350×g for 5 min. After eliminating the supernatant, the cells were washed with PBS pH 7.4, 1% bovine serum albumin (BSA), 0.01% $NaN_3$, 1 mM $CaCl_2$, 1 mM $MgCl_2$.

In the case of cultured Vero cells, they were detached from the surface of the culture flask without using proteases, by incubation with PBS pH 7.4, 5 mM EDTA for 10 min. at 37° C., gently tapping the outside of the flask.

The cells, collected and washed as described above, were incubated in fixing solution (PBS pH 7.4, 2% paraformaldehyde, 0.01% $NaN_3$, 1 mM $CaCl_2$, 1 mM $MgCl_2$ for 30 min at 4° C., and the fixing solution was then eliminated by centrifugation at 350×g for 5 min a 4° C. The assay was carried out by incubating $1\times10^5$ cells during 1 hour at 4° C. in a total volume of 100 μL of each dilution of the fluoresceinated proteins (the dilutions were made in PBS pH 7.4, 1% BSA, 1 mM $CaCl_2$, 1 mM $MgCl_2$). Each experiment included controls with untreated cells. After the incubation, the cells were washed twice and incubated again in fixing solution. The intensity of the fluorescence was quantified by flow cytometry on a PAS III cytometer (Partec, Germany). The values for each experimental point were calculated from measurements on a minimum of 20 000 cells.

Inhibition of Viral Infection in Vero Cells

Vero cells were grown in 24-well plates to approximately 90% confluence, and washed twice with MEM medium without FCS. The dilutions containing the proteins or the antibodies, according to the objective of the assay, were then added and incubated for 1 hour at 37° C. After the incubation, the virus was added at a multiplicity of infection of 0.1, followed by a subsequent incubation for 1 hour at 37° C. At the end of the second incubation, the unbound virus was eliminated by washing, and the cells were incubated for 5 days at 37° C. in high density medium (MEM supplemented with non essential aminoacids, 1% FCS, 1% carboxymethylcellulose) in order to propitiate the appearance of lytic plaques. The plaques were visualized by staining with 0.1% Naphtol Blue Black in 0.15 Mol/L sodium acetate. Two replicates were used per experimental point in each assay, and three independent determinations were performed. The inhibition percentage was calculated according to the expression $$100\times\left[1-\frac{\text{No. plaques}}{\text{No. plaques Virus Cntrl.}}\right].$$

Assay of Protection of Mice Using the DV-induced Encephalitis Model.

Groups of 12 adult Balb/C mice (20 g average body weight) were anesthesized, inoculated by intracranial injection with lethal dosis of DV2 and observed daily for 21 days. The mixtures of peptides with the virus were inoculated in the same way. The volume of the sample inoculated was 20 μL.

Example 1

Figure 3:
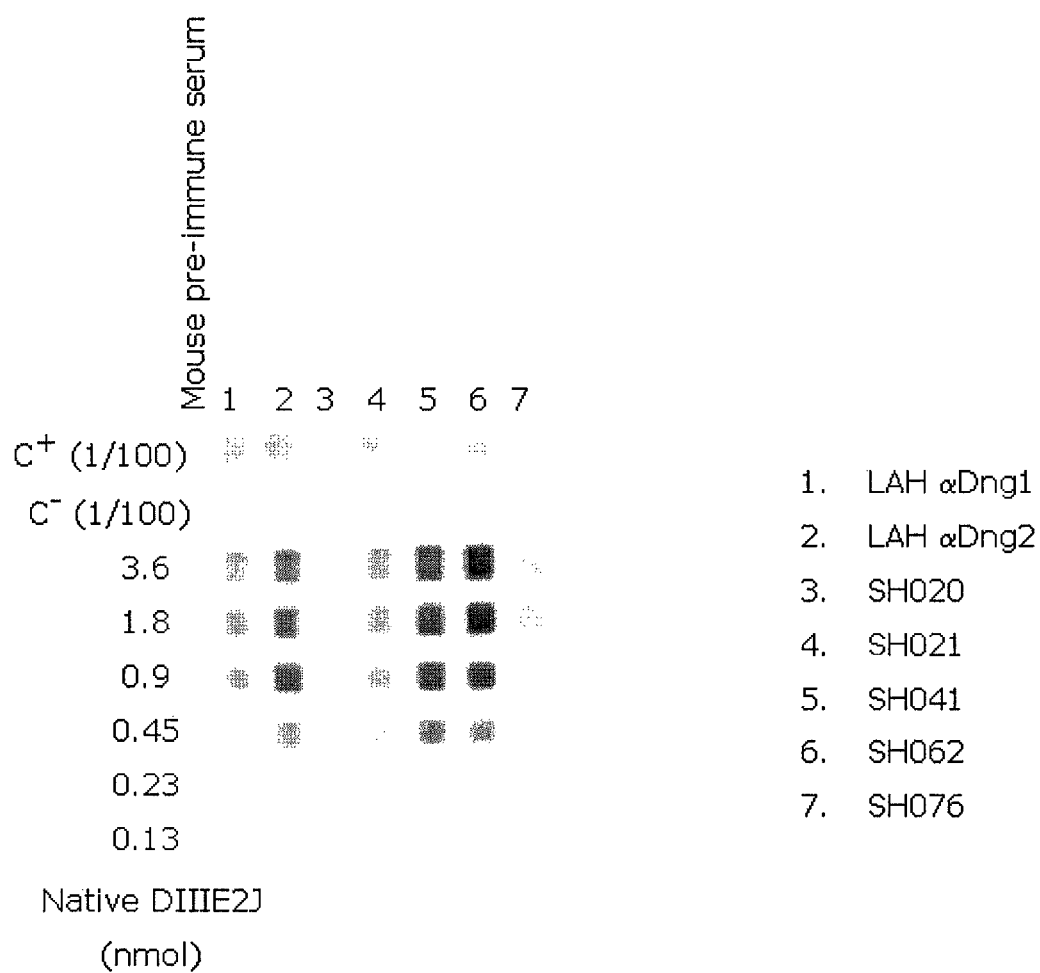
Figure 3:
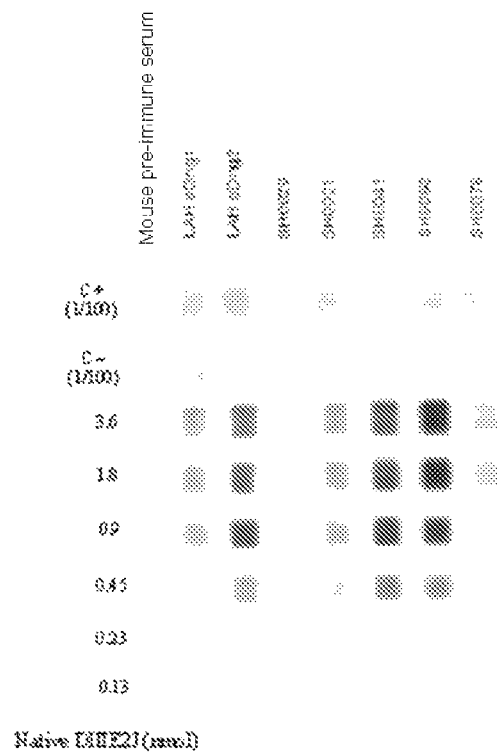

Obtention of an Affinity Matrix for the Isolation of Proteins that Bind DIII from DV With the aim of preparing an affinity matrix with DIII as a ligand for the isolation of human plasma proteins as potential receptors for DV, the recombinant protein DIIIE2J, comprising residues $Met_{289}$ to $Gly_{400}$ (SEQ ID. No. 22) of protein E from DV2, was cloned and expressed in *E. coli.*

After IMAC, the obtained preparation has a high purity as assessed by protein electrophoresis, where silver staining only reveals a major band without detectable contaminants (FIG. 1B). In order to discard the possible presence of contaminants which might comigrate with DIIIE2J during electrophoresis, the preparation was analyzed by reversed-phase chromatography (rp-HPLC). An aliquot of 80 μg of DIIIE2J was loaded into a C4 reversed phase 4.6×250 mm column (J. T. Baker, USA). The obtained chromatogram (FIG. 1A) has only a single peak, confirming the high degree of homogeneity of the preparation.

DIII has a large number of topographical epitopes recognized by neutralizing antibodies, and in all these cases it has been shown that antibody recognition is abolished upon reduction of the disulphide bridge between the two cysteines of DIII. (Roehrig J T, Bolin R A, Kelly R G (1998) *Monoclonal antibody mapping of the envelope glycoprotein of the dengue* 2 virus, Jamaica Virology 246:317-28). With the aim of verifying the molecular weight of the protein and to confirm the presence of the disulphide bridge, the aliquot of DIIIE2J purified by rp-HPLC was further analyzed by mass spectrometry. As can be seen in FIG. 2, the major species of the DIIIE2J preparation has a mass of 13515.00 Da, which differs by 1.32 Da from the expected value if the N-terminal Met from this molecule were removed by the *E. coli* methionyl-aminopeptidase (MAP). (FIG. 2B). The result confirms that the N-terminal Met has been removed homogeneously from the DIIIE2J preparation by MAP, but the difference in mass does not allow the confirmation of the presence, or absence, of the disulphide bridge.

In order to further examine the status of the disulphide bridge, an aliquot of the rp-HPLC purified DIIIE2J was separated into 2 fractions with the same volume. One of the fractions was reduced with dithiothreitol, after which both fractions were alkylated by treatment with iodoacetamide, followed by ESI-MS analysis. The results showed that the alkylating agent had been incorporated only in the fraction previously treated with dithiothreitol, evidenced by an increased mass of 13631.0 Da that differs only by 1.2 Da from the expected value for the reduced and carbamidomethylated species. The fraction subjected only to alkylation without previous reduction has the same mass (13515.00 Da) as the untreated protein, confirming that the preparation of DIIIE2J does not have free sulfhydryl groups and that the 2 Cys residues of the molecule are bonded forming the characteristic disulphide bridge of DIII.

The antigenic characterization of the protein was performed in a dot-blot assay. As can be seen in FIG. 3, DIIIE2J is strongly bound by murine anti-DV sera, showing a marked specificity towards the homologous serotype (FIG. 3). The protein is also recognized by the sera from persons which have been infected by the virus under varying epidemiological settings. This result evidences that the preparation of DIIIE2J reproduces structural elements present in the context of complete, intact viral particles.

Figure 4:
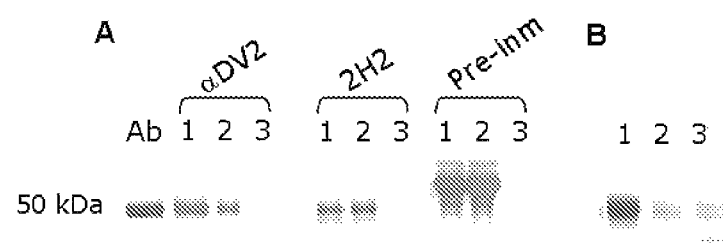

In order to be employed as an affinity chromatography ligand, it is important to ascertain whether the immobilized DIIIE2J is capable of reproducing the interactions in which it is involved in the context of the viral surface. With this goal, DIIIE2J was immobilized on Sepharose 4B and tested for binding of antibodies originally raised against complete viral particles. Aliquots of 20 μL of the DIIIE2J affinity resin were equilibrated in binding buffer (PBS pH 7.4, 0.1% Tween-20) and incubated with the antibody samples, diluted in binding buffer, for 30 min. at 25° C. (In each step, removal of the added solution was achieved by centrifugation at 500×g for 5 min). After extensively washing the resin with binding buffer, the bound antibodies were eluted by successive incubations in 20 mM Gly pH 2.5 and in reducing sample buffer for SDS-PAGE. The results obtained in this experiment evidenced that the immobilized recombinant protein is capable of binding specifically the antibodies obtained by immunization with whole virions (FIG. 4), confirming that it mimics the interacting surface of DIII exposed in the virion and that, therefore, it can be used for the isolation of prospective viral receptors.

protein E from human plasma, with the aim of screening for potential cellular receptors of DV. Plasma samples, obtained from healthy donors 30 to 40 years old with no detectable antibodies to the virus, were inactivated by incubation at 56° C. for 1 hour, and the precipitated proteins were removed from the solution by centrifugation (5000×g, 10 min.). The supernatant was stored at −80° C. until used.

The isolation of proteins binding to DIII was performed by affinity chromatography. Four parts of human plasma, processed as described above, were mixed with one part of 100 mM HEPES pH 6, 1.75 M NaCl, 25 mM $CaCl_2$, 5 mM $MgCl_2$ and loaded into a column (1.5 cm diameter×1.2 cm height) packed with the DIIIE2J affinity resin, at a flow of 10 cm/h. The sample was recirculated under these conditions on the column for 4 additional hours, at 25° C., and then the column was extensively washed with 100 column volumes of 20 mM HEPES buffer, pH 6, 0.35 M NaCl, 5 mM $CaCl_2$, 1 mM $MgCl_2$. Additionally, the column was washed with 20 mM HEPES buffer pH 6, 0.5 M NaCl, 5 mM $CaCl_2$, 1 mM $MgCl_2$. Elution of the bound protein was achieved by loading 10 mM Gly pH 2.5 into the column, monitoring the absorbance at 280 nm of the eluate with an UV detector.

In order to identify the protein species present in the eluate, a 100 μL aliquot of the collected fraction was precipitated with 10% trichloroacetic acid, resuspended in 20 μL of sample buffer, and subjected to SDS-PAGE. The protein bands were excised and digested with trypsin, followed by ESI-MS analysis of the eluted peptides.

The mass spectra obtained for each protein band were inspected, and the signals with the highest intensity were fragmented to obtain sequence information for the peptides. In all cases, the sequenced peptides corresponded to tryptic fragments from human plasma proteins (table 1).

TABLE 1

Summary of the proteins identified on the eluate from the affinity chromatography with immobilized DIIIE2J.

| SEQ ID. No. | Peptide sequence | ID Mascot[1] | Description of the protein |
| --- | --- | --- | --- |
| SEQ ID. 82 | VTAAPQSVCALR | P01023 | Human α2-macroglobulin |
| SEQ ID. 83 | LPPNVVEESAR | | |
| SEQ ID. 84 | VGEYSLYIGR | P02743 | Human serum Amyloid P component |
| SEQ ID. 85 | IVLGQEQDSYGGK | | |
| SEQ ID. 86 | LICQATGFSPR | P04220 | Heavy chain from human IgM |
| SEQ ID. 87 | LTCLVTDLTTYDSVTISWTR | | |
| SEQ ID. 88 | VFDEFKPLVEEPQNLIK | Q645G4 | Human serum albumin |
| SEQ ID. 89 | QNCELFEQLGEYK | | |
| SEQ ID. 90 | DSTYSLSSTLTLSK | P01834 | C region from the kappa chain of human IgG |

[1]Access number in the Swiss-Prot databank of the protein identified by MASCOT (Perkins D N, Pappin D J, Creasy D M, Cottrell J S (1999) Probability-based protein identification by searching sequence databases using mass spectrometry data. Electrophoresis 20: 3551-67) based on the data obtained by ESI-MS analysis.

Example 2

Human A2M Interacts Directly with DIII from Protein E of DV2.

The presence of soluble fragments from cellular receptors in human plasma is widely known. On the other hand, it is also known that the addition of serum to culture media has a marked influence on the efficiency of infection of cultured cells by DV (Nash D R, Halstead S B, Stenhouse A C, McCue C. (1971) *Nonspecific Factors in Monkey Tissues and Serum Causing Inhibition of Plaque Formation and Hemagglutination by Dengue Viruses. Infect Immun.* 3:193-199). Therefore, it was decided to try to isolate proteins with affinity for DIII of Besides the proteins involved in direct, specific interactions with the immobilized ligand, there are other molecules in the eluate from the affinity chromatography that have no relevance for this binding. Both albumin (Q645G4, table 1) and IgM and IgG immunoglobulins (P04220 and P01834, table 1) are common contaminants eluted during affinity chromatography experiments with ligands of different specificities, probably due to their high abundance in human plasma, where they can be found at concentrations of approximately 35 mg/mL for albumin, 12-15 mg/ml for IgG and 5 mg/ml for IgM. The presence of immunoglobulins could also be explained by the existence of cross-reactivity with DIIIE2J in some antibodies from human plasma that are actually specific for other antigens.

The presence of A2M (P01023, table 1; Seq. ID. 2) within the set of identified proteins was considered as particularly interesting. It is known that A2M functions as a carrier protein for other molecules that can be targeted, in this manner, to the endocytic pathway via the cellular A2MR receptor (Seq. ID. 3). Also, there are proteins in the chromatographic eluate that may not be involved in direct interactions with the immobilized ligand, and might rather be part of ternary complex with other identified proteins that do bind the ligand (Gavin A C, Bosche M, Krause R, Grandi P, Marzioch M, Bauer A, Schultz J, Rick J M, Michon A M, Cruciat C M, Remor M, Hofert C, Schelder M, Brajenovic M, Ruffner H, Merino A, Klein K, Hudak M, Dickson D, Rudi T, Gnau V, Bauch A, Bastuck S, Huhse B, Leutwein C, Heurtier M A, Copley R R, Edelmann A, Querfurth E, Rybin V, Drewes G, Raida M, Bouwmeester T, Bork P, Seraphin B, Kuster B, Neubauer G, Superti-Furga G (2002) *Functional organization of the yeast proteome by systematic analysis of protein complexes Nature.* 415:123-4).

Figure 5:
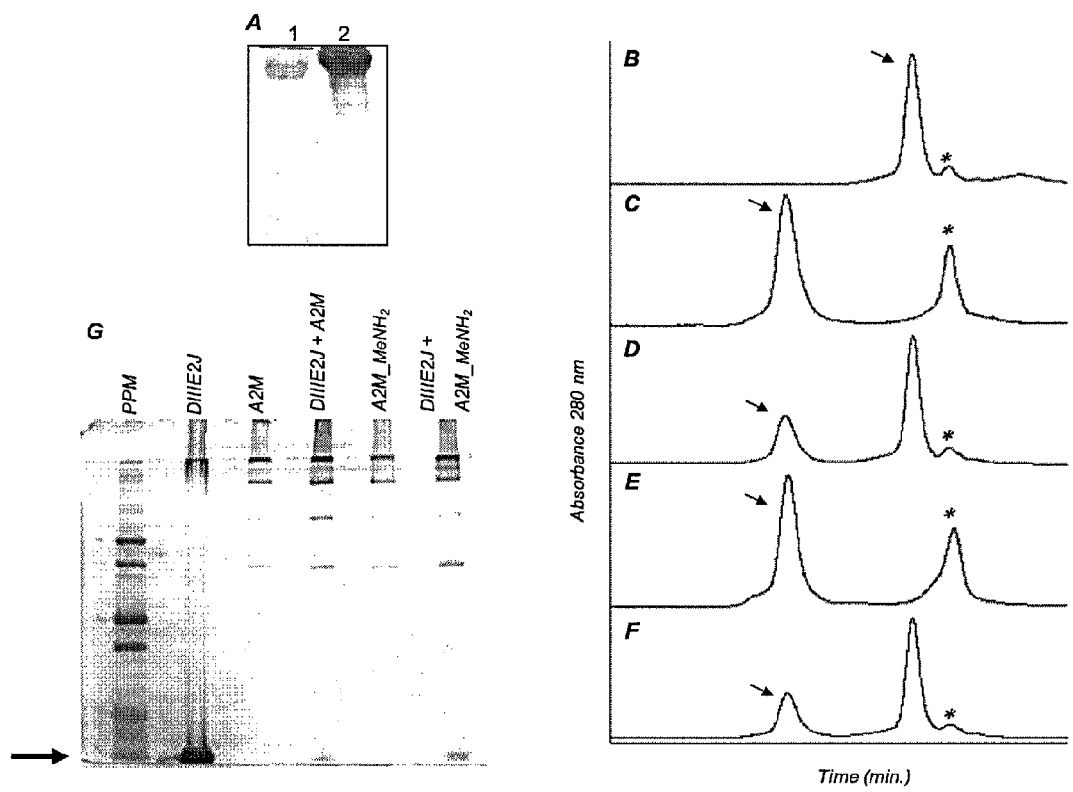

In order to determine whether the isolation of A2M is due to a direct interaction with DIIIE2J, a 100 µg aliquot of the latter protein in PBS pH 7.4 was incubated in independent experiments with 100 µg of either non-activated or activated (by methylamine treatment) human A2M. The molar concentration of the proteins in the mixture was $1.4 \times 10^{-4}$ mol/L for DIIIE2J and $7 \times 10^{-7}$ Mol/L for both variants of human A2M. The reaction was incubated for 1 hour at 37° C. and then loaded into a 10/30 Superdex 200 HR gel filtration column previously equilibrated with 50 mM $NaHPO_4$ buffer, pH 7.0/ 300 mM NaCl, at a flow of 0.4 mL/min (FIGS. 5E and F). Before loading the mixed proteins, the elution profile and the retention time of DIIIE2J and A2M were established for each one separately, using chromatographic runs with the purified proteins. (FIG. 5B-D). In all cases, the fractions collected from each run were precipitated with acetone and analyzed by 15% SDS-PAGE, keeping constant the ratio to the total volume of each fraction (1/5). FIG. 5G evidences the formation of a complex between DIIIE2J and the two variants of A2M, manifested by the appearance of the band corresponding to DIIIE2J in the high molecular weight fraction. This result constitutes the first evidence of a physical interaction between A2M and DIII from the envelope protein of DV.

Example 3

Determination of the Affinity Constants for the Interaction Between DIIIE2J and A2M by Biacore In order to estimate the strength of the interaction between DIIIE2J and human A2M, 1600 RU of DIIIE2J were covalently immobilized on a CM5 chip (channel 1, FIG. 6A) (Biacore, Sweden), following the procedure described in the Materials and Methods section.

During preliminary experiments (FIGS. 6B and C) it was possible to confirm the presence on the surface of the chip of immobilized protein exposing regions of its surface that are also exposed in the context of the viral particle. This confirmation was achieved by measuring the specific interaction of the immobilized molecules with antibody preparations obtained by immunization with DV. Specifically, the binding by the 3H5 monoclonal antibody (FIG. 6C) evidences the correct exposure and formation of a topographical epitope that depends on the presence of the disulphide bridge between the two cysteine residues of DIII.

Figure 6:
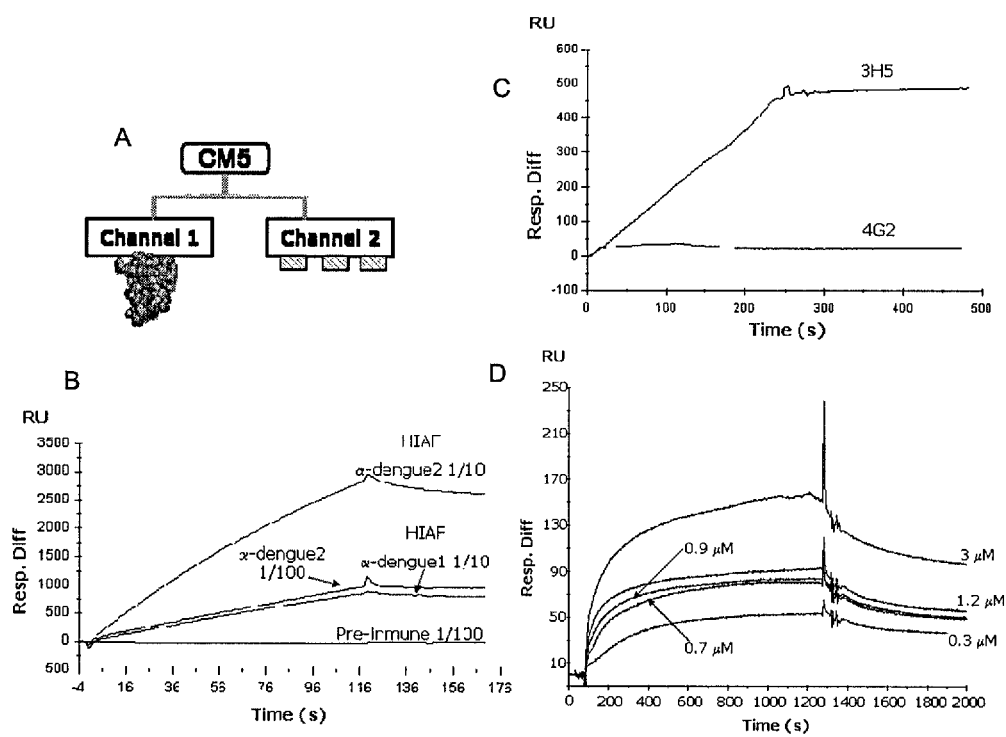

By loading A2M at concentrations from 0.3 µMol/L to 3 µMol/L, it was possible to determine that the interaction between both proteins is saturable and reversible (FIG. 6D). The association and dissociation curves obtained allowed the estimation of the apparent Kd, in the order of $10^{-7}$ Mol/L. This value may represent an interaction of much higher avidity in the context of the whole virion, where DIII is arranged as multiple copies around a symmetry axis and where, therefore, multipoint binding to oligomeric proteins such as A2M is favored. The fact that the interaction is reversible confirms the possibility that A2M may function as a carrier protein for the entry of DV to its host cell.

Example 4

Natural Ligands of the A2MR Receptor Inhibit Binding of DIII to Vero Cells and Viral Infection.

RAP is a natural molecular chaperone for LRP1. This protein controls the activity of LRP1, possibly by mediating a conformational change that precludes the binding and/or the internalization of several ligands for this receptor (Herz J, Goldstein J L, Strickland D K, Ho Y K, Brown M S. (1991) *39-kDa protein modulates binding of ligands to low density lipoprotein receptor-related protein/alpha 2-macroglobulin receptor J Biol Chem.* 266:21232-8). Therefore, RAP constitutes an ideal ligand to obtain evidences for the involvement of LRP1 on the endocytosis of DV in mammalian cells.

The Vero cell line has been widely used in the study of the nature of the interactions of DV with its cellular receptors. These cells are highly susceptible to infection by the four viral serotypes. They constitute a particularly advantageous tool for the evaluation of antiviral activities against DV, since they can be used for assays measuring the inhibition of the formation of lytic plaques.

Figure 7:
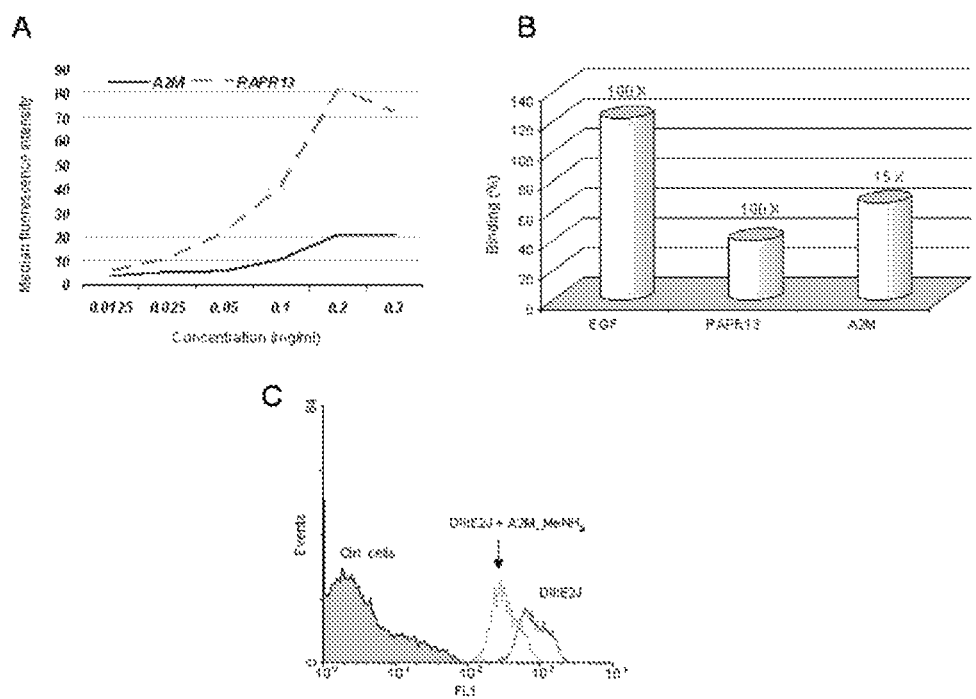

Given that this cell line is derived from monkey kidney cells and that the ligands for the A2MR receptor used in the assays are of human origin, a preliminary and necessary step was the corroboration of the binding of the RAPR13 and A2M $MeNH_2$ proteins to Vero cells. With this aim, these proteins were fluoresceinated, and their binding to the surface of Vero cells was measured using flow cytometry. Both molecules exhibited a concentration-dependant and saturable binding behavior in this cell line (FIG. 7A).

After this first experiment, it was determined whether RAPR13 was able to inhibit the binding of A2M-$MeNH_2$ to Vero cells, by incubating pre-fixed cells for 30 min. at 4° C. with mixtures of fluoresceinated A2M_$MeNH_2$ and either RAPR13 or human recombinant EGF as a control, using the unlabelled proteins at a 100-fold molar excess. The obtained results evidence a decrease in fluorescence for the cells incubated with A2M_$MeNH_2$ in the presence of RAPR13, in contrast to the samples incubated with A2M_$MeNH_2$ in the presence of recombinant human EGF (FIG. 7B). These results corroborate that both A2M_$MeNH_2$ and RAPR13 bind in a specific and functional manner to the A2MR receptor in Vero cells.

The assay for the inhibition of infection was performed on 24-well plates seeded with a monolayer of Vero cells at approximately 90% confluence. The dilution of the virus was adjusted to obtain approximately 20 lytic plaques per well. The results of the assay showed a drastic reduction in the number of lytic plaques when the cells were pre-incubated before adding the virus either with the RAPR13 protein or with a preparation of polyclonal antibodies against the A2MR receptor (table 2). There were no significant reductions when the cells were pre-incubated with BSA or with antibody preparations against an unrelated antigen.

TABLE 2

Assay for the inhibition of the infection of Vero cells by a natural ligand of the A2MR receptor or by anti-receptor antibodies[1].

| Protein | DV1 | DV2 | DV3 | DV4 |
|---|---|---|---|---|
| RAPR13 | 65 | 76 | 60 | 75 |
| BSA | 7 | — | — | — |
| α-A2MR | 82 | 90 | 90 | 85 |
| α-NR | 5 | — | — | — |

[1]The results represent the average from three independent determinations. The viral strains used in the assay were West Pac 74 for DV1, S16803 for DV2, CH53489 for DV3 and TVP360 for DV4.
The proteins RAP13 and BSA were used at a concentration of 100 μg/mL in the assay. α-A2MR: antibodies obtained by immunization with the A2MR receptor. α-NR: Antibodies obtained by immunization with an unrelated protein. Both antibody preparations were used at a 1/100 dilution.

Figure 8:
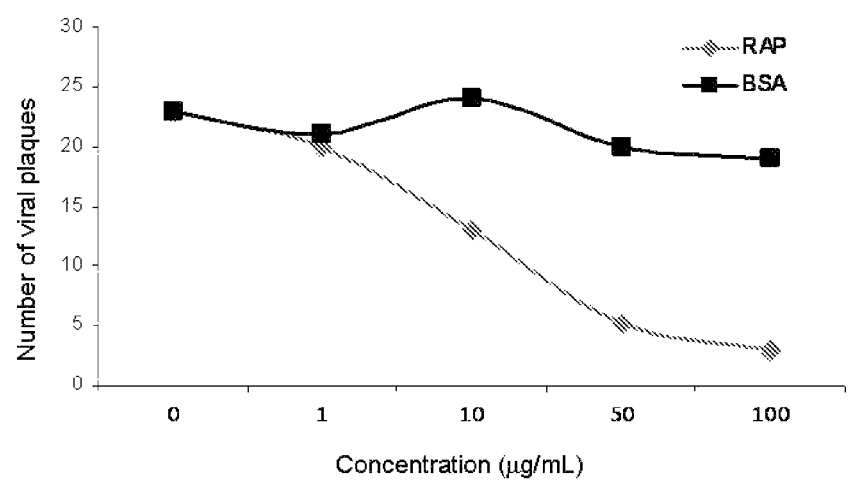

Similarly, it was possible to show by means of a lytic plaque reduction assay that the inhibition of the infection obtained for DV2 with the RAPR13 protein is dependent on the protein concentration used in the experiment (FIG. 8). This result constitutes a strong evidence for the involvement of the A2MR receptor in mediating the entry of DV to its target cell.

Example 5

Design of Topographic, Structurally Constrained Synthetic Peptides

Even though the essential role played by DIII in the binding of FV to the host cells is widely acknowledged, there are no reports of DIII-derived synthetic peptides with a potent (at nanomolar or low-micromolar ranges) activity for the inhibition of DV infection. Several reasons explain this situation: 1) It is not trivial to mimic the structural determinants of whole proteins with synthetic peptides, since the surface patches involved in protein-protein interactions are often topographic, composed of residues which are closely positioned on the three-dimensional structure but separated along the sequence of the protein, 2) Usually, these interaction patches are fairly large, with areas ranging from several hundred to a few thousand Å$^2$. This magnitude is larger than the total surface of small peptides, 3) Peptides have a flexible structure in solution, which implies that there will be a considerable loss in conformational entropy upon adoption of the structure which is biologically relevant for the interaction with its binding partner and, therefore, the affinity of the peptide-protein complex will be significantly lower than that of the protein-protein complex, 4) It is possible for the peptide to adopt relatively stable conformations in solution, but these conformations can be different from that adopted by the peptide in the context of its native protein, 5) The binding of the virus to its protein receptor(s) may involve multipoint interactions and therefore will have a large avidity, since the viral surface has multiple symmetric copies of DIII. This imposes a high energy barrier for the competition between the virus and the peptide for the receptor. Data obtained during studies on the structure-function relationship of the interaction between the A2MR receptor and its natural ligands have shown the important role played by clusters of basic residues and/or by Lys/Arg side chains on the surface of the A2MR ligands. Such is the case of Lys1370 for A2M (SEQ ID. 2) and Lys57 for exotoxin A from *Pseudomonas aeruginosa*, which, if changed by site-directed mutagenesis, result in significant drops in binding of the ligand to the receptor (Arandjelovic S, Hall B D, Gonias S L (2005) *Mutation of lysine 1370 in full-length human alpha2-macroglobulin blocks binding to the low density lipoprotein receptor-related protein-1. Arch Biochem Biophys.* 438:29-35, Wedekind J E, Trame C B, Dorywalska M, Koehl P, Raschke T M, McKee M, FitzGerald D, Collier R J, McKay D B. (2001) *Refined crystallographic structure of Pseudomonas aeruginosa exotoxin A and its implications for the molecular mechanism of toxicity J Mol Biol.* 314:823-37). Similarly, other studies have underscored the prominence of a basic cluster formed by residues 136-150, together with Arg172, for the apoE protein (Raussens V, Slupsky C M, Ryan R O, Sykes B D (2002) *NMR structure and dynamics of a receptor-active apolipoprotein E peptide. J Biol Chem.* 277:29172-80).

On the other hand, the ligand binding domains of the A2MR receptor and, in general, those of all members of the LDL receptor family, are characterized by a significantly negative electrostatic potential on the ligand binding surface, due to the presence of exposed, conserved acid residues that can interact favorably with basic residues on the interacting ligand. For example, the crystallographic structure of a complex between a fragment of the VLDL receptor and human rhinovirus 2, belonging to the minor group of the rhinoviruses, shows a close interaction between LYS224 of the VP1 protein from the viral capsid and residues ASP139 and GLU137 from the receptor (Verdaguer N, Fita I, Reithmayer M, Moser R, Blaas D (2004) *X-ray structure of a minor group human rhinovirus bound to a fragment of its cellular receptor protein. Nat Struct Mol Biol.* 11:429-34). The aliphatic side chain of Lys224 from VP1 interacts, additionally, with Trp132 from the receptor domain which, although not strictly conserved among all the ligand binding domains of A2MR, is the most frequent aminoacid at this position (in 20 domains out of 31, with Leu appearing in 4 domains, Phe in 3, Arg in 2 and Lys and Ser in only 1 each) (FIG. 9). Table 3 shows the ligand binding patches of the A2MR receptor, defined by the positions structurally equivalent to Trp132, ASP135, GLU137 and ASP139 in the VLDL receptor.

TABLE 3

Ligand binding patches in the A2MR receptor[1]

| SEQ ID No. | Domain* | First resid. | Last resid. | Length in aa. | P1 | P2 | P3 | P4 |
|---|---|---|---|---|---|---|---|---|
| 32 | A1 | 25 | 66 | 42 | W45 | D48 | E50 | D52 |
| 33 | A2 | 70 | 110 | 41 | R90 | N93 | V95 | D97 |
| 34 | A3 | 852 | 892 | 41 | W871 | D874 | D876 | D878 |
| 35 | A4 | 893 | 933 | 41 | W912 | D915 | D917 | D919 |
| 36 | A5 | 934 | 973 | 40 | W953 | D956 | D958 | D960 |
| 37 | A6 | 974 | 1013 | 40 | W994 | D997 | D999 | D1001 |
| 38 | A7 | 1013 | 1053 | 41 | W1032 | D1035 | D1037 | D1039 |
| 39 | A8 | 1060 | 1099 | 40 | W1080 | D1083 | D1085 | D1087 |
| 40 | A9 | 1102 | 1142 | 41 | W1123 | D1126 | D1128 | D1130 |
| 41 | A10 | 1143 | 1182 | 40 | K1164 | D1167 | N1169 | D1171 |
| 42 | A11 | 2522 | 2563 | 42 | L2542 | D2545 | V2547 | H2549 |
| 43 | A12 | 2564 | 2602 | 39 | L2583 | N2586 | A2588 | D2590 |
| 44 | A13 | 2603 | 2641 | 39 | S2622 | N2625 | F2627 | D2629 |
| 45 | A14 | 2642 | 2690 | 49 | W2671 | D2674 | A2676 | D2678 |

TABLE 3-continued

Ligand binding patches in the A2MR receptor[1]

| SEQ ID No. | Domain* | First resid. | Last resid. | Length in aa. | P1 | P2 | P3 | P4 |
|---|---|---|---|---|---|---|---|---|
| 46 | A15 | 2694 | 2732 | 39 | W2713 | D2716 | E2718 | D2720 |
| 47 | A16 | 2732 | 2771 | 40 | W2751 | D2754 | S2756 | D2758 |
| 48 | A17 | 2772 | 2814 | 43 | W2792 | D2795 | D2797 | D2799 |
| 49 | A18 | 2816 | 2855 | 40 | F2835 | D2838 | D2840 | D2842 |
| 50 | A19 | 2856 | 2899 | 44 | W2876 | D2879 | E2881 | D2783 |
| 51 | A20 | 2902 | 2940 | 39 | L2922 | N2925 | Q2927 | D2929 |
| 52 | A21 | 3332 | 3371 | 40 | W3351 | D3354 | E3356 | D3358 |
| 53 | A22 | 372 | 3410 | 39 | F3391 | 3394 | D3396 | D3398 |
| 54 | A23 | 3411 | 3450 | 40 | F2431 | N2434 | Q2436 | N2438 |
| 55 | A24 | 3451 | 3491 | 41 | W3471 | D3474 | D3476 | D3478 |
| 56 | A25 | 3492 | 3533 | 42 | W3512 | D3515 | E3517 | D3519 |
| 57 | A26 | 3534 | 3572 | 39 | W3553 | D3556 | D3558 | D3560 |
| 58 | A27 | 3573 | 3611 | 39 | W3592 | D3595 | D3597 | D3599 |
| 59 | A28 | 3611 | 3649 | 39 | W3630 | D3633 | D3635 | D3637 |
| 60 | A29 | 3652 | 3692 | 41 | W3671 | D3674 | E3576 | D3678 |
| 61 | A30 | 3693 | 3733 | 41 | R3714 | D3717 | T3619 | N3621 |
| 62 | A31 | 3739 | 3778 | 40 | L3759 | N3762 | F3764 | D3766 |

[1]The numbering in the table corresponds to the sequence of human A2MR (SEQ ID No. 3). Domain: Denomination of the ligand binding domains of the human A2MR receptor in the SwissProt databank. First resid. and Last resid., positions of the first and last residue of the different ligand binding domains of the receptor. Length in aa.: total number of aminoacids of the ligand binding domain. P1-4: residues forming the ligand binding patch.

Given the importance of the Lys/Arg residues and, in general, of electrostatic charges in the interaction with the ligand binding domains of the LDL receptor family, we inspected the localization of the charged residues in the upper and lateral exposed surfaces of the three-dimensional models of the structure of DIII corresponding to DV1-4.

For this analysis, the structures of the E protein from DV2 and DV3 (entries 1oan and 1uzg in the Protein Data Bank) were used as templates for building models of the 3D structure of the E protein from DV1 and DV4, using the program MODELLER (A. Sali, T. L. Blundell. (1993) *Comparative protein modelling by satisfaction of spatial restraints. J. Mol. Biol.* 234:779-815). As can be seen in FIG. 10, there are four surface patches corresponding to lysine side chains which are conserved in the four serotypes. With the exception of the patch defined by Lys310 in DV1, 2 and 4 (Lys308 in DV3), the remaining patches are not conserved strictly at the level of their localization in the primary structure, but rather in their topographic position on the protein surface. This is possible due to the appearance of correlated mutations in nearby positions in the 3D structure of the protein and due to the flexibility of the side chain of lysine. Two of the patches are located on the exposed surface corresponding to the beta sheet defined by strands A, B, C', D and E (FIG. 11A), whereas the remaining patches are located in the lateral/upper surface corresponding or adjacent to the FG beta hairpin.

At least one of the four conserved lysine patches on the surface of the DIIIs, and specially the two patches located on or adjacent to the exposed surface of the FG beta hairpin, interact favorably with the ligand binding patches of the A2MR receptor, defined on table 3.

In order to design DIII-based peptides that can inhibit the infection of FV, the Ser376-Trp391 segment (residue numbering from DV2) was selected as the starting point. This segment comprises the FG beta hairpin, which exposes a total area of 745 Å$^2$ to the solvent and is part of the upper/lateral surface of the domain that remains exposed in the context of the structure of the mature virion. Several mutations in this region have been reported to affect the binding of neutralizing antibodies which block the interaction of the virus with the cell or affect the viral phenotype. The structure of the backbone of this segment is conserved between the available crystallographic structures of protein E from DV2 and DV3 (FIG. 11B). This structural conservation also includes the F-G loop, which has a type II beta turn between the residues Glu383-Gln386 (residue numbering according to SEQ ID 1). The conservation of the structure of the backbone of the FG segment is also applicable to DV1 and DV4, considering the degree of similarity between the corresponding sequences in addition to the structural similarity between the 3D models of protein E from these viruses, obtained by homology modeling based on the DV2 and DV3 coordinates, respectively (FIG. 11B).

FIGS. 11(C and D) shows the primary structure and 3D models of the synthetic peptides HDIII2CL and HDIII3CL, designed on the basis of the FG hairpin from DV2 and DV3.

The synthetic peptides include two cysteines, one in the N-terminus and another in the C-terminus. These residues can form a disulphide bridge which is compatible structurally with a beta hairpin structure, as indicated by the models of the three-dimensional structure of these peptides (FIGS. 11C and D). In these models, the alpha carbons of the cysteines are separated by 5.7 Å, which is a common distance for disulphide bridges. The cyclization by a disulphide bridge contributes to the stabilization of the hairpin structure of the peptide by decreasing the conformational entropy of its backbone.

The design allows the formation of 6 hydrogen bonds between the backbone of the F and G strands of the peptide, further increasing its stability (Figure C and D). Residues 4 and 6 (strand F) and 13, 15 and 17 (strand G) are hydrophobic and are oriented towards the same face of the hairpin, which guarantees a favorable hydrophobic interaction between them. Residues 4-6 of the F beta strand are bifurcated at the beta carbon, and are characterized by a high propensity for the adoption of beta/extended structures.

Peptide HDIII3CL (SEQ ID. 7) includes residues Lys11 and Lys14, corresponding to two lysine patches of DIII which constitute putative sites for a favorable interaction with the ligand binding domains from A2MR. Peptide HDIII2CL (SEQ ID. 5) only has 1 patch formed by Lys14; whereas HDIII1CL (DV1, SEQ ID. 6) has two patches and HDIII4CL (DV4, SEQ ID. 8) has none.

Additionally, the cyclic peptides HDIII2Cs (Seq. ID. 4) and pepDIII-1 were designed, corresponding respectively with the sequences Ile379-Lys388 and Gly381-Gln386 from protein E of DV2 (FIG. 12A). Both peptides include cysteines at the N- and C-termini for their cyclization via disulphide bridges that are structurally compatible with the 3D structure of the native protein. Peptide HDIII2Cs is analogous to peptide HDIII2CL, but includes only a portion of the F and G beta strands. On the other hand, peptide pepDIII-1 only includes the F-G loop.

Example 6

Peptide HDIII2Cs Reproduces a Topographic Epitope from DIII of DV2

With the aim of evaluating the recognition of peptide HDIII2Cs by mAb 3H5, peptide-BSA conjugates were prepared and analyzed by Western blotting with this antibody (FIG. 12B). The recombinant protein PD5 was used as a positive control for this assay. This protein is formed by DIII from protein E of DV2 (residues 286-426) fused to the C-terminal of the lipoamide dehydrogenase (P64k) from *Neisseria meningitidis*. PD5 has been evaluated as a vaccine candidate, and it is capable of eliciting a protective immune response as evaluated by a viral challenge in models of infection in mice and monkeys (Hermida L., Rodriguez R., Lazo L., Silva R., Zulueta A., Chinea G., Lopez C., Guzman M. G. and Guillen G. (2004) *A dengue-2 Envelope fragment inserted within the structure of the P64k meningococcal protein carrier enables a functional immune response against the virus in mice. J Virol Methods.* 115: 41-49), evidencing that this protein displays important epitopes from this region of the virus.

Monoclonal antibody 3H5 was obtained by immunization with a DV2 preparation (Gentry M K, Henchal E A, McCown J M, Brandt W E, Dalrymple J M. (1982) *Identification of distinct antigenic determinants on dengue-2 virus using monoclonal antibodies Am J Trop Med Hyg.* 31(Pt 1):548-55), and recognizes in a serotype-specific manner an epitope on DIII that depends on the presence of the disulphide bridge. This antibody is potently neutralizing against isolates belonging to serotype 2. The published data indicate that there is a high correlation between the neutralizing activity of this mAb and its capacity for inhibiting binding of the virus to its cellular receptors (He R T, Innis B L, Nisalak A, Usawattanakul W, Wang S, Kalayanarooj S, Anderson R (1995) *Antibodies that block virus attachment to Vero cells are a major component of the human neutralizing antibody response against dengue virus type 2 J Med. Virol.* 45:451-61). The specific recognition of peptide HDIII2Cs by this antibody evidences that the peptide reproduces a topographic epitope from the surface of DIII of major functional importance.

One of the tools used for the characterization of topographic peptides is the obtention and characterization of anti-peptide sera. With the aim of gathering additional evidence supporting the hypothesis that the designed peptide reproduces the antigenic characteristics of the equivalent region from protein E in the virus, an immunization scheme was started using a HDIII2Cs-KLH conjugate as the immunogen. The scheme comprised the subcutaneous administration of five doses of the HDIII2Cs-KLH conjugate to 10 Balb C mice. The anti-peptide titer of the sera from immunized animals (1/2700) was determined using an indirect ELISA assay, coating the plates with HDIII2Cs and comparing the reactivity of the immune sera with that of pre-immune controls.

In order to evaluate whether the HDIII2Cs peptide was capable of eliciting a conformation-dependent antibody response, a dot blotting assay was performed in which two pieces of nitrocellulose membrane were sensitized with the PD5 protein and the HDIII2Cs peptide, either unmodified or reduced and carbamidomethylated (FIG. 12C). The assay evidenced a decrease in signal intensity for the recognition by the sera of both PD5 and the peptide upon loss of their disulphide bridges. The assay also evidenced that the peptide is recognized by mAb 3H5, and this signal is lost upon reduction and carbamidomethylation of the peptide.

Finally, we evaluated the recognition by the anti-peptide sera of the virus obtained after the infection of Vero cells in a Western blotting format, as well as its capacity for immuno-precipitating $^{35}$S_VD2. In the Western blot, the anti-HDIII2Cs serum recognized a band at the same position of a band recognized by mAb 3H5, corresponding to the molecular weight of protein E (FIG. 13A). There were no signals on the membrane incubated with the pre-immune sera, evidencing that the recognition mediated by the anti-peptide response was specific. Finally, the anti-HDIII2Cs serum was capable of immunoprecipitating the E protein from DV2 (FIG. 13B).

The obtained results evidence that the HDIII2Cs peptide mimics a disulphide bridge-dependent epitope from DIII of protein E from DV2, and that the conformational restriction imposed on the peptide by the disulphide bridge has a dominant effect on the antibody response obtained upon immunization with this antigen. Thus, the cyclization of the peptide is necessary for properly mimicking the structure of this epitope.

Example 7

The HDIII2CL Peptide is a Better Mimic of the Structure of the Epitope than Peptide HDIII2Cs An immunization schedule was started with the objective of determining whether the HDIII2CL peptide was able to elicit a better response than peptide HDIII2Cs, evaluated on the basis of the conformational characteristics of this antigenic region on the viral particle. The immunization scheme also included peptides HDIII2Cs and pepDIII-1 (FIG. 12A). Similarly to the earlier scheme, this experiment used peptide-KLH conjugates as antigens, and followed the same dosing and immunization route described in example 6.

The resulting anti-peptide sera were tested in an indirect ELISA assay, coating the plates with PD5 and P64k in three variants: unmodified, carbamidomethylated, and reduced/carbamidomethylated. Both the anti-HDIII2Cs and the anti-HDIII2CL sera recognize protein PD5 in a conformation-dependent manner, as evidenced by higher reactivities with the unmodified protein, as compared to the reduced and carbamidomethylated variant (FIG. 14). However, the impact of the loss of the disulphide bridge on the recognition of the protein by the anti-HDIII2CL serum is higher than for the anti-HDIII2Cs serum, and reproduces better the effect seen for anti-DV2 sera obtained by the immunization of mice with viral preparations (FIG. 14). This result shows that the redesign that resulted in peptide HDIII2CL achieves a better representation of the conformation present in this region of DIII in the context of the virus.

Example 8

Topographic Peptides Corresponding to the FG Turn Display Wide-spectrum Inhibition Against the Four Serotypes of DV An assay was performed with peptides HIII2CL and HIII3CL (FIGS. 11C, 10D and 15) in order to estimate their capacity to mimic the interactions of DIII with cellular surface molecules. The assay employed biotinylated peptides in order to facilitate their detection in flow cytometry experiments by means of a streptavidin-FITC conjugate. FIG. 16 depicts the histograms representing the behavior of the intensity of the fluorescence in the cells after incubation with different dilutions of the HIII2CL and HIII3CL peptides, in addition to an unrelated peptide (0.3-0.02 mg/ml). The results show that both peptides bind the cellular surface on a concentration-dependent manner (FIG. 16), implying that the interaction is specific. The shift in the histogram produced by peptide HIII3CL is significantly larger than that produced by HIII2CL. This result indicates that the HIII3CL peptide establishes a higher-affinity interaction, which is coherent with the presence in this molecule of two lysine residues that are potentially important for the interaction with the A2MR receptor (Lys11 and Lys14, FIGS. 10C and 11D), versus the absence of one of them (Lys11, FIGS. 10B and 11C) from the HIII2CL peptide.

DIII has one of the most variable regions of the exposed surface of protein E. In fact, one of the antigenic characteristics of this domain is that the antibodies obtained against this region are predominantly serotype-specific (Roehrig J T, Bolin R A, Kelly R G (1998) *Monoclonal antibody mapping of the envelope glycoprotein of the dengue 2 virus, Jamaica Virology* 246:317-28). However, during the inhibition assay with different DV serotypes, the peptides display a wide-spectrum inhibitory activity, efficiently inhibiting the infection of strains of the homologous, as well as of the heterologous serotypes (table 3). It is important to notice that at the assayed concentration (0.1 mg/ml) all the peptides in all the conditions, with the exception of peptide HIII4CL for DV3, produced higher than 50% inhibition levels.

TABLE 3

Inhibition of the infection of the four serotypes of DV by the designed peptides.

| Peptide | DV1 | DV2 | DV3 | DV4 |
|---------|-----|-----|-----|-----|
| HDIII1CL | + | + | + | + |
| HDIII2CL | + | + | + | + |
| HDIII3CL | + | + | + | + |
| HDIII4CL | + | + | +/− | + |
| HDIII2Cs | − | − | − | − |
| 3H5pept | − | − | − | − |

The showed results correspond to an assay of reduction of the number of viral plaques, performed on Vero cells. The peptides were used at a concentration of 0.1 mg/ml. The symbols represent the degree of reduction of the number of viral plaques in the experimental condition, compared to a control where the cells were incubated with the virus without previous treatment with the peptide. (+) 50% or higher decrease, (+/−) 10-50% decrease in the number of plaques, (−) Less than 10% decrease in the number of plaques.

FIG. 17 presents additional results confirming the potent inhibitory activity of the peptides against the homologous and the heterologous serotypes. Peptide HDIII2CL achieves a 60% inhibition of the infection against a virus of its homologous serotype (DV2), and an 80% inhibition against DV1 (FIG. 17B). Also, peptide HDIII3CL inhibits the infection by DV2 with the same or higher efficiency than peptide HDIII2CL (FIG. 17C). In both assays (FIGS. 17B and C) the peptides HDIII2CL and HDIII3CL have a significantly better effect than the remaining peptides tested (3H5pept, NR3pep and pepDIII-1).

Based on the structural similarity between different FV for protein E, it was decided to design peptides corresponding to the same DIII region of other FV of interest for animal and human health (FIG. 18): Yellow Fever virus (Seq. ID. 10), West Nile Virus (Seq. ID. 11), Japanese Encephalitis virus (Seq. ID. 12), Tick-borne encephalitis virus (Seq. ID. 13), Kunjin virus (Seq. ID. 14), Powasan virus (Seq. ID. 15), Langat virus (Seq. ID. 16), Murray Valley Encephalitis virus (Seq. ID. 17) and St. Louis Encephalitis virus (Seq. ID. 18).

Example 9

Peptide HDIII2CL Modifies the Interaction of A2MR and RAPR13 with the A2MR Receptor.

In order to obtain a direct evidence of the interaction with the A2MR receptor, the effect of one of the designed peptides on the binding of the natural ligands of A2MR to Vero cells was investigated. The assay was performed with fluoresceinated A2M and RAPR13, measuring their binding to Vero cells in the presence of increasing concentrations of the HDIII2CL peptide. The amount of protein bound to the cells was estimated by flow cytometry, using recombinant human EGF (rhEGF) as a negative control for the experiment, since it is known that Vero cells express the EGF receptor in their surface (Copp J, Wiley S, Ward M W, van der Geer P (2005) *Hypertonic shock inhibits growth factor receptor signaling, induces caspase*-3 *activation, and causes reversible fragmentation of the mitochondrial network. Am J Physiol Cell Physiol.* 288:C403-15).

Figure 19:
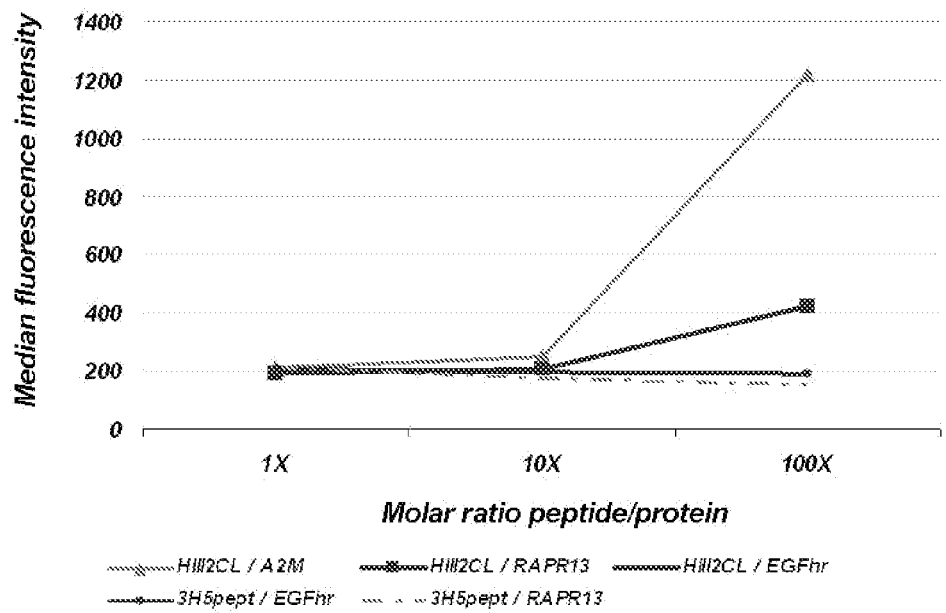

FIG. 19 shows how the presence of the HDIII2CL peptide increases the amount of surface-bound A2M and RAPR13, having however no effect on the binding of rhEGF. The presence of peptide 3H5pept, employed as a control for the assay, does not produce variations in the amount of surface-bound RAPR13. These results indicate that the influence of the HDIII2CL peptide on the interaction of A2M and RAPR13 with their cellular receptors is specific for these molecules. However, the fact that the observed effect is an increase, rather than a decrease in binding of the ligands to the cells, suggests that the peptide does not bind the same site on the receptor as these molecules. In that case, the observed effect can be ascribed to conformational changes triggered by binding of the peptide that favor the binding of A2M or RAPR13. The modulation of the interaction of a ligand due to an allosteric effect mediated by the binding of a different ligand is a real possibility, considering the organization of this receptor into multiple ligand binding domains (Herz J, Strickland D K. (2001) *LRP: a multifunctional scavenger and signaling receptor. J Clin Invest.* 108:779-84). As a matter of fact, this same mechanism is invoked to explain the inhibition by RAP of the binding and/or the internalization of A2MR ligands that actually bind to A2MR domains that are notably distant in its structure from those occupied by RAP.

Example 10

Inhibition of DV Infection by Activated A2M is Mediated by In-solution Interaction with the Virus.

To obtain further evidences of the interaction of DV with A2M, the two variants of the protein i.e. activated and non-activated were used in assays of inhibition of infection of Vero cells. The viral preparation was incubated with solutions of activated A2M of higher concentrations than the physiological concentrations reached by this variant of the protein. Solutions of equimolar concentration of non-activated A2M and a non-related protein were used as negative controls.

Figure 20:
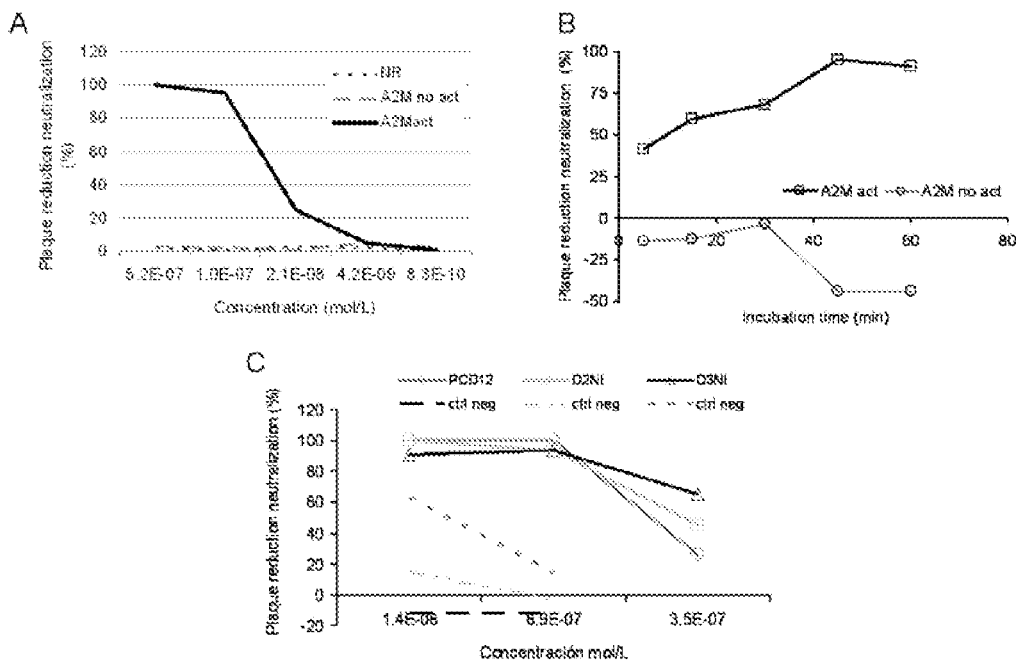

In FIG. 20A is observed that the pre-incubation of the virus with increasing concentrations of activated A2M blocks viral infection in a dose-dependent manner. A very interesting result is the fact that the concentration of activated A2M that inhibits 50% of viral infection in Vero cells corresponds with the affinity constant determined for the interaction of the activated A2M with the protein DIIIE2J (kD $10^{-7}$ mol/L, see example 3 and FIG. 6D). This result suggests that in this experiment the inhibition of infection is mediated by the interaction of the activated A2M with the virus rather than because of a competition for the binding to the A2MR in the cell surface. Activated-A2M also inhibited infection of Vero cells by serotypes 1 and 3 of DV (FIG. 20C).

In order to confirm that the inhibition of infection was due to the in-solution interaction of the virus with activated A2M, both variants of the protein were incubated for increasing intervals of time with the viral preparation before incubation with the cells. The results in FIG. 20B show that the inhibitory effect depends on the time of incubation which is corresponding with an inhibition mediated by the direct interaction of the protein with the virus particle. Interestingly, for incubation times longer than 30 minutes, non-activated A2M increase viral infection up to a 50%. This result suggests that small amounts of activated A2M generated during incubation were able to increase the efficiency of the infection. In fact, this situation reflects better what could be the actual physiological situation for the interaction of the virus with the A2M in vivo where the activated A2M circulates in trace amounts due to the high efficiency of the A2MR in the clearance of A2M-protease complexes (Li Y, Lu W, Marzolo M P, Bu G (2001) *Differential functions of members of the low density lipoprotein receptor family suggested by their distinct endocytosis rates. J Biol Chem.* 276: 18000-18006; Verges M, Bensadoun A, Herz J, Belcher J D, Havel R J (2004) *Endocytosis of hepatic lipase and lipoprotein lipase into rat liver hepatocytes in vivo is mediated by the low density lipoprotein receptor-related protein. J Biol Chem.* 279: 9030-9036).

Example 11

Purified A2MR Inhibits Infection of DV to Vero Cells.

We also addressed whether soluble A2MR is able to inhibit DV infection. To this purpose, the α-chain of the receptor was purified from human plasma of healthy donors where this protein is known to circulate in a range of concentrations of 3.7-10.8 μg/mL (Quinn K A, Grimsley P G, Dai Y P, Tapner M, Chesterman C N, Owensby D A (1997) *Soluble low density lipoprotein receptor-related protein (LRP) circulates in human plasma. J Biol Chem.* 272:23946-23951). Samples of 300 mL of frozen human plasma were pre-fractionated by ion exchange chromatography using a column packed with DE-52 (Whatman, UK) and equilibrated with Tris 50 mM, 60 mM NaCl, 1 mM EDTA pH 6. The fractions were eluted by a step gradient of increasing concentrations of NaCl and tested for the presence of A2MR by a ligand-blott analysis with bioinilated ligands (i.e. MeNH$_2$_A2M and RAPR13). The binding of biotinilated ligands was detected using a sptrepta-vidin-peroxidase conjugate.

Figure 21:
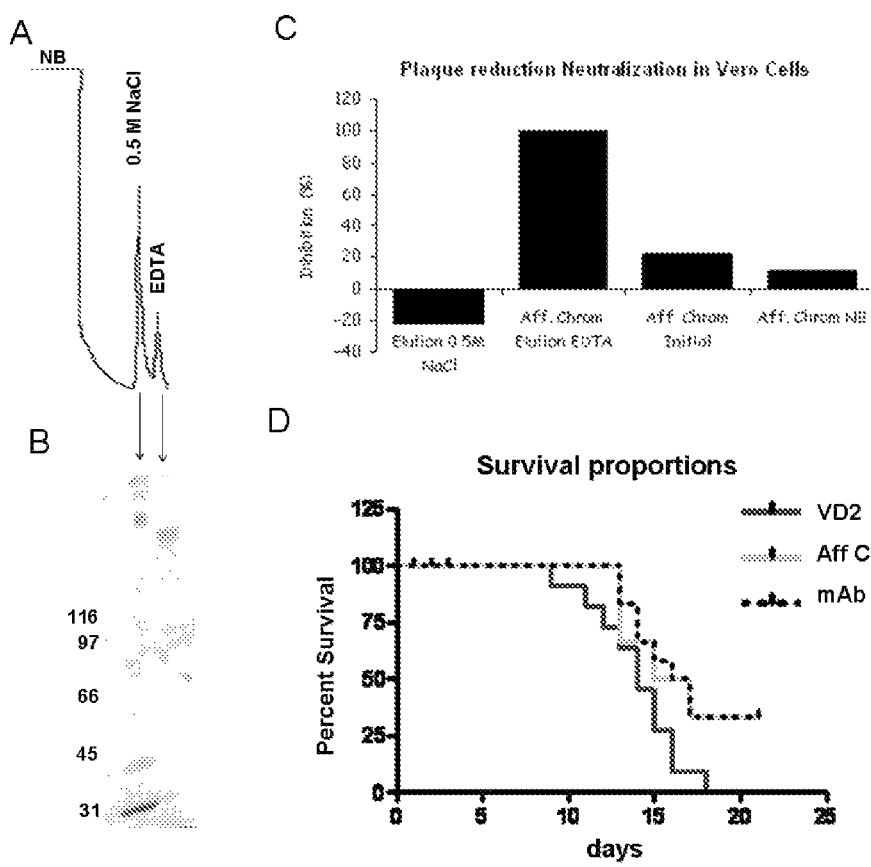

Receptor-containing fractions were dialized aganist buffer Tris 50 mM, 120 mM NaCl pH 7.4, 1 mM CaCl2, 0.05% Tween 20 and loaded to a column with inmobilized MeNH2_A2M, a ligand uniquely recognized by A2MR among the members of LDLR family. Previous to the elution of the receptor, the column was extensively washed with the equilibration buffer but containing 0.5 M NaCl. For the specific elution of the A2MR was used buffer Tris 50 mM, 0.5 M NaCl pH 6, 10 mM EDTA, 0.05% Tween 20 (FIG. 21A). The different fractions from the affinity chromatography were dialyzed against PBS pH 7.4, 1 mM CaCl$_2$ and sterilized by filtration trough 0.2 μM.

The SDS-PAGE analysis exhibits a differential pattern of proteins bands in both fractions i.e. the fraction eluted with 0.5M NaCl and the fraction corresponding to the specific conditions for the elution of the A2MR. The later fraction shows a single protein band that migrates to a position corresponding with the molecular mass of the α-chain of the A2MR (400-500 kDa) (FIG. 21B).

The affinity chromatography fractions were evaluated in a DV2-plaque reduction neutralization assay in vero cells. To this aim, a viral preparation containing 100 infective viral particles was pre-incubated with the different fractions at a protein concentration of 25 μg/mL for 1 hour at 25° C. Next, the virus was added to Vero cell monolayers and infection was allowed to occur for 45 minutes at 37° C. Afterwards virus/protein mixtures were removed, the cells were washed with fresh medium and finally the cells were incubated for 5 days at 37° C. in high density medium.

The results of this assay showed a potent neutralization of the infection of DV2 with the fraction corresponding to the conditions for the specific elution of the receptor (FIG. 21C). This fraction also exhibited a significative protective effect in a model of mice encephalitis induced by intra-cranial infection of lethal dosis of DV2 (FIG. 21D). In fact, the level of protection was similar to the one obtained by the pre-incubation of the virus with the potent neutralizing mAb 4G2 at 25 μg/mL.

Example 12

The Peptide HDIII3CL Protects from Dengue Encephalitis in the Mouse Model.

The mouse model of dengue encephalitis was used to investigate the potential of the peptide HDIII3CL to protect against DV2 infection. A group of 12 mice were inoculated with lethal dosis of DV2 in combination with 15 μg and 1.5 μg of HDIII3CL peptide. As negative control was used a peptide composed by fragment of 14 aminoacids of a sequence with known heparin binding activity followed by 16 aminoacids of a sequence non-related to the envelope protein of DV. The negative control peptide was used in an equimolar amount to the highest dose of the peptide HDIII3CL. Another group was inoculated with the same viral preparation but pre-incuabted with mAb 4G2 at 25 μg/mL as positive control of protection.

Figure 22:
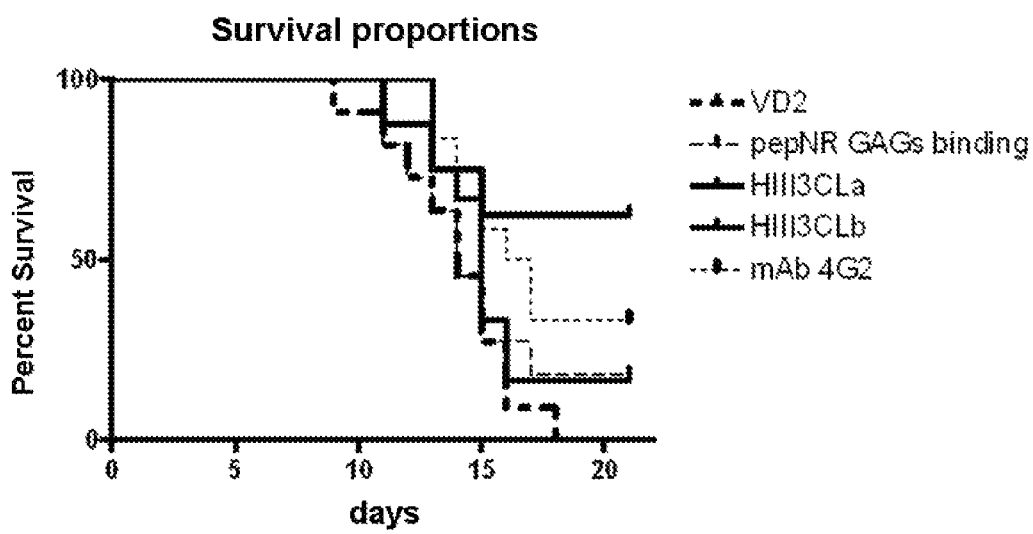

As can be observed in FIG. 22, the peptide HDIII3CL was able to protect 56% of mice for the inoculated with the highest dose of the peptide. The group corresponding to the 1.5 μg of the peptide per animal exhibited a similar level of protection to the heparin-binding peptide with no statistically significant difference from the group inoculated with virus alone as evaluated by the and Kaplan-Meier statistics (log rank test).

The protection of the peptide HDIII3CL against a lethal challenge with DV2 along with the evidence that this peptide is capable of inhibit DV infection in an in vivo model is also confirming the capabiblity of the peptide to protect against infection with a heterologous serotype of DV.

Incorporation of Sequence Listing

Incorporated herein by reference in its entirety is the Sequence Listing for the application. The Sequence Listing is disclosed on a computer-readable ASCII text file titled, "sequence listing4", created on Nov. 8, 2012. The sequence listing.txt file is 107 kb in size.

The invention claimed is:

1. A method for blocking the infection by flaviviruses, said method comprising interfering with the interaction of the viral envelope protein with the alpha-2 macroglobulin receptor identified in the sequence listing as SEQ ID NO: 3, wherein the agent that interferes with the interaction of the virus with the receptor is the peptide identified as SEQ ID NO: 7.

2. A method according to claim 1 wherein the flavivirus is the dengue virus, the Yellow Fever Virus, the Japanese Encephalitis virus, the Tick-Borne Encephalitis virus, the Murray Valley Encephalitis virus, the West Nile Virus, the Kunjin virus, the Powasan virus, the Langat virus or the Saint Louis Encephalitis virus.

3. A method according to claim 1 wherein the sequence of the viral protein is at least 60% homologous to the sequence identified in the sequence listing as SEQ ID NO: 1.

4. A method according to claim 1 wherein the agent that interferes with the interaction of the viral envelope protein with the protein identified in the sequence listing as SEQ ID NO: 3 is obtained by chemical synthesis, or by recombinant DNA techniques, or from a natural source.

5. A method according to claim 1 wherein said peptide is modified to include
   an optional N-terminal extension formed by a chemical group covalently bonded to the N-terminal group cysteine;
   and an optional C-terminal extension formed by a chemical group covalently bonded to the terminal carbonyl group of the C-terminal cysteine; wherein the N-terminal cysteine and C-terminal cysteine form a disulphide bridge.

6. A method according to claim 1 wherein the agent that blocks the infection interferes with the interaction of the protein identified in the sequence listing as SEQ ID NO: 1 with one or more of the residues defined as a ligand binding patch of the protein identified in the sequence listing as SEQ ID NO: 3.

7. A method according to claim 1 wherein the agent interfering with the viral interaction is the active principle of a pharmaceutical composition.

8. The method according to claim 5, wherein the chemical group convalently bonded to the N-terminal or C-terminal cysteine is selected from the group consisting of an acetyl group, methyl group, acyl group, or polyethylene glycol.

* * * * *

UNITED STATES PATENT AND TRADEMARK OFFICE
CERTIFICATE OF CORRECTION

PATENT NO. : 8,420,311 B2
APPLICATION NO. : 12/298808
DATED : April 16, 2013
INVENTOR(S) : Galindo et al.

Page 1 of 2

It is certified that error appears in the above-identified patent and that said Letters Patent is hereby corrected as shown below:

In the Specification

Column 4, line 47

Now reads: "to domain II of dengue";

Should read: -- to domain III of dengue --.

Column 10, line 23-24

Now reads: "For example, in may";

Should read: -- For example, it may --.

Column 13, line 52

Now reads: "30ng/mL";

Should read: -- 30 µg/mL --.

Column 14, line 9

Now reads: "0.5 pg/well";

Should read: -- 0.5 µg/well --.

Signed and Sealed this
Seventeenth Day of September, 2013

Teresa Stanek Rea
*Deputy Director of the United States Patent and Trademark Office*

CERTIFICATE OF CORRECTION (continued)
U.S. Pat. No. 8,420,311 B2

In the Specification

Column 15, line 50

Now reads:    "chormatography";

Should read:    -- chromatography --.

Column 36, line 32

Now reads:    "pre-incuabted";

Should read:    -- pre-incubated --.

SEQUENCE LISTING

<160> NUMBER OF SEQ ID NOS: 91

<210> SEQ ID NO 1
<211> LENGTH: 495
<212> TYPE: PRT
<213> ORGANISM: Dengue virus type 2

<400> SEQUENCE: 1

Met Arg Cys Ile Gly Ile Ser Asn Arg Asp Phe Val Glu Gly Val Ser
 1               5                   10                  15

-continued

```
Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Leu Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Val Val Leu Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asp Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Gly Val Glu Pro
    370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
        435                 440                 445
```

```
Ser Gly Val Ser Trp Thr Met Lys Ile Leu Ile Gly Val Ile Ile Thr
    450                 455                 460
Trp Ile Gly Met Asn Ser Arg Ser Thr Ser Leu Ser Val Ser Leu Val
465                 470                 475                 480
Leu Val Gly Val Val Thr Leu Tyr Leu Gly Ala Met Val Gln Ala
                485                 490                 495

<210> SEQ ID NO 2
<211> LENGTH: 1474
<212> TYPE: PRT
<213> ORGANISM: Homo sapiens

<400> SEQUENCE: 2

Met Gly Lys Asn Lys Leu Leu His Pro Ser Leu Val Leu Leu Leu Leu
  1               5                  10                  15
Val Leu Leu Pro Thr Asp Ala Ser Val Ser Gly Lys Pro Gln Tyr Met
             20                  25                  30
Val Leu Val Pro Ser Leu Leu His Thr Glu Thr Thr Glu Lys Gly Cys
         35                  40                  45
Val Leu Leu Ser Tyr Leu Asn Glu Thr Val Thr Val Ser Ala Ser Leu
     50                  55                  60
Glu Ser Val Arg Gly Asn Arg Ser Leu Phe Thr Asp Leu Glu Ala Glu
 65                  70                  75                  80
Asn Asp Val Leu His Cys Val Ala Phe Ala Val Pro Lys Ser Ser Ser
                 85                  90                  95
Asn Glu Glu Val Met Phe Leu Thr Val Gln Val Lys Gly Pro Thr Gln
            100                 105                 110
Glu Phe Lys Lys Arg Thr Thr Val Met Val Lys Asn Glu Asp Ser Leu
        115                 120                 125
Val Phe Val Gln Thr Asp Lys Ser Ile Tyr Lys Pro Gly Gln Thr Val
    130                 135                 140
Lys Phe Arg Val Val Ser Met Asp Glu Asn Phe His Pro Leu Asn Glu
145                 150                 155                 160
Leu Ile Pro Leu Val Tyr Ile Gln Asp Pro Lys Gly Asn Arg Ile Ala
                165                 170                 175
Gln Trp Gln Ser Phe Gln Leu Glu Gly Gly Leu Lys Gln Phe Ser Phe
            180                 185                 190
Pro Leu Ser Ser Glu Pro Phe Gln Gly Ser Tyr Lys Val Val Val Gln
        195                 200                 205
Lys Lys Ser Gly Gly Arg Thr Glu His Pro Phe Thr Val Glu Glu Phe
    210                 215                 220
Val Leu Pro Lys Phe Glu Val Gln Val Thr Val Pro Lys Ile Ile Thr
225                 230                 235                 240
Ile Leu Glu Glu Glu Met Asn Val Ser Val Cys Gly Leu Tyr Thr Tyr
                245                 250                 255
Gly Lys Pro Val Pro Gly His Val Thr Val Ser Ile Cys Arg Lys Tyr
            260                 265                 270
Ser Asp Ala Ser Asp Cys His Gly Glu Asp Ser Gln Ala Phe Cys Glu
        275                 280                 285
Lys Phe Ser Gly Gln Leu Asn Ser His Gly Cys Phe Tyr Gln Gln Val
    290                 295                 300
Lys Thr Lys Val Phe Gln Leu Lys Arg Lys Glu Tyr Glu Met Lys Leu
305                 310                 315                 320
His Thr Glu Ala Gln Ile Gln Glu Glu Gly Thr Val Val Glu Leu Thr
                325                 330                 335
```

```
Gly Arg Gln Ser Ser Glu Ile Thr Arg Thr Ile Thr Lys Leu Ser Phe
                340                 345                 350

Val Lys Val Asp Ser His Phe Arg Gln Gly Ile Pro Phe Phe Gly Gln
            355                 360                 365

Val Arg Leu Val Asp Gly Lys Gly Val Pro Ile Pro Asn Lys Val Ile
        370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His His Thr Ala
        435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Gly Leu Lys Lys Leu Ser Phe Tyr
                485                 490                 495

Tyr Leu Ile Met Ala Lys Gly Gly Ile Val Arg Thr Gly Thr His Gly
            500                 505                 510

Leu Leu Val Lys Gln Glu Asp Met Lys Gly His Phe Ser Ile Ser Ile
        515                 520                 525

Pro Val Lys Ser Asp Ile Ala Pro Val Ala Arg Leu Leu Ile Tyr Ala
    530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
        595                 600                 605

Pro Asp Ala Glu Leu Ser Ala Ser Ser Val Tyr Asn Leu Leu Pro Glu
    610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
            660                 665                 670

Met Gly Leu Lys Ala Phe Thr Asn Ser Lys Ile Arg Lys Pro Lys Met
        675                 680                 685

Cys Pro Gln Leu Gln Gln Tyr Glu Met His Gly Pro Glu Gly Leu Arg
    690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Asn Ser Ala Gly Val Ala
            740                 745                 750

Glu Val Gly Val Thr Val Pro Asp Thr Ile Thr Glu Trp Lys Ala Gly
```

```
                755                 760                 765
Ala Phe Cys Leu Ser Glu Asp Ala Gly Leu Gly Ile Ser Ser Thr Ala
770                 775                 780

Ser Leu Arg Ala Phe Gln Pro Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815

Tyr Leu Pro Lys Cys Ile Arg Val Ser Val Gln Leu Glu Ala Ser Pro
            820                 825                 830

Ala Phe Leu Ala Val Pro Val Glu Lys Glu Gln Ala Pro His Cys Ile
            835                 840                 845

Cys Ala Asn Gly Arg Gln Thr Val Ser Trp Ala Val Thr Pro Lys Ser
850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
            900                 905                 910

Glu Thr Thr Phe Asn Ser Leu Leu Cys Pro Ser Gly Gly Glu Val Ser
            915                 920                 925

Glu Glu Leu Ser Leu Lys Leu Pro Pro Asn Val Val Glu Glu Ser Ala
930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
            980                 985                 990

Thr Gln Gln Leu Thr Pro Glu Val Lys Ser Lys Ala Ile Gly Tyr Leu
            995                 1000                1005

Asn Thr Gly Tyr Gln Arg Gln Leu Asn Tyr Lys His Tyr Asp Gly Ser
1010                1015                1020

Tyr Ser Thr Phe Gly Glu Arg Tyr Gly Arg Asn Gln Gly Asn Thr Trp
1025                1030                1035                1040

Leu Thr Ala Phe Val Leu Lys Thr Phe Ala Gln Ala Arg Ala Tyr Ile
                1045                1050                1055

Phe Ile Asp Glu Ala His Ile Thr Gln Ala Leu Ile Trp Leu Ser Gln
            1060                1065                1070

Arg Gln Lys Asp Asn Gly Cys Phe Arg Ser Ser Gly Ser Leu Leu Asn
            1075                1080                1085

Asn Ala Ile Lys Gly Gly Val Glu Asp Glu Val Thr Leu Ser Ala Tyr
            1090                1095                1100

Ile Thr Ile Ala Leu Leu Glu Ile Pro Leu Thr Val Thr His Pro Val
1105                1110                1115                1120

Val Arg Asn Ala Leu Phe Cys Leu Glu Ser Ala Trp Lys Thr Ala Gln
                1125                1130                1135

Glu Gly Asp His Gly Ser His Val Tyr Thr Lys Ala Leu Leu Ala Tyr
            1140                1145                1150

Ala Phe Ala Leu Ala Gly Asn Gln Asp Lys Arg Lys Glu Val Leu Lys
            1155                1160                1165

Ser Leu Asn Glu Glu Ala Val Lys Lys Asp Asn Ser Val His Trp Glu
            1170                1175                1180
```

-continued

```
Arg Pro Gln Lys Pro Lys Ala Pro Val Gly His Phe Tyr Glu Pro Gln
1185                1190                1195                1200

Ala Pro Ser Ala Glu Val Glu Met Thr Ser Tyr Val Leu Leu Ala Tyr
         1205                1210                1215

Leu Thr Ala Gln Pro Ala Pro Thr Ser Glu Asp Leu Thr Ser Ala Thr
     1220                1225                1230

Asn Ile Val Lys Trp Ile Thr Lys Gln Gln Asn Ala Gln Gly Gly Phe
 1235                1240                1245

Ser Ser Thr Gln Asp Thr Val Val Ala Leu His Ala Leu Ser Lys Tyr
   1250                1255                1260

Gly Ala Ala Thr Phe Thr Arg Thr Gly Lys Ala Ala Gln Val Thr Ile
1265                1270                1275                1280

Gln Ser Ser Gly Thr Phe Ser Ser Lys Phe Gln Val Asp Asn Asn Asn
         1285                1290                1295

Arg Leu Leu Leu Gln Gln Val Ser Leu Pro Glu Leu Pro Gly Glu Tyr
     1300                1305                1310

Ser Met Lys Val Thr Gly Glu Gly Cys Val Tyr Leu Gln Thr Ser Leu
 1315                1320                1325

Lys Tyr Asn Ile Leu Pro Glu Lys Glu Glu Phe Pro Phe Ala Leu Gly
 1330                1335                1340

Val Gln Thr Leu Pro Gln Thr Cys Asp Glu Pro Lys Ala His Thr Ser
1345                1350                1355                1360

Phe Gln Ile Ser Leu Ser Val Ser Tyr Thr Gly Ser Arg Ser Ala Ser
         1365                1370                1375

Asn Met Ala Ile Val Asp Val Lys Met Val Ser Gly Phe Ile Pro Leu
     1380                1385                1390

Lys Pro Thr Val Lys Met Leu Glu Arg Ser Asn His Val Ser Arg Thr
 1395                1400                1405

Glu Val Ser Ser Asn His Val Leu Ile Tyr Leu Asp Lys Val Ser Asn
 1410                1415                1420

Gln Thr Leu Ser Leu Phe Phe Thr Val Leu Gln Asp Val Pro Val Arg
1425                1430                1435                1440

Asp Leu Lys Pro Ala Ile Val Lys Val Tyr Asp Tyr Tyr Glu Thr Asp
         1445                1450                1455

Glu Phe Ala Ile Ala Glu Tyr Asn Ala Pro Cys Ser Lys Asp Leu Gly
     1460                1465                1470

Asn Ala

<210> SEQ ID NO 3
<211> LENGTH: 5144
<212> TYPE: PRT
<213> ORGANISM: Homo sapiens

<400> SEQUENCE: 3

Met Gly Lys Asn Lys Leu Leu His Pro Ser Leu Val Leu Leu Leu Leu
 1               5                  10                  15

Val Leu Leu Pro Thr Asp Ala Ser Val Ser Gly Lys Pro Gln Tyr Met
             20                  25                  30

Val Leu Val Pro Ser Leu Leu His Thr Glu Thr Thr Glu Lys Gly Cys
         35                  40                  45

Val Leu Leu Ser Tyr Leu Asn Glu Thr Val Thr Val Ser Ala Ser Leu
     50                  55                  60

Glu Ser Val Arg Gly Asn Arg Ser Leu Phe Thr Asp Leu Glu Ala Glu
 65                  70                  75                  80

Asn Asp Val Leu His Cys Val Ala Phe Ala Val Pro Lys Ser Ser Ser
```

```
                85                  90                  95
Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
        290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
        355                 360                 365

Val Arg Leu Val Asp Gly Lys Gly Val Pro Ile Pro Asn Lys Val Ile
        370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Ala His His Thr Ala
        435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
            500                 505                 510
```

```
Leu Leu Val Lys Gln Glu Asp Met Lys Gly His Phe Ser Ile Ser Ile
            515                 520                 525

Pro Val Lys Ser Asp Ile Ala Pro Val Ala Arg Leu Leu Ile Tyr Ala
530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
            580                 585                 590

Ser Val Cys Ala Leu Arg Ala Val Met Leu Thr Pro Pro Leu Leu Leu
        595                 600                 605

Leu Leu Pro Leu Leu Ser Ala Leu Val Ala Ala Ile Asp Ala Pro
610                 615                 620

Lys Thr Cys Ser Pro Lys Gln Phe Ala Cys Arg Asp Gln Ile Thr Cys
625                 630                 635                 640

Ile Ser Lys Gly Trp Arg Cys Asp Gly Glu Arg Asp Cys Pro Asp Gly
                645                 650                 655

Ser Asp Glu Ala Pro Glu Ile Cys Pro Gln Ser Lys Ala Gln Arg Cys
            660                 665                 670

Gln Pro Asn Glu His Asn Cys Leu Gly Thr Glu Leu Cys Val Pro Met
        675                 680                 685

Ser Arg Leu Cys Asn Gly Val Gln Asp Cys Met Asp Gly Ser Asp Glu
    690                 695                 700

Gly Pro His Cys Arg Glu Leu Gln Gly Asn Cys Ser Arg Leu Gly Cys
705                 710                 715                 720

Gln His His Cys Val Pro Thr Leu Asp Gly Pro Thr Cys Tyr Cys Asn
                725                 730                 735

Ser Ser Phe Gln Leu Gln Ala Asp Gly Lys Thr Cys Lys Asp Phe Asp
            740                 745                 750

Glu Cys Ser Val Tyr Gly Thr Cys Ser Gln Leu Cys Thr Asn Thr Asp
        755                 760                 765

Gly Ser Phe Ile Cys Gly Cys Val Glu Gly Tyr Leu Leu Gln Pro Asp
    770                 775                 780

Asn Arg Ser Cys Lys Ala Lys Asn Glu Pro Val Asp Arg Pro Pro Val
785                 790                 795                 800

Leu Leu Ile Ala Asn Ser Gln Asn Ile Leu Ala Thr Tyr Leu Ser Gly
                805                 810                 815

Ala Gln Val Ser Thr Ile Thr Pro Thr Ser Thr Arg Gln Thr Thr Ala
            820                 825                 830

Met Asp Phe Ser Tyr Ala Asn Glu Thr Val Cys Trp Val His Val Gly
        835                 840                 845

Asp Ser Ala Ala Gln Thr Gln Leu Lys Cys Ala Arg Met Pro Gly Leu
    850                 855                 860

Lys Gly Phe Val Asp Glu His Thr Ile Asn Ile Ser Leu Ser Leu His
865                 870                 875                 880

His Val Glu Gln Met Ala Ile Asp Trp Leu Thr Gly Asn Phe Tyr Phe
                885                 890                 895

Val Asp Asp Ile Asp Asp Arg Ile Phe Val Cys Asn Arg Asn Gly Asp
            900                 905                 910

Thr Cys Val Thr Leu Leu Asp Leu Glu Leu Tyr Asn Pro Lys Gly Ile
        915                 920                 925

Ala Leu Asp Pro Ala Met Gly Lys Val Phe Phe Thr Asp Tyr Gly Gln
    930                 935                 940
```

```
Ile Pro Lys Val Glu Arg Cys Asp Met Asp Gly Gln Asn Arg Thr Lys
945                 950                 955                 960

Leu Val Asp Ser Lys Ile Val Phe Pro His Gly Ile Thr Leu Asp Leu
            965                 970                 975

Val Ser Arg Leu Val Tyr Trp Ala Asp Ala Tyr Leu Asp Tyr Ile Glu
        980                 985                 990

Val Val Asp Tyr Glu Gly Lys Gly Arg Gln Thr Ile Ile Gln Gly Ile
            995                 1000                1005

Leu Ile Glu His Leu Tyr Gly Leu Thr Val Phe Glu Asn Tyr Leu Tyr
        1010                1015                1020

Ala Thr Asn Ser Asp Asn Ala Asn Ala Gln Gln Lys Thr Ser Val Ile
1025                1030                1035                1040

Arg Val Asn Arg Phe Asn Ser Thr Glu Tyr Gln Val Val Thr Arg Val
            1045                1050                1055

Asp Lys Gly Gly Ala Leu His Ile Tyr His Gln Arg Arg Gln Pro Arg
        1060                1065                1070

Val Arg Ser His Ala Cys Glu Asn Asp Gln Tyr Gly Lys Pro Gly Gly
        1075                1080                1085

Cys Ser Asp Ile Cys Leu Leu Ala Asn Ser His Lys Ala Arg Thr Cys
    1090                1095                1100

Arg Cys Arg Ser Gly Phe Ser Leu Gly Ser Asp Gly Lys Ser Cys Lys
1105                1110                1115                1120

Lys Pro Glu His Glu Leu Phe Leu Val Tyr Gly Lys Gly Arg Pro Gly
            1125                1130                1135

Ile Ile Arg Gly Met Asp Met Gly Ala Lys Val Pro Asp Glu His Met
        1140                1145                1150

Ile Pro Ile Glu Asn Leu Met Asn Pro Arg Ala Leu Asp Phe His Ala
    1155                1160                1165

Glu Thr Gly Phe Ile Tyr Phe Ala Asp Thr Thr Ser Tyr Leu Ile Gly
    1170                1175                1180

Arg Gln Lys Ile Asp Gly Thr Glu Arg Glu Thr Ile Leu Lys Asp Gly
1185                1190                1195                1200

Ile His Asn Val Glu Gly Val Ala Val Asp Trp Met Gly Asp Asn Leu
        1205                1210                1215

Tyr Trp Thr Asp Asp Gly Pro Lys Lys Thr Ile Ser Val Ala Arg Leu
    1220                1225                1230

Glu Lys Ala Ala Gln Thr Arg Lys Thr Leu Ile Glu Gly Lys Met Thr
1235                1240                1245

His Pro Arg Ala Ile Val Val Asp Pro Leu Asn Gly Trp Met Tyr Trp
1250                1255                1260

Thr Asp Trp Glu Glu Asp Pro Lys Asp Ser Arg Arg Gly Arg Leu Glu
1265                1270                1275                1280

Arg Ala Trp Met Asp Gly Ser His Arg Asp Ile Phe Val Thr Ser Lys
            1285                1290                1295

Thr Val Leu Trp Pro Asn Gly Leu Ser Leu Asp Ile Pro Ala Gly Arg
        1300                1305                1310

Leu Tyr Trp Val Asp Ala Phe Tyr Asp Arg Ile Glu Thr Ile Leu Leu
    1315                1320                1325

Asn Gly Thr Asp Arg Lys Ile Val Tyr Glu Gly Pro Glu Leu Asn His
    1330                1335                1340

Ala Phe Gly Leu Cys His His Gly Asn Tyr Leu Phe Trp Thr Glu Tyr
1345                1350                1355                1360

Arg Ser Gly Ser Val Tyr Arg Leu Glu Arg Gly Val Gly Gly Ala Pro
```

Pro Thr Val Thr Leu Leu Arg Ser Glu Arg Pro Ile Phe Glu Ile
1380                1385                1390

Arg Met Tyr Asp Ala Gln Gln Gln Val Gly Thr Asn Lys Cys Arg
1395                1400                1405

Val Asn Asn Gly Gly Cys Ser Ser Leu Cys Leu Ala Thr Pro Gly Ser
1410                1415                1420

Arg Gln Cys Ala Cys Ala Glu Asp Gln Val Leu Asp Ala Asp Gly Val
1425                1430                1435                1440

Thr Cys Leu Ala Asn Pro Ser Tyr Val Pro Pro Pro Gln Cys Gln Pro
1445                1450                1455

Gly Glu Phe Ala Cys Ala Asn Ser Arg Cys Ile Gln Glu Arg Trp Lys
1460                1465                1470

Cys Asp Gly Asp Asn Asp Cys Leu Asp Asn Ser Asp Glu Ala Pro Ala
1475                1480                1485

Leu Cys His Gln His Thr Cys Pro Ser Asp Arg Phe Lys Cys Glu Asn
1490                1495                1500

Asn Arg Cys Ile Pro Asn Arg Trp Leu Cys Asp Gly Asp Asn Asp Cys
1505                1510                1515                1520

Gly Asn Ser Glu Asp Glu Ser Asn Ala Thr Cys Ser Ala Arg Thr Cys
1525                1530                1535

Pro Pro Asn Gln Phe Ser Cys Ala Ser Gly Arg Cys Ile Pro Ile Ser
1540                1545                1550

Trp Thr Cys Asp Leu Asp Asp Asp Cys Gly Asp Arg Ser Asp Glu Ser
1555                1560                1565

Ala Ser Cys Ala Tyr Pro Thr Cys Phe Pro Leu Thr Gln Phe Thr Cys
1570                1575                1580

Asn Asn Gly Arg Cys Ile Asn Ile Asn Trp Arg Cys Asp Asn Asp Asn
1585                1590                1595                1600

Asp Cys Gly Asp Asn Ser Asp Glu Ala Gly Cys Ser His Ser Cys Ser
1605                1610                1615

Ser Thr Gln Phe Lys Cys Asn Ser Gly Arg Cys Ile Pro Glu His Trp
1620                1625                1630

Thr Cys Asp Gly Asp Asn Asp Cys Gly Asp Tyr Ser Asp Glu Thr His
1635                1640                1645

Ala Asn Cys Thr Asn Gln Ala Thr Arg Pro Pro Gly Gly Cys His Thr
1650                1655                1660

Asp Glu Phe Gln Cys Arg Leu Asp Gly Leu Cys Ile Pro Leu Arg Trp
1665                1670                1675                1680

Arg Cys Asp Gly Asp Thr Asp Cys Met Asp Ser Ser Asp Glu Lys Ser
1685                1690                1695

Cys Glu Gly Val Thr His Val Cys Asp Pro Ser Val Lys Phe Gly Cys
1700                1705                1710

Lys Asp Ser Ala Arg Cys Ile Ser Lys Ala Trp Val Cys Asp Gly Asp
1715                1720                1725

Asn Asp Cys Glu Asp Asn Ser Asp Glu Glu Asn Cys Glu Ser Leu Ala
1730                1735                1740

Cys Arg Pro Pro Ser His Pro Cys Ala Asn Asn Thr Ser Val Cys Leu
1745                1750                1755                1760

Pro Pro Asp Lys Leu Cys Asp Gly Asn Asp Asp Cys Gly Asp Gly Ser
1765                1770                1775

Asp Glu Gly Glu Leu Cys Asp Gln Cys Ser Leu Asn Asn Gly Gly Cys
1780                1785                1790

-continued

```
Ser His Asn Cys Ser Val Ala Pro Gly Glu Gly Ile Val Cys Ser Cys
    1795                1800                1805
Pro Leu Gly Met Glu Leu Gly Pro Asp Asn His Thr Cys Gln Ile Gln
    1810                1815                1820
Ser Tyr Cys Ala Lys His Leu Lys Cys Ser Gln Lys Cys Asp Gln Asn
1825                1830                1835                1840
Lys Phe Ser Val Lys Cys Ser Cys Tyr Glu Gly Trp Val Leu Glu Pro
            1845                1850                1855
Asp Gly Glu Ser Cys Arg Ser Leu Asp Pro Phe Lys Pro Phe Ile Ile
                1860                1865                1870
Phe Ser Asn Arg His Glu Ile Arg Arg Ile Asp Leu His Lys Gly Asp
    1875                1880                1885
Tyr Ser Val Leu Val Pro Gly Leu Arg Asn Thr Ile Ala Leu Asp Phe
    1890                1895                1900
His Leu Ser Gln Ser Ala Leu Tyr Trp Thr Asp Val Val Glu Asp Lys
1905                1910                1915                1920
Ile Tyr Arg Gly Lys Leu Leu Asp Asn Gly Ala Leu Thr Ser Phe Glu
            1925                1930                1935
Val Val Ile Gln Tyr Gly Leu Ala Thr Pro Glu Gly Leu Ala Val Asp
        1940                1945                1950
Trp Ile Ala Gly Asn Ile Tyr Trp Val Glu Ser Asn Leu Asp Gln Ile
    1955                1960                1965
Glu Val Ala Lys Leu Asp Gly Thr Leu Arg Thr Thr Leu Leu Ala Gly
    1970                1975                1980
Asp Ile Glu His Pro Arg Ala Ile Ala Leu Asp Pro Arg Asp Gly Ile
1985                1990                1995                2000
Leu Phe Trp Thr Asp Trp Asp Ala Ser Leu Pro Arg Ile Glu Ala Ala
            2005                2010                2015
Ser Met Ser Gly Ala Gly Arg Arg Thr Val His Arg Glu Thr Gly Ser
        2020                2025                2030
Gly Gly Trp Pro Asn Gly Leu Thr Val Asp Tyr Leu Glu Lys Arg Ile
    2035                2040                2045
Leu Trp Ile Asp Ala Arg Ser Asp Ala Ile Tyr Ser Ala Arg Tyr Asp
    2050                2055                2060
Gly Ser Gly His Met Glu Val Leu Arg Gly His Glu Phe Leu Ser His
2065                2070                2075                2080
Pro Phe Ala Val Thr Leu Tyr Gly Gly Glu Val Tyr Trp Thr Asp Trp
            2085                2090                2095
Arg Thr Asn Thr Leu Ala Lys Ala Asn Lys Trp Thr Gly His Asn Val
        2100                2105                2110
Thr Val Val Gln Arg Thr Asn Thr Gln Pro Phe Asp Leu Gln Val Tyr
    2115                2120                2125
His Pro Ser Arg Gln Pro Met Ala Pro Asn Pro Cys Glu Ala Asn Gly
    2130                2135                2140
Gly Gln Gly Pro Cys Ser His Leu Cys Leu Ile Asn Tyr Asn Arg Thr
2145                2150                2155                2160
Val Ser Cys Ala Cys Pro His Leu Met Lys Leu His Lys Asp Asn Thr
            2165                2170                2175
Thr Cys Tyr Glu Phe Lys Lys Phe Leu Leu Tyr Ala Arg Gln Met Glu
        2180                2185                2190
Ile Arg Gly Val Asp Leu Asp Ala Pro Tyr Tyr Asn Tyr Ile Ile Ser
    2195                2200                2205
Phe Thr Val Pro Asp Ile Asp Asn Val Thr Val Leu Asp Tyr Asp Ala
    2210                2215                2220
```

```
Arg Glu Gln Arg Val Tyr Trp Ser Asp Val Arg Thr Gln Ala Ile Lys
2225                2230                2235                2240

Arg Ala Phe Ile Asn Gly Thr Gly Val Glu Thr Val Val Ser Ala Asp
            2245                2250                2255

Leu Pro Asn Ala His Gly Leu Ala Val Asp Trp Val Ser Arg Asn Leu
        2260                2265                2270

Phe Trp Thr Ser Tyr Asp Thr Asn Lys Lys Gln Ile Asn Val Ala Arg
    2275                2280                2285

Leu Asp Gly Ser Phe Lys Asn Ala Val Gln Gly Leu Glu Gln Pro
2290                2295                2300

His Gly Leu Val Val His Pro Leu Arg Gly Lys Leu Tyr Trp Thr Asp
2305                2310                2315                2320

Gly Asp Asn Ile Ser Met Ala Asn Met Asp Gly Ser Asn Arg Thr Leu
            2325                2330                2335

Leu Phe Ser Gly Gln Lys Gly Pro Val Gly Leu Ala Ile Asp Phe Pro
        2340                2345                2350

Glu Ser Lys Leu Tyr Trp Ile Ser Ser Gly Asn His Thr Ile Asn Arg
    2355                2360                2365

Cys Asn Leu Asp Gly Ser Gly Leu Glu Val Ile Asp Ala Met Arg Ser
2370                2375                2380

Gln Leu Gly Lys Ala Thr Ala Leu Ala Ile Met Gly Asp Lys Leu Trp
2385                2390                2395                2400

Trp Ala Asp Gln Val Ser Glu Lys Met Gly Thr Cys Ser Lys Ala Asp
            2405                2410                2415

Gly Ser Gly Ser Val Val Leu Arg Asn Ser Thr Thr Leu Val Met His
        2420                2425                2430

Met Lys Val Tyr Asp Glu Ser Ile Gln Leu Asp His Lys Gly Thr Asn
    2435                2440                2445

Pro Cys Ser Val Asn Asn Gly Asp Cys Ser Gln Leu Cys Leu Pro Thr
2450                2455                2460

Ser Glu Thr Thr Arg Ser Cys Met Cys Thr Ala Gly Tyr Ser Leu Arg
2465                2470                2475                2480

Ser Gly Gln Gln Ala Cys Glu Gly Val Gly Ser Phe Leu Leu Tyr Ser
            2485                2490                2495

Val His Glu Gly Ile Arg Gly Ile Pro Leu Asp Pro Asn Asp Lys Ser
        2500                2505                2510

Asp Ala Leu Val Pro Val Ser Gly Thr Ser Leu Ala Val Gly Ile Asp
    2515                2520                2525

Phe His Ala Glu Asn Asp Thr Ile Tyr Trp Val Asp Met Gly Leu Ser
2530                2535                2540

Thr Ile Ser Arg Ala Lys Arg Asp Gln Thr Trp Arg Glu Asp Val Val
2545                2550                2555                2560

Thr Asn Gly Ile Gly Arg Val Glu Gly Ile Ala Val Asp Trp Ile Ala
            2565                2570                2575

Gly Asn Ile Tyr Trp Thr Asp Gln Gly Phe Asp Val Ile Glu Val Ala
        2580                2585                2590

Arg Leu Asn Gly Ser Phe Arg Tyr Val Val Ile Ser Gln Gly Leu Asp
    2595                2600                2605

Lys Pro Arg Ala Ile Thr Val His Pro Glu Lys Gly Tyr Leu Phe Trp
2610                2615                2620

Thr Glu Trp Gly Gln Tyr Pro Arg Ile Glu Arg Ser Arg Leu Asp Gly
2625                2630                2635                2640

Thr Glu Arg Val Val Leu Val Asn Val Ser Ile Ser Trp Pro Asn Gly
```

```
               2645                2650                2655
Ile Ser Val Asp Tyr Gln Asp Gly Lys Leu Tyr Trp Cys Asp Ala Arg
            2660                2665                2670

Thr Asp Lys Ile Glu Arg Ile Asp Leu Glu Thr Gly Glu Asn Arg Glu
        2675                2680                2685

Val Val Leu Ser Ser Asn Asn Met Asp Met Phe Ser Val Ser Val Phe
    2690                2695                2700

Glu Asp Phe Ile Tyr Trp Ser Asp Arg Thr His Ala Asn Gly Ser Ile
2705                2710                2715                2720

Lys Arg Gly Ser Lys Asp Asn Ala Thr Asp Ser Val Pro Leu Arg Thr
            2725                2730                2735

Gly Ile Gly Val Gln Leu Lys Asp Ile Lys Val Phe Asn Arg Asp Arg
        2740                2745                2750

Gln Lys Gly Thr Asn Val Cys Ala Val Ala Asn Gly Gly Cys Gln Gln
    2755                2760                2765

Leu Cys Leu Tyr Arg Gly Arg Gly Gln Arg Ala Cys Ala Cys Ala His
        2770                2775                2780

Gly Met Leu Ala Glu Asp Gly Ala Ser Cys Arg Glu Tyr Ala Gly Tyr
2785                2790                2795                2800

Leu Leu Tyr Ser Glu Arg Thr Ile Leu Lys Ser Ile His Leu Ser Asp
            2805                2810                2815

Glu Arg Asn Leu Asn Ala Pro Val Gln Pro Phe Glu Asp Pro Glu His
        2820                2825                2830

Met Lys Asn Val Ile Ala Leu Ala Phe Asp Tyr Arg Ala Gly Thr Ser
    2835                2840                2845

Pro Gly Thr Pro Asn Arg Ile Phe Phe Ser Asp Ile His Phe Gly Asn
        2850                2855                2860

Ile Gln Gln Ile Asn Asp Asp Gly Ser Arg Arg Ile Thr Ile Val Glu
2865                2870                2875                2880

Asn Val Gly Ser Val Glu Gly Leu Ala Tyr His Arg Gly Trp Asp Thr
            2885                2890                2895

Leu Tyr Trp Thr Ser Tyr Thr Thr Ser Thr Ile Thr Arg His Thr Val
        2900                2905                2910

Asp Gln Thr Arg Pro Gly Ala Phe Glu Arg Glu Thr Val Ile Thr Met
    2915                2920                2925

Ser Gly Asp Asp His Pro Arg Ala Phe Val Leu Asp Glu Cys Gln Asn
        2930                2935                2940

Leu Met Phe Trp Thr Asn Trp Asn Glu Gln His Pro Ser Ile Met Arg
2945                2950                2955                2960

Ala Ala Leu Ser Gly Ala Asn Val Leu Thr Leu Ile Glu Lys Asp Ile
            2965                2970                2975

Arg Thr Pro Asn Gly Leu Ala Ile Asp His Arg Ala Glu Lys Leu Tyr
        2980                2985                2990

Phe Ser Asp Ala Thr Leu Asp Lys Ile Glu Arg Cys Glu Tyr Asp Gly
    2995                3000                3005

Ser His Arg Tyr Val Ile Leu Lys Ser Glu Pro Val His Pro Phe Gly
        3010                3015                3020

Leu Ala Val Tyr Gly Glu His Ile Phe Trp Thr Asp Trp Val Arg Arg
3025                3030                3035                3040

Ala Val Gln Arg Ala Asn Lys His Val Gly Ser Asn Met Lys Leu Leu
            3045                3050                3055

Arg Val Asp Ile Pro Gln Gln Pro Met Gly Ile Ile Ala Val Ala Asn
        3060                3065                3070
```

-continued

```
Asp Thr Asn Ser Cys Glu Leu Ser Pro Cys Arg Ile Asn Asn Gly Gly
    3075                3080                3085

Cys Gln Asp Leu Cys Leu Leu Thr His Gln Gly His Val Asn Cys Ser
    3090                3095                3100

Cys Arg Gly Gly Arg Ile Leu Gln Asp Leu Thr Cys Arg Ala Val
3105                3110                3115                3120

Asn Ser Ser Cys Arg Ala Gln Asp Glu Phe Glu Cys Ala Asn Gly Glu
            3125                3130                3135

Cys Ile Asn Phe Ser Leu Thr Cys Asp Gly Val Pro His Cys Lys Asp
            3140                3145                3150

Lys Ser Asp Glu Lys Pro Ser Tyr Cys Asn Ser Arg Arg Cys Lys Lys
            3155                3160                3165

Thr Phe Arg Gln Cys Ser Asn Gly Arg Cys Val Ser Asn Met Leu Trp
    3170                3175                3180

Cys Asn Gly Ala Asp Asp Cys Gly Asp Gly Ser Asp Glu Ile Pro Cys
3185                3190                3195                3200

Asn Lys Thr Ala Cys Gly Val Gly Glu Phe Arg Cys Arg Asp Gly Thr
            3205                3210                3215

Cys Ile Gly Asn Ser Ser Arg Cys Asn Gln Phe Val Asp Cys Glu Asp
            3220                3225                3230

Ala Ser Asp Glu Met Asn Cys Ser Ala Thr Asp Cys Ser Ser Tyr Phe
    3235                3240                3245

Arg Leu Gly Val Lys Gly Val Leu Phe Gln Pro Cys Glu Arg Thr Ser
    3250                3255                3260

Leu Cys Tyr Ala Pro Ser Trp Val Cys Asp Gly Ala Asn Asp Cys Gly
3265                3270                3275                3280

Asp Tyr Ser Asp Glu Arg Asp Cys Pro Gly Val Lys Arg Pro Arg Cys
            3285                3290                3295

Pro Leu Asn Tyr Phe Ala Cys Pro Ser Gly Arg Cys Ile Pro Met Ser
            3300                3305                3310

Trp Thr Cys Asp Lys Glu Asp Asp Cys Glu His Gly Glu Asp Glu Thr
    3315                3320                3325

His Cys Asn Lys Phe Cys Ser Glu Ala Gln Phe Glu Cys Gln Asn His
    3330                3335                3340

Arg Cys Ile Ser Lys Gln Trp Leu Cys Asp Gly Ser Asp Asp Cys Gly
3345                3350                3355                3360

Asp Gly Ser Asp Glu Ala Ala His Cys Glu Gly Lys Thr Cys Gly Pro
            3365                3370                3375

Ser Ser Phe Ser Cys Pro Gly Thr His Val Cys Val Pro Glu Arg Trp
    3380                3385                3390

Leu Cys Asp Gly Asp Lys Asp Cys Ala Asp Gly Ala Asp Glu Ser Ile
    3395                3400                3405

Ala Ala Gly Cys Leu Tyr Asn Ser Thr Cys Asp Asp Arg Glu Phe Met
    3410                3415                3420

Cys Gln Asn Arg Gln Cys Ile Pro Lys His Phe Val Cys Asp His Asp
3425                3430                3435                3440

Arg Asp Cys Ala Asp Gly Ser Asp Glu Ser Pro Glu Cys Glu Tyr Pro
            3445                3450                3455

Thr Cys Gly Pro Ser Glu Phe Arg Cys Ala Asn Gly Arg Cys Leu Ser
            3460                3465                3470

Ser Arg Gln Trp Glu Cys Asp Gly Glu Asn Asp Cys His Asp Gln Ser
    3475                3480                3485

Asp Glu Ala Pro Lys Asn Pro His Cys Thr Ser Pro Glu His Lys Cys
    3490                3495                3500
```

```
Asn Ala Ser Ser Gln Phe Leu Cys Ser Ser Gly Arg Cys Val Ala Glu
3505                3510                3515                3520

Ala Leu Leu Cys Asn Gly Gln Asp Asp Cys Gly Asp Ser Ser Asp Glu
            3525                3530                3535

Arg Gly Cys His Ile Asn Glu Cys Leu Ser Arg Lys Leu Ser Gly Cys
                3540                3545                3550

Ser Gln Asp Cys Glu Asp Leu Lys Ile Gly Phe Lys Cys Arg Cys Arg
    3555                3560                3565

Pro Gly Phe Arg Leu Lys Asp Asp Gly Arg Thr Cys Ala Asp Val Asp
3570                3575                3580

Glu Cys Ser Thr Thr Phe Pro Cys Ser Gln Arg Cys Ile Asn Thr His
3585                3590                3595                3600

Gly Ser Tyr Lys Cys Leu Cys Val Glu Gly Tyr Ala Pro Arg Gly Gly
            3605                3610                3615

Asp Pro His Ser Cys Lys Ala Val Thr Asp Glu Glu Pro Phe Leu Ile
                3620                3625                3630

Phe Ala Asn Arg Tyr Tyr Leu Arg Lys Leu Asn Leu Asp Gly Ser Asn
    3635                3640                3645

Tyr Thr Leu Leu Lys Gln Gly Leu Asn Asn Ala Val Ala Leu Asp Phe
3650                3655                3660

Asp Tyr Arg Glu Gln Met Ile Tyr Trp Thr Asp Val Thr Thr Gln Gly
3665                3670                3675                3680

Ser Met Ile Arg Arg Met His Leu Asn Gly Ser Asn Val Gln Val Leu
            3685                3690                3695

His Arg Thr Gly Leu Ser Asn Pro Asp Gly Leu Ala Val Asp Trp Val
                3700                3705                3710

Gly Gly Asn Leu Tyr Trp Cys Asp Lys Gly Arg Asp Thr Ile Glu Val
    3715                3720                3725

Ser Lys Leu Asn Gly Ala Tyr Arg Thr Val Leu Val Ser Ser Gly Leu
3730                3735                3740

Arg Glu Pro Arg Ala Leu Val Val Asp Val Gln Asn Gly Tyr Leu Tyr
3745                3750                3755                3760

Trp Thr Asp Trp Gly Asp His Ser Leu Ile Gly Arg Ile Gly Met Asp
            3765                3770                3775

Gly Ser Ser Arg Ser Val Ile Val Asp Thr Lys Ile Thr Trp Pro Asn
                3780                3785                3790

Gly Leu Thr Leu Asp Tyr Val Thr Glu Arg Ile Tyr Trp Ala Asp Ala
    3795                3800                3805

Arg Glu Asp Tyr Ile Glu Phe Ala Ser Leu Asp Gly Ser Asn Arg His
3810                3815                3820

Val Val Leu Ser Gln Asp Ile Pro His Ile Phe Ala Leu Thr Leu Phe
3825                3830                3835                3840

Glu Asp Tyr Val Tyr Trp Thr Asp Trp Glu Thr Lys Ser Ile Asn Arg
            3845                3850                3855

Ala His Lys Thr Thr Gly Thr Asn Lys Thr Leu Leu Ile Ser Thr Leu
                3860                3865                3870

His Arg Pro Met Asp Leu His Val Phe His Ala Leu Arg Gln Pro Asp
    3875                3880                3885

Val Pro Asn His Pro Cys Lys Val Asn Asn Gly Gly Cys Ser Asn Leu
3890                3895                3900

Cys Leu Leu Ser Pro Gly Gly Gly His Lys Cys Ala Cys Pro Thr Asn
3905                3910                3915                3920

Phe Tyr Leu Gly Ser Asp Gly Arg Thr Cys Val Ser Asn Cys Thr Ala
```

-continued

```
                3925                3930                3935
Ser Gln Phe Val Cys Lys Asn Asp Lys Cys Ile Pro Phe Trp Trp Lys
            3940                3945                3950
Cys Asp Thr Glu Asp Asp Cys Gly Asp His Ser Asp Glu Pro Pro Asp
            3955                3960                3965
Cys Pro Glu Phe Lys Cys Arg Pro Gly Gln Phe Gln Cys Ser Thr Gly
            3970                3975                3980
Ile Cys Thr Asn Pro Ala Phe Ile Cys Asp Gly Asp Asn Asp Cys Gln
3985                3990                3995                4000
Asp Asn Ser Asp Glu Ala Asn Cys Asp Ile His Val Cys Leu Pro Ser
                4005                4010                4015
Gln Phe Lys Cys Thr Asn Thr Asn Arg Cys Ile Pro Gly Ile Phe Arg
            4020                4025                4030
Cys Asn Gly Gln Asp Asn Cys Gly Asp Gly Glu Asp Glu Arg Asp Cys
            4035                4040                4045
Pro Glu Val Thr Cys Ala Pro Asn Gln Phe Gln Cys Ser Ile Thr Lys
            4050                4055                4060
Arg Cys Ile Pro Arg Val Trp Val Cys Asp Arg Asp Asn Asp Cys Val
4065                4070                4075                4080
Asp Gly Ser Asp Glu Pro Ala Asn Cys Thr Gln Met Thr Cys Gly Val
                4085                4090                4095
Asp Glu Phe Arg Cys Lys Asp Ser Gly Arg Cys Ile Pro Ala Arg Trp
            4100                4105                4110
Lys Cys Asp Gly Glu Asp Asp Cys Gly Asp Gly Ser Asp Glu Pro Lys
            4115                4120                4125
Glu Glu Cys Asp Glu Arg Thr Cys Glu Pro Tyr Gln Phe Arg Cys Lys
            4130                4135                4140
Asn Asn Arg Cys Val Pro Gly Arg Trp Gln Cys Asp Tyr Asp Asn Asp
4145                4150                4155                4160
Cys Gly Asp Asn Ser Asp Glu Glu Ser Cys Thr Pro Arg Pro Cys Ser
                4165                4170                4175
Glu Ser Glu Phe Ser Cys Ala Asn Gly Arg Cys Ile Ala Gly Arg Trp
            4180                4185                4190
Lys Cys Asp Gly Asp His Asp Cys Ala Asp Gly Ser Asp Glu Lys Asp
            4195                4200                4205
Cys Thr Pro Arg Cys Asp Met Asp Gln Phe Gln Cys Lys Ser Gly His
            4210                4215                4220
Cys Ile Pro Leu Arg Trp Arg Cys Asp Ala Asp Ala Asp Cys Met Asp
4225                4230                4235                4240
Gly Ser Asp Glu Glu Ala Cys Gly Thr Gly Val Arg Thr Cys Pro Leu
                4245                4250                4255
Asp Glu Phe Gln Cys Asn Asn Thr Leu Cys Lys Pro Leu Ala Trp Lys
            4260                4265                4270
Cys Asp Gly Glu Asp Asp Cys Gly Asp Asn Ser Asp Glu Asn Pro Glu
            4275                4280                4285
Glu Cys Ala Arg Phe Val Cys Pro Pro Asn Arg Pro Phe Arg Cys Lys
            4290                4295                4300
Asn Asp Arg Val Cys Leu Trp Ile Gly Arg Gln Cys Asp Gly Thr Asp
            4305                4310                4315                4320
Asn Cys Gly Asp Gly Thr Asp Glu Glu Asp Cys Glu Pro Pro Thr Ala
                4325                4330                4335
His Thr Thr His Cys Lys Asp Lys Lys Glu Phe Leu Cys Arg Asn Gln
                4340                4345                4350
```

-continued

Arg Cys Leu Ser Ser Ser Leu Arg Cys Asn Met Phe Asp Asp Cys Gly
            4355                4360                4365

Asp Gly Ser Asp Glu Glu Asp Cys Ser Ile Asp Pro Lys Leu Thr Ser
        4370                4375                4380

Cys Ala Thr Asn Ala Ser Ile Cys Gly Asp Glu Ala Arg Cys Val Arg
4385                4390                4395                4400

Thr Glu Lys Ala Ala Tyr Cys Ala Cys Arg Ser Gly Phe His Thr Val
        4405                4410                4415

Pro Gly Gln Pro Gly Cys Gln Asp Ile Asn Glu Cys Leu Arg Phe Gly
            4420                4425                4430

Thr Cys Ser Gln Leu Cys Asn Asn Thr Lys Gly Gly His Leu Cys Ser
        4435                4440                4445

Cys Ala Arg Asn Phe Met Lys Thr His Asn Thr Cys Lys Ala Glu Gly
        4450                4455                4460

Ser Glu Tyr Gln Val Leu Tyr Ile Ala Asp Asp Asn Glu Ile Arg Ser
4465                4470                4475                4480

Leu Phe Pro Gly His Pro His Ser Ala Tyr Glu Gln Ala Phe Gln Gly
            4485                4490                4495

Asp Glu Ser Val Arg Ile Asp Ala Met Asp Val His Val Lys Ala Gly
        4500                4505                4510

Arg Val Tyr Trp Thr Asn Trp His Thr Gly Thr Ile Ser Tyr Arg Ser
        4515                4520                4525

Leu Pro Pro Ala Ala Pro Pro Thr Thr Ser Asn Arg His Arg Arg Gln
        4530                4535                4540

Ile Asp Arg Gly Val Thr His Leu Asn Ile Ser Gly Leu Lys Met Pro
4545                4550                4555                4560

Arg Gly Ile Ala Ile Asp Trp Val Ala Gly Asn Val Tyr Trp Thr Asp
            4565                4570                4575

Ser Gly Arg Asp Val Ile Glu Val Ala Gln Met Lys Gly Glu Asn Arg
        4580                4585                4590

Lys Thr Leu Ile Ser Gly Met Ile Asp Glu Pro His Ala Ile Val Val
        4595                4600                4605

Asp Pro Leu Arg Gly Thr Met Tyr Trp Ser Asp Trp Gly Asn His Pro
        4610                4615                4620

Lys Ile Glu Thr Ala Ala Met Asp Gly Thr Leu Arg Glu Thr Leu Val
4625                4630                4635                4640

Gln Asp Asn Ile Gln Trp Pro Thr Gly Leu Ala Val Asp Tyr His Asn
            4645                4650                4655

Glu Arg Leu Tyr Trp Ala Asp Ala Lys Leu Ser Val Ile Gly Ser Ile
        4660                4665                4670

Arg Leu Asn Gly Thr Asp Pro Ile Val Ala Ala Asp Ser Lys Arg Gly
        4675                4680                4685

Leu Ser His Pro Phe Ser Ile Asp Val Phe Glu Asp Tyr Ile Tyr Gly
        4690                4695                4700

Val Thr Tyr Ile Asn Asn Arg Val Phe Lys Ile His Lys Phe Gly His
4705                4710                4715                4720

Ser Pro Leu Val Asn Leu Thr Gly Gly Leu Ser His Ala Ser Asp Val
            4725                4730                4735

Val Leu Tyr His Gln His Lys Gln Pro Glu Val Thr Asn Pro Cys Asp
        4740                4745                4750

Arg Lys Lys Cys Glu Trp Leu Cys Leu Leu Ser Pro Ser Gly Pro Val
        4755                4760                4765

Cys Thr Cys Pro Asn Gly Lys Arg Leu Asp Asn Gly Thr Cys Val Pro
        4770                4775                4780

```
Val Pro Ser Pro Thr Pro Pro Asp Ala Pro Arg Pro Gly Thr Cys
4785                4790                4795                4800

Asn Leu Gln Cys Phe Asn Gly Gly Ser Cys Phe Leu Asn Ala Arg Arg
            4805                4810                4815

Gln Pro Lys Cys Arg Cys Gln Pro Arg Tyr Thr Gly Asp Lys Cys Glu
        4820                4825                4830

Leu Asp Gln Cys Trp Glu His Cys Arg Asn Gly Gly Thr Cys Ala Ala
    4835                4840                4845

Ser Pro Ser Gly Met Pro Thr Cys Arg Cys Pro Thr Gly Phe Thr Gly
4850                4855                4860

Pro Lys Cys Thr Gln Gln Val Cys Ala Gly Tyr Cys Ala Asn Asn Ser
4865                4870                4875                4880

Thr Cys Thr Val Asn Gln Gly Asn Gln Pro Gln Cys Arg Cys Leu Pro
            4885                4890                4895

Gly Phe Leu Gly Asp Arg Cys Gln Tyr Arg Gln Cys Ser Gly Tyr Cys
        4900                4905                4910

Glu Asn Phe Gly Thr Cys Gln Met Ala Ala Asp Gly Ser Arg Gln Cys
    4915                4920                4925

Arg Cys Thr Ala Tyr Phe Glu Gly Ser Arg Cys Glu Val Asn Lys Cys
        4930                4935                4940

Ser Arg Cys Leu Glu Gly Ala Cys Val Val Asn Lys Gln Ser Gly Asp
4945                4950                4955                4960

Val Thr Cys Asn Cys Thr Asp Gly Arg Val Ala Pro Ser Cys Leu Thr
            4965                4970                4975

Cys Val Gly His Cys Ser Asn Gly Gly Ser Cys Thr Met Asn Ser Lys
        4980                4985                4990

Met Met Pro Glu Cys Gln Cys Pro Pro His Met Thr Gly Pro Arg Cys
    4995                5000                5005

Glu Glu His Val Phe Ser Gln Gln Pro Gly His Ile Ala Ser Ile
        5010                5015                5020

Leu Ile Pro Leu Leu Leu Leu Leu Leu Val Leu Val Ala Gly Val
5025                5030                5035                5040

Val Phe Trp Tyr Lys Arg Arg Val Gln Gly Ala Lys Gly Phe Gln His
            5045                5050                5055

Gln Arg Met Thr Asn Gly Ala Met Asn Val Glu Ile Gly Asn Pro Thr
        5060                5065                5070

Tyr Lys Met Tyr Glu Gly Gly Glu Pro Asp Asp Val Gly Gly Leu Leu
    5075                5080                5085

Asp Ala Asp Phe Ala Leu Asp Pro Asp Lys Pro Thr Asn Phe Thr Asn
    5090                5095                5100

Pro Val Tyr Ala Thr Leu Tyr Met Gly Gly His Gly Ser Arg His Ser
5105                5110                5115                5120

Leu Ala Ser Thr Asp Glu Lys Arg Glu Leu Leu Gly Arg Gly Pro Glu
            5125                5130                5135

Asp Glu Ile Gly Asp Pro Leu Ala
            5140

<210> SEQ ID NO 4
<211> LENGTH: 12
<212> TYPE: PRT
<213> ORGANISM: Artificial Sequence
<220> FEATURE:
<221> NAME/KEY: DISULFID
<222> LOCATION: (1)..(12)
<220> FEATURE:
<223> OTHER INFORMATION: Synthetic
```

```
<400> SEQUENCE: 4

Cys Ile Ile Gly Val Glu Pro Gly Gln Leu Lys Cys
 1               5                  10

<210> SEQ ID NO 5
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(18)

<400> SEQUENCE: 5

Cys Ser Tyr Ile Ile Ile Gly Val Glu Pro Gly Gln Leu Lys Leu Asn
 1               5                  10                  15

Trp Cys

<210> SEQ ID NO 6
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(18)

<400> SEQUENCE: 6

Cys Ser Tyr Ile Val Val Gly Ala Gly Glu Lys Ala Leu Lys Leu Ser
 1               5                  10                  15

Trp Cys

<210> SEQ ID NO 7
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(18)

<400> SEQUENCE: 7

Cys Ser Asn Ile Val Ile Gly Ile Gly Asp Lys Ala Leu Lys Ile Asn
 1               5                  10                  15

Trp Cys

<210> SEQ ID NO 8
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(18)

<400> SEQUENCE: 8

Cys Ser Tyr Ile Val Ile Gly Val Gly Asn Ser Ala Leu Thr Leu His
 1               5                  10                  15

Trp Cys

<210> SEQ ID NO 9
```

```
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(18)

<400> SEQUENCE: 9

Cys Ser Tyr Ile Ile Ile Gly Val Glu Pro Gly Gln Ile Lys Ile Asn
 1               5                  10                  15
Trp Cys

<210> SEQ ID NO 10
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(18)

<400> SEQUENCE: 10

Cys Ser Tyr Ile Ile Val Gly Arg Gly Asp Ser Arg Leu Thr Tyr Gln
 1               5                  10                  15
Trp Cys

<210> SEQ ID NO 11
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(18)

<400> SEQUENCE: 11

Cys Ser Tyr Ile Val Val Gly Arg Gly Glu Gln Gln Ile Asn His His
 1               5                  10                  15
Trp Cys

<210> SEQ ID NO 12
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(18)

<400> SEQUENCE: 12

Cys Ser Tyr Ile Val Val Gly Arg Gly Asp Lys Gln Ile Asn His His
 1               5                  10                  15
Trp Cys

<210> SEQ ID NO 13
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(14)
```

```
<400> SEQUENCE: 13

Cys Asn Ile Ile Tyr Val Gly Glu Leu Ser His Gln Trp Cys
  1               5                  10

<210> SEQ ID NO 14
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(18)

<400> SEQUENCE: 14

Cys Ser Tyr Ile Val Val Gly Arg Gly Glu Gln Gln Ile Asn His His
  1               5                  10                  15

Trp Cys

<210> SEQ ID NO 15
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(14)

<400> SEQUENCE: 15

Cys Asn Ile Ile Tyr Val Gly Asp Leu Ser Gln Gln Trp Cys
  1               5                  10

<210> SEQ ID NO 16
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(14)

<400> SEQUENCE: 16

Cys Asn Ile Ile Tyr Val Gly Asp Leu Asn His Gln Trp Cys
  1               5                  10

<210> SEQ ID NO 17
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(18)

<400> SEQUENCE: 17

Cys Ser Tyr Ile Val Val Gly Arg Gly Asp Lys Gln Ile Asn His His
  1               5                  10                  15

Trp Cys

<210> SEQ ID NO 18
<211> LENGTH: 18
<212> TYPE: PRT
<213> ORGANISM: Artificial Sequence
<220> FEATURE:
```

<223> OTHER INFORMATION: Synthetic
<220> FEATURE:
<221> NAME/KEY: DISULFID
<222> LOCATION: (1)..(18)

<400> SEQUENCE: 18

Cys Ser Tyr Ile Val Val Gly Arg Gly Thr Thr Gln Ile Asn Tyr His
1 5 10 15

Trp Cys

<210> SEQ ID NO 19
<211> LENGTH: 27
<212> TYPE: DNA
<213> ORGANISM: Dengue virus

<400> SEQUENCE: 19
catatggcca tggacaaact acagctc 27

<210> SEQ ID NO 20
<211> LENGTH: 24
<212> TYPE: DNA
<213> ORGANISM: Dengue virus

<400> SEQUENCE: 20
ctcgaggccg atggaacttc cttt 24

<210> SEQ ID NO 21
<211> LENGTH: 5706
<212> TYPE: DNA
<213> ORGANISM: Dengue virus

<400> SEQUENCE: 21
taatacgact cactataggg gaattgtgag cggataacaa ttcccctcta gaaataattt 60
tgtttaactt taagaaggag atatacatat ggccatggac aaactacagc tcaaaggaat 120
gtcatactct atgtgtacag gaaagtttaa aattgtgaag gaaatagcag aaacacaaca 180
tggaacaata gttatcagag tacaatatga aggggacggc tctccatgta agatcccttt 240
tgagataatg gatttggaaa aaagacacgt cttaggtcgc ctgattacag ttaacccgat 300
cgtaacagaa aaagatagcc cagtcaacat agaagcagaa cctccattcg gagacagcta 360
catcatcata ggagtagagc cgggacaatt gaaactcaac tggtttaaga aaggaagttc 420
catcggcctc gagcaccacc accaccacca ctgagatccg gctgctaaca aagcccgaaa 480
ggaagctgag ttggctgctg ccaccgctga gcaataacta gcataacccc ttggggcctc 540
taaacgggtc ttgaggggtt ttttgctgaa aggaggaact atatccggat tggcgaatgg 600
gacgcgccct gtagcggcgc attaagcgcg gcgggtgtgg tggttacgcg cagcgtgacc 660
gctacacttg ccagcgccct agcgcccgct cctttcgctt tcttcccttc ctttctcgcc 720
acgttcgccg gctttccccg tcaagctcta aatcgggggc tccctttagg gttccgattt 780
agtgctttac ggcacctcga ccccaaaaaa cttgattagg gtgatggttc acgtagtggg 840
ccatcgccct gatagacggt ttttcgccct ttgacgttgg agtccacgtt ctttaatagt 900
ggactcttgt tccaaactgg aacaacactc aaccctatct cggtctattc ttttgattta 960
taagggattt tgccgatttc ggcctattgg ttaaaaaatg agctgattta acaaaaattt 1020
aacgcgaatt ttaacaaaat attaacgttt acaatttcag gtggcacttt tcggggaaat 1080
gtgcgcggaa cccctatttg tttatttttc taaatacatt caaatatgta tccgctcatg 1140
agacaataac cctgataaat gcttcaataa tattgaaaaa ggaagagtat gagtattcaa 1200

```
catttccgtg tcgcccttat tcccttttt gcggcatttt gccttcctgt ttttgctcac    1260
ccagaaacgc tggtgaaagt aaaagatgct gaagatcagt tgggtgcacg agtgggttac    1320
atcgaactgg atctcaacag cggtaagatc cttgagagtt ttcgccccga agaacgtttt    1380
ccaatgatga gcacttttaa agttctgcta tgtggcgcgg tattatcccg tattgacgcc    1440
gggcaagagc aactcggtcg ccgcatacac tattctcaga atgacttggt tgagtactca    1500
ccagtcacag aaaagcatct tacggatggc atgacagtaa gagaattatg cagtgctgcc    1560
ataaccatga gtgataacac tgcggccaac ttacttctga caacgatcgg aggaccgaag    1620
gagctaaccg cttttttgca caacatgggg gatcatgtaa ctcgccttga tcgttgggaa    1680
ccggagctga atgaagccat accaaacgac gagcgtgaca ccacgatgcc tgcagcaatg    1740
gcaacaacgt tgcgcaaact attaactggc gaactactta ctctagcttc ccggcaacaa    1800
ttaatagact ggatggaggc ggataaagtt gcaggaccac ttctgcgctc ggcccttccg    1860
gctggctggt ttattgctga taaatctgga gccggtgagc gtgggtctcg cggtatcatt    1920
gcagcactgg ggccagatgg taagccctcc cgtatcgtag ttatctacac gacggggagt    1980
caggcaacta tggatgaacg aaatagacag atcgctgaga taggtgcctc actgattaag    2040
cattggtaac tgtcagacca agtttactca tatatacttt agattgattt aaaacttcat    2100
ttttaattta aaaggatcta ggtgaagatc ctttttgata atctcatgac caaaatccct    2160
taacgtgagt tttcgttcca ctgagcgtca gaccccgtag aaaagatcaa aggatcttct    2220
tgagatcctt tttttctgcg cgtaatctgc tgcttgcaaa caaaaaaacc accgctacca    2280
gcggtggttt gtttgccgga tcaagagcta ccaactcttt ttccgaaggt aactggcttc    2340
agcagagcgc agataccaaa tactgtcctt ctagtgtagc cgtagttagg ccaccacttc    2400
aagaactctg tagcaccgcc tacatacctc gctctgctaa tcctgttacc agtggctgct    2460
gccagtggcg ataagtcgtg tcttaccggg ttggactcaa gacgatagtt accggataag    2520
gcgcagcggt cgggctgaac ggggggttcg tgcacacagc ccagcttgga gcgaacgacc    2580
tacaccgaac tgagatacct acagcgtgag ctatgagaaa gcgccacgct tcccgaaggg    2640
agaaaggcgg acaggtatcc ggtaagcggc agggtcggaa caggagagcg cacgagggag    2700
cttccagggg gaaacgcctg gtatctttat agtcctgtcg ggtttcgcca cctctgactt    2760
gagcgtcgat ttttgtgatg ctcgtcaggg gggcggagcc tatggaaaaa cgccagcaac    2820
gcggcctttt tacggttcct ggccttttgc tggccttttg ctcacatgtt ctttcctgcg    2880
ttatcccctg attctgtgga taaccgtatt accgcctttg agtgagctga taccgctcgc    2940
cgcagccgaa cgaccgagcg cagcgagtca gtgagcgagg aagcggaaga gcgcctgatg    3000
cggtattttc tccttacgca tctgtgcggt atttcacacc gcatatatgg tgcactctca    3060
gtacaatctg ctctgatgcc gcatagttaa gccagtatac actccgctat cgctacgtga    3120
ctgggtcatg gctgcgcccc gacacccgcc aacacccgct gacgcgccct gacgggcttg    3180
tctgctcccg gcatccgctt acagacaagc tgtgaccgtc tccgggagct gcatgtgtca    3240
gaggttttca ccgtcatcac cgaaacgcgc gaggcagctg cggtaaagct catcagcgtg    3300
gtcgtgaagc gattcacaga tgtctgcctg ttcatccgcg tccagctcgt tgagtttctc    3360
cagaagcgtt aatgtctggc ttctgataaa gcgggccatg ttaagggcgg ttttttcctg    3420
tttggtcact gatgcctccg tgtaaggggg attctgttc atggggtaa tgataccgat    3480
gaaacgagag aggatgctca cgatacgggt tactgatgat gaacatgccc ggttactgga    3540
acgttgtgag ggtaaacaac tggcggtatg gatgcggcgg gaccagagaa aaatcactca    3600
```

```
gggtcaatgc cagcgcttcg ttaatacaga tgtaggtgtt ccacagggta gccagcagca     3660
tcctgcgatg cagatccgga acataatggt gcagggcgct gacttccgcg tttccagact     3720
ttacgaaaca cggaaaccga agaccattca tgttgttgct caggtcgcag acgttttgca     3780
gcagcagtcg cttcacgttc gctcgcgtat cggtgattca ttctgctaac cagtaaggca     3840
accccgccag cctagccggg tcctcaacga caggagcacg atcatgcgca cccgtggggc     3900
cgccatgccg gcgataatgg cctgcttctc gccgaaacgt tggtggcgg gaccagtgac      3960 gaaggcttga gcgagggcgt gcaagattcc gaataccgca agcgacaggc cgatcatcgt     4020
cgcgctccag cgaaagcggt cctcgccgaa aatgacccag agcgctgccg gcacctgtcc     4080
tacgagttgc atgataaaga agacagtcat aagtgcggcg acgatagtca tgccccgcgc     4140
ccaccggaag gagctgactg ggttgaaggc tctcaagggc atcggtcgag atcccggtgc     4200
ctaatgagtg agctaactta cattaattgc gttgcgctca ctgcccgctt tccagtcggg     4260
aaacctgtcg tgccagctgc attaatgaat cggccaacgc gcggggagag gcggtttgcg     4320
tattgggcgc cagggtggtt tttcttttca ccagtgagac gggcaacagc tgattgccct     4380
tcaccgcctg gccctgagag agttgcagca agcggtccac gctggtttgc cccagcaggc     4440
gaaaatcctg tttgatggtg gttaacggcg ggatataaca tgagctgtct tcggtatcgt     4500
cgtatcccac taccgagata tccgcaccaa cgcgcagccc ggactcggta atggcgcgca     4560
ttgcgcccag cgccatctga tcgttggcaa ccagcatcgc agtgggaacg atgccctcat     4620
tcagcatttg catggtttgt tgaaaaccgg acatggcact ccagtcgcct tcccgttccg     4680
ctatcggctg aatttgattg cgagtgagat atttatgcca gccagccaga cgcagacgcg     4740
ccgagacaga acttaatggg cccgctaaca gcgcgatttg ctggtgaccc aatgcgacca     4800
gatgctccac gcccagtcgc gtaccgtctt catgggagaa aataatactg ttgatgggtg     4860
tctggtcaga gacatcaaga aataacgccg gaacattagt gcaggcagct tccacagcaa     4920
tggcatcctg gtcatccagc ggatagttaa tgatcagccc actgacgcgt tgcgcgagaa     4980
gattgtgcac cgccgcttta caggcttcga cgccgcttcg ttctaccatc gacaccacca     5040
cgctggcacc cagttgatcg gcgcgagatt taatcgccgc gacaatttgc gacggcgcgt     5100
gcagggccag actggaggtg gcaacgccaa tcagcaacga ctgtttgccc gccagttgtt     5160
gtgccacgcg gttgggaatg taattcagct ccgccatcgc cgcttccact ttttcccgcg     5220
ttttcgcaga aacgtggctg gcctggttca ccacgcggga aacggtctga taagagacac     5280
cggcatactc tgcgacatcg tataacgtta ctggtttcac attcaccacc ctgaattgac     5340
tctcttccgg cgctatcat gccataccgc gaaaggtttt gcgccattcg atggtgtccg     5400
ggatctcgac gctctccctt atgcgactcc tgcattagga agcagccag tagtaggttg      5460 aggccgttga gcaccgccgc cgcaaggaat ggtgcatgca aggagatggc gcccaacagt     5520
cccccggcca cggggcctgc caccatacc acgccgaaac aagcgctcat gagcccgaag      5580
tggcgagccc gatcttcccc atcggtgatg tcggcgatat aggcgccagc aaccgcacct     5640
gtggcgccgg tgatgccggc cacgatgcgt ccggcgtaga ggatcgagat ctcgatcccg     5700
cgaaat                                                                5706
```

<210> SEQ ID NO 22
<211> LENGTH: 121
<212> TYPE: PRT
<213> ORGANISM: Dengue virus
<220> FEATURE:
<221> NAME/KEY: DISULFID
<222> LOCATION: (16)..(47)

<400> SEQUENCE: 22

| | | | | | | | | | | | | | | |
|---|---|---|---|---|---|---|---|---|---|---|---|---|---|---|
| Met | Ala | Met | Asp | Lys | Leu | Gln | Leu | Lys | Gly | Met | Ser | Tyr | Ser | Met | Cys |
| 1 | | | | 5 | | | | | 10 | | | | | 15 | |
| Thr | Gly | Lys | Phe | Lys | Ile | Val | Lys | Glu | Ile | Ala | Glu | Thr | Gln | His | Gly |
| | | | 20 | | | | | 25 | | | | | 30 | | |
| Thr | Ile | Val | Ile | Arg | Val | Gln | Tyr | Glu | Gly | Asp | Gly | Ser | Pro | Cys | Lys |
| | | 35 | | | | | 40 | | | | | 45 | | | |
| Ile | Pro | Phe | Glu | Ile | Met | Asp | Leu | Glu | Lys | Arg | His | Val | Leu | Gly | Arg |
| | 50 | | | | | 55 | | | | | 60 | | | | |
| Leu | Ile | Thr | Val | Asn | Pro | Ile | Val | Thr | Glu | Lys | Asp | Ser | Pro | Val | Asn |
| 65 | | | | | 70 | | | | | 75 | | | | | 80 |
| Ile | Glu | Ala | Glu | Pro | Pro | Phe | Gly | Asp | Ser | Tyr | Ile | Ile | Ile | Gly | Val |
| | | | | 85 | | | | | 90 | | | | | 95 | |
| Glu | Pro | Gly | Gln | Leu | Lys | Leu | Asn | Trp | Phe | Lys | Lys | Gly | Ser | Ser | Ile |
| | | | 100 | | | | | 105 | | | | | 110 | | |
| Gly | Leu | Glu | His | His | His | His | His | His | | | | | | | |
| | | | 115 | | | | | 120 | | | | | | | |

<210> SEQ ID NO 23
<211> LENGTH: 27
<212> TYPE: DNA
<213> ORGANISM: Homo sapiens

<400> SEQUENCE: 23
catatgtact cgcgggagaa gaaccag                                        27

<210> SEQ ID NO 24
<211> LENGTH: 22
<212> TYPE: DNA
<213> ORGANISM: Homo sapiens

<400> SEQUENCE: 24
ctcgagtcag agttcgttgt gc                                             22

<210> SEQ ID NO 25
<211> LENGTH: 6267
<212> TYPE: DNA
<213> ORGANISM: Homo sapiens

<400> SEQUENCE: 25

```
ttaatacgac tcactatagg ggaattgtga gcggataaca attcccctct agaaataatt     60
ttgtttaact ttaagaagga gatataccat gggcagcagc catcatcatc atcatcacag    120
cagcggcctg gtgccgcgcg gcagccatat gtactcgcgg gagaagaacc agcccaagcc    180
gtccccgaaa cgcgagtccg gagaggagtt ccgcatggag aagttgaacc agctgtggga    240
gaaggcccag cgactgcatc ttcctcccgt gaggctggcc gagctccacg ctgatctgaa    300
gatacaggag agggacgaac tcgcctggaa gaaactaaag cttgacggct tggacgaaga    360
tgggagaag gaagcgagac tcatacgcaa cctcaatgtc atcttggcca agtatggtct    420
ggacggaaag aaggacgctc ggcaggtgac cagcaactcc ctcagtggca cccaggaaga    480
cgggctggat gacccaggc tggaaaagct gtggcacaag gcgaagacct ctgggaaatt    540
ctccggcgaa gaactggaca gctctggcg ggagttcctg catcacaaag agaagttca    600
cgagtacaac gtcctgctgg agaccctgag caggaccgaa gaaatccacg agaacgtcat    660
tagcccctcg gacctgagcg acatcaaggg cagcgtcctg cacagcaggc acacggagct    720
gaaggagaag ctgcgcagca tcaaccaggg cctggaccgc ctgcgcaggg tcagccacca    780
```

```
gggctacagc actgaggctg agttcgagga gcccagggtg attgacctgt gggacctggc    840
gcagtccgcc aacctcacgg acaaggagct ggaggcgttc cgggaggagc tcaagcactt    900
cgaagccaaa atcgagaagc acaaccacta ccagaagcag ctggagattg cgcacgagaa    960
gctgaggcac gcagagagcg tgggcgacgg cgagcgtgtg agccgcagcc gcgagaagca   1020
cgccctgctg gaggggcgga ccaaggagct gggctacacg gtgaagaagc atctgcagga   1080
cctgtccggc aggatctcca gagctcggca caacgaactc tgactcgagc accaccacca   1140
ccaccactga gatccggctg ctaacaaagc ccgaaaggaa gctgagttgg ctgctgccac   1200
cgctgagcaa taactagcat aaccccttgg ggcctctaaa cgggtcttga ggggttttt   1260
gctgaaagga ggaactatat ccggattggc gaatgggacg cgccctgtag cggcgcatta   1320
agcgcggcgg gtgtggtggt tacgcgcagc gtgaccgcta cacttgccag cgccctagcg   1380
cccgctcctt tcgctttctt cccttccttt ctcgccacgt tcgccggctt tccccgtcaa   1440
gctctaaatc gggggctccc tttagggttc cgatttagtg ctttacggca cctcgacccc   1500
aaaaaacttg attagggtga tggttcacgt agtgggccat cgccctgata cggttttt   1560
cgcccttgga cgttggagtc cacgttcttt aatagtggac tcttgttcca aactggaaca   1620
acactcaacc ctatctcggt ctattctttt gatttataag gattttgcc gatttcggcc   1680
tattggttaa aaaatgagct gatttaacaa aaatttaacg cgaattttaa caaaatatta   1740
acgtttacaa tttcaggtgg cacttttcgg ggaaatgtgc gcggaacccc tatttgttta   1800
tttttctaaa tacattcaaa tatgtatccg ctcatgaatt aattcttaga aaaactcatc   1860
gagcatcaaa tgaaactgca atttattcat atcaggatta tcaataccat attttgaaa    1920
aagccgtttc tgtaatgaag gagaaaactc accgaggcag ttccatagga tgcaagatc    1980
ctggtatcgg tctgcgattc cgactcgtcc aacatcaata caacctatta atttcccctc   2040
gtcaaaaata aggttatcaa gtgagaaatc accatgagtg acgactgaat ccggtgagaa   2100
tggcaaaagt ttatgcattt cttttccaga cttgttcaaca ggccagccat tacgctcgtc   2160
atcaaaatca ctcgcatcaa ccaaaccgtt attcattcgt gattgcgcct gagcgagacg   2220
aaatacgcga tcgctgttaa aaggacaatt acaaacagga atcgaatgca accggcgcag   2280
gaacactgcc agcgcatcaa caatattttc acctgaatca ggatattctt ctaatacctg   2340
gaatgctgtt ttcccgggga tcgcagtggt gagtaaccat gcatcatcag gagtacggat   2400
aaaatgcttg atggtcggaa gaggcataaa ttccgtcagc cagtttagtc tgaccatctc   2460
atctgtaaca tcattggcaa cgctacctt gccatgtttc agaaacaact ctggcgcatc   2520
gggcttccca tacaatcgat agattgtcgc acctgattgc ccgacattat cgcgagccca   2580
tttataccca tataaatcag catccatgtt ggaatttaat cgcggcctag agcaagacgt   2640
ttcccgttga atatggctca taacaccct tgtattactg tttatgtaag cagacagttt   2700
tattgttcat gaccaaaatc ccttaacgtg agttttcgtt ccactgagcg tcagaccccg   2760
tagaaaagat caaaggatct tcttgagatc cttttttct gcgcgtaatc tgctgcttgc   2820
aaacaaaaaa accaccgcta ccagcggtgg tttgtttgcc ggatcaagag ctaccaactc   2880
ttttccgaa ggtaactggc ttcagcagag cgcagatacc aaatactgtc cttctagtgt   2940
agccgtagtt aggccaccac ttcaagaact ctgtagcacc gcctacatac ctcgctctgc   3000
taatcctgtt accagtggct gctgccagtg gcgataagtc gtgtcttacc gggttggact   3060
caagacgata gttaccggat aaggcgcagc ggtcgggctg aacggggggt tcgtgcacac   3120
agcccagctt ggagcgaacg acctacaccg aactgagata cctacagcgt gagctatgag   3180
```

```
aaagcgccac gcttcccgaa gggagaaagg cggacaggta tccggtaagc ggcagggtcg   3240
gaacaggaga gcgcacgagg gagcttccag ggggaaacgc ctggtatctt tatagtcctg   3300
tcgggtttcg ccacctctga cttgagcgtc gattttgtg atgctcgtca ggggggcgga    3360
gcctatggaa aaacgccagc aacgcggcct ttttacggtt cctggccttt tgctggcctt   3420
ttgctcacat gttctttcct gcgttatccc ctgattctgt ggataaccgt attaccgcct   3480
ttgagtgagc tgataccgct cgccgcagcc gaacgaccga gcgcagcgag tcagtgagcg   3540
aggaagcgga gagcgcctg atgcggtatt ttctccttac gcatctgtgc ggtatttcac    3600
accgcatata tggtgcactc tcagtacaat ctgctctgat gccgcatagt taagccagta   3660
tacactccgc tatcgctacg tgactgggtc atggctgcgc cccgacaccc gccaacaccc   3720
gctgacgcgc cctgacgggc ttgtctgctc ccggcatccg cttacagaca agctgtgacc   3780
gtctccggga gctgcatgtg tcagaggttt tcaccgtcat caccgaaacg cgcgaggcag   3840
ctgcggtaaa gctcatcagc gtggtcgtga agcgattcac agatgtctgc ctgttcatcc   3900
gcgtccagct cgttgagttt ctccagaagc gttaatgtct ggcttctgat aaagcgggcc   3960
atgttaaggg cggttttttc ctgtttggtc actgatgcct ccgtgtaagg gggatttctg   4020
ttcatggggg taatgatacc gatgaaacga gagaggatgc tcacgatacg ggttactgat   4080
gatgaacatg cccggttact ggaacgttgt gagggtaaac aactggcggt atggatgcgg   4140
cgggaccaga gaaaaatcac tcagggtcaa tgccagcgct tcgttaatac agatgtaggt   4200
gttccacagg gtagccagca gcatcctgcg atgcagatcc ggaacataat ggtgcagggc   4260
gctgacttcc gcgtttccag actttacgaa acacggaaac gaagaccat tcatgttgtt    4320 gctcaggtcg cagacgtttt gcagcagcag tcgcttcacg ttcgctcgcg tatcggtgat   4380
tcattctgct aaccagtaag gcaaccccgc cagcctagcc gggtcctcaa cgacaggagc   4440
acgatcatgc gcacccgtgg ggccgccatg ccggcgataa tggcctgctt ctcgccgaaa   4500
cgtttggtgg cgggaccagt gacgaaggct tgagcgaggg cgtgcaagat tccgaatacc   4560
gcaagcgaca ggccgatcat cgtcgcgctc cagcgaaagc ggtcctcgcc gaaaatgacc   4620
cagagcgctg ccggcacctg tcctacgagt tgcatgataa agaagacagt cataagtgcg   4680
gcgacgatag tcatgcccg cgcccaccgg aaggagctga ctgggttgaa ggctctcaag    4740
ggcatcggtc gagatcccgg tgcctaatga gtgagctaac ttacattaat tgcgttgcgc   4800
tcactgcccg ctttccagtc gggaaacctg tcgtgccagc tgcattaatg aatcggccaa   4860
cgcgcgggga gaggcggttt gcgtattggg cgccagggtg ttttctttt caccagtga    4920 gacgggcaac agctgattgc ccttcaccgc ctggccctga gagagttgca gcaagcggtc   4980
cacgctggtt tgccccagca ggcgaaaatc ctgtttgatg gtggttaacg gcgggatata   5040
acatgagctg tcttcggtat cgtcgtatcc cactaccgag atatccgcac caacgcgcag   5100
cccggactcg gtaatggcgc gcattgcgcc cagcgccatc tgatcgttgg caaccagcat   5160
cgcagtggga acgatgccct cattcagcat ttgcatggtt tgttgaaaac cggacatggc   5220
actccagtcg ccttcccgtt ccgctatcgg ctgaatttga ttgcgagtga tatttatg    5280 ccagccagcc agacgcagac gcgccgagac agaacttaat gggcccgcta acagcgcgat   5340
ttgctggtga cccaatgcga ccagatgctc cacgcccagt cgcgtaccgt cttcatggga   5400
gaaaataata ctgttgatgg gtgtctggtc agagacatca agaaataacg ccggaacatt   5460
agtgcaggca gcttccacag caatggcatc ctggtcatcc agcggatagt taatgatcag   5520
cccactgacg cgttgcgcga agattgtg caccgccgct ttacaggctt cgacgccgct     5580
```

-continued

```
tcgttctacc atcgacacca ccacgctggc acccagttga tcggcgcgag atttaatcgc    5640
cgcgacaatt gcgacggcgc gtgcagggcc agactggagg tggcaacgcc aatcagcaac    5700
gactgtttgc ccgccagttg ttgtgccacg cggttgggaa tgtaattcag ctccgccatc    5760
gccgcttcca cttttccccg cgttttcgca gaaacgtggc tggcctggtt caccacgcgg    5820
gaaacggtct gataagagac accggcatac tctgcgacat cgtataacgt tactggtttc    5880
acattcacca ccctgaattg actctcttcc gggcgctatc atgccatacc gcgaaaggtt    5940
ttgcgccatt cgatggtgtc cgggatctcg acgctctccc ttatgcgact cctgcattag    6000
gaagcagccc agtagtaggt tgaggccgtt gagcaccgcc gccgcaagga atggtgcatg    6060
caaggagatg gcgcccaaca gtcccccggc cacggggcct gccaccatac ccacgccgaa    6120
acaagcgctc atgagcccga gtggcgagcc cgatcttccc catcggtga tgtcggcgat     6180 ataggcgcca gcaaccgcac ctgtggcgcc ggtgatgccg ccacgatgc gtccggcgta     6240 gaggatcgag atctcgatcc cgcgaaa                                        6267
```

<210> SEQ ID NO 26
<211> LENGTH: 344
<212> TYPE: PRT
<213> ORGANISM: Homo sapiens

<400> SEQUENCE: 26

```
Met Gly Ser Ser His His His His His His Ser Ser Gly Leu Val Pro
 1               5                   10                  15

Arg Gly Ser His Met Tyr Ser Arg Glu Lys Asn Gln Pro Lys Pro Ser
            20                  25                  30

Pro Lys Arg Glu Ser Gly Glu Glu Phe Arg Met Glu Lys Leu Asn Gln
        35                  40                  45

Leu Trp Glu Lys Ala Gln Arg Leu His Leu Pro Pro Val Arg Leu Ala
    50                  55                  60

Glu Leu His Ala Asp Leu Lys Ile Gln Glu Arg Asp Glu Leu Ala Trp
65                  70                  75                  80

Lys Lys Leu Lys Leu Asp Gly Leu Asp Glu Asp Gly Glu Lys Glu Ala
                85                  90                  95

Arg Leu Ile Arg Asn Leu Asn Val Ile Leu Ala Lys Tyr Gly Leu Asp
            100                 105                 110

Gly Lys Lys Asp Ala Arg Gln Val Thr Ser Asn Ser Leu Ser Gly Thr
        115                 120                 125

Gln Glu Asp Gly Leu Asp Asp Pro Arg Leu Glu Lys Leu Trp His Lys
    130                 135                 140

Ala Lys Thr Ser Gly Lys Phe Ser Gly Glu Glu Leu Asp Lys Leu Trp
145                 150                 155                 160

Arg Glu Phe Leu His His Lys Glu Lys Val His Glu Tyr Asn Val Leu
                165                 170                 175

Leu Glu Thr Leu Ser Arg Thr Glu Glu Ile His Glu Asn Val Ile Ser
            180                 185                 190

Pro Ser Asp Leu Ser Asp Ile Lys Gly Ser Val Leu His Ser Arg His
        195                 200                 205

Thr Glu Leu Lys Glu Lys Leu Arg Ser Ile Asn Gln Gly Leu Asp Arg
    210                 215                 220

Leu Arg Arg Val Ser His Gln Gly Tyr Ser Thr Glu Ala Glu Phe Glu
225                 230                 235                 240

Glu Pro Arg Val Ile Asp Leu Trp Asp Leu Ala Gln Ser Ala Asn Leu
                245                 250                 255
```

```
Thr Asp Lys Glu Leu Glu Ala Phe Arg Glu Leu Lys His Phe Glu
        260                 265                 270

Ala Lys Ile Glu Lys His Asn His Tyr Gln Lys Gln Leu Glu Ile Ala
        275                 280                 285

His Glu Lys Leu Arg His Ala Glu Ser Val Gly Asp Gly Glu Arg Val
290                 295                 300

Ser Arg Ser Arg Glu Lys His Ala Leu Leu Glu Gly Arg Thr Lys Glu
305                 310                 315                 320

Leu Gly Tyr Thr Val Lys Lys His Leu Gln Asp Leu Ser Gly Arg Ile
                325                 330                 335

Ser Arg Ala Arg His Asn Glu Leu
        340

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

Lys Ala Gln Leu Lys Leu Asn Trp Phe Lys Lys Gly Ser Ser
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (2)..(9)

<400> SEQUENCE: 28

Gly Cys Gly Val Glu Pro Gly Gln Cys
1               5

<210> SEQ ID NO 29
<211> LENGTH: 495
<212> TYPE: PRT
<213> ORGANISM: Dengue virus type 1

<400> SEQUENCE: 29

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
                20                  25                  30

Thr Met Ala Lys Asn Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Leu Thr Cys Ala Lys Phe Lys Cys Val Thr Lys Leu Glu Gly Lys
        115                 120                 125
```

Ile Val Gln Tyr Glu Asn Leu Lys Tyr Ser Val Ile Val Thr Val His
130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
                180                 185                 190

Phe Asn Glu Met Val Leu Leu Thr Met Lys Glu Lys Ser Trp Leu Val
            195                 200                 205

His Lys Gln Trp Phe Leu Asp Leu Pro Leu Pro Trp Thr Ser Gly Ala
            210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
            275                 280                 285

Met Asp Lys Leu Thr Leu Lys Gly Thr Ser Tyr Val Met Cys Thr Gly
290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
                340                 345                 350

Thr Ala Asn Pro Ile Val Thr Asp Lys Glu Lys Pro Val Asn Ile Glu
            355                 360                 365

Thr Glu Pro Pro Phe Gly Glu Ser Tyr Ile Val Val Gly Ala Gly Glu
            370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
                420                 425                 430

Gly Lys Leu Val His Gln Val Phe Gly Thr Ala Tyr Gly Val Leu Phe
            435                 440                 445

Ser Gly Val Ser Trp Thr Met Lys Ile Gly Ile Gly Ile Leu Leu Thr
450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495

<210> SEQ ID NO 30
<211> LENGTH: 20
<212> TYPE: PRT
<213> ORGANISM: Artificial Sequence
<220> FEATURE:
<223> OTHER INFORMATION: Synthetic

<400> SEQUENCE: 30

Lys Ala Cys Ser Tyr Ile Ile Ile Gly Val Glu Pro Gly Gln Leu Lys

```
                1               5                   10                  15
Leu Asn Trp Cys
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic

<400> SEQUENCE: 31

Lys Ala Cys Ser Tyr Ile Ile Ile Gly Val Glu Pro Gly Gln Ile Lys
1               5                   10                  15

Ile Ser Trp Cys
            20

<210> SEQ ID NO 32
<211> LENGTH: 42
<212> TYPE: PRT
<213> ORGANISM: Homo sapiens

<400> SEQUENCE: 32

Lys Thr Cys Ser Pro Lys Gln Phe Ala Cys Arg Asp Gln Ile Thr Cys
1               5                   10                  15

Ile Ser Lys Gly Trp Arg Cys Asp Gly Glu Arg Asp Cys Pro Asp Gly
            20                  25                  30

Ser Asp Glu Ala Pro Glu Ile Cys Pro Gln
        35                  40

<210> SEQ ID NO 33
<211> LENGTH: 41
<212> TYPE: PRT
<213> ORGANISM: Homo sapiens

<400> SEQUENCE: 33

Gln Arg Cys Gln Pro Asn Glu His Asn Cys Leu Gly Thr Glu Leu Cys
1               5                   10                  15

Val Pro Met Ser Arg Leu Cys Asn Gly Val Gln Asp Cys Met Asp Gly
            20                  25                  30

Ser Asp Glu Gly Pro His Cys Arg Glu
        35                  40

<210> SEQ ID NO 34
<211> LENGTH: 41
<212> TYPE: PRT
<213> ORGANISM: Homo sapiens

<400> SEQUENCE: 34

Pro Gln Cys Gln Pro Gly Glu Phe Ala Cys Ala Asn Ser Arg Cys Ile
1               5                   10                  15

Gln Glu Arg Trp Lys Cys Asp Gly Asp Asn Asp Cys Leu Asp Asn Ser
            20                  25                  30

Asp Glu Ala Pro Ala Leu Cys His Gln
        35                  40

<210> SEQ ID NO 35
<211> LENGTH: 41
<212> TYPE: PRT
<213> ORGANISM: Homo sapiens

<400> SEQUENCE: 35
```

His Thr Cys Pro Ser Asp Arg Phe Lys Cys Glu Asn Asn Arg Cys Ile
1               5                   10                  15

Pro Asn Arg Trp Leu Cys Asp Gly Asp Asn Asp Cys Gly Asn Ser Glu
            20                  25                  30

Asp Glu Ser Asn Ala Thr Cys Ser Ala
        35                  40

<210> SEQ ID NO 36
<211> LENGTH: 40
<212> TYPE: PRT
<213> ORGANISM: Homo sapiens

<400> SEQUENCE: 36

Arg Thr Cys Pro Pro Asn Gln Phe Ser Cys Ala Ser Gly Arg Cys Ile
1               5                   10                  15

Pro Ile Ser Trp Thr Cys Asp Leu Asp Asp Asp Cys Gly Asp Arg Ser
            20                  25                  30

Asp Glu Ser Ala Ser Cys Ala Tyr
        35                  40

<210> SEQ ID NO 37
<211> LENGTH: 40
<212> TYPE: PRT
<213> ORGANISM: Homo sapiens

<400> SEQUENCE: 37

Pro Thr Cys Phe Pro Leu Thr Gln Phe Thr Cys Asn Asn Gly Arg Cys
1               5                   10                  15

Ile Asn Ile Asn Trp Arg Cys Asp Asn Asp Asn Asp Cys Gly Asp Asn
            20                  25                  30

Ser Asp Glu Ala Gly Cys Ser His
        35                  40

<210> SEQ ID NO 38
<211> LENGTH: 41
<212> TYPE: PRT
<213> ORGANISM: Homo sapiens

<400> SEQUENCE: 38

His Ser Cys Ser Ser Thr Gln Phe Lys Cys Asn Ser Gly Arg Cys Ile
1               5                   10                  15

Pro Glu His Trp Thr Cys Asp Gly Asp Asn Asp Cys Gly Asp Tyr Ser
            20                  25                  30

Asp Glu Thr His Ala Asn Cys Thr Asn
        35                  40

<210> SEQ ID NO 39
<211> LENGTH: 40
<212> TYPE: PRT
<213> ORGANISM: Homo sapiens

<400> SEQUENCE: 39

Gly Gly Cys His Thr Asp Glu Phe Gln Cys Arg Leu Asp Gly Leu Cys
1               5                   10                  15

Ile Pro Leu Arg Trp Arg Cys Asp Gly Asp Thr Asp Cys Met Asp Ser
            20                  25                  30

Ser Asp Glu Lys Ser Cys Glu Gly
        35                  40

<210> SEQ ID NO 40
<211> LENGTH: 41

```
<212> TYPE: PRT
<213> ORGANISM: Homo sapiens

<400> SEQUENCE: 40

His Val Cys Asp Pro Ser Val Lys Phe Gly Cys Lys Asp Ser Ala Arg
  1               5                  10                  15

Cys Ile Ser Lys Ala Trp Val Cys Asp Gly Asp Asn Asp Cys Glu Asp
                 20                  25                  30

Asn Ser Asp Glu Glu Asn Cys Glu Ser
             35                  40

<210> SEQ ID NO 41
<211> LENGTH: 40
<212> TYPE: PRT
<213> ORGANISM: Homo sapiens

<400> SEQUENCE: 41

Leu Ala Cys Arg Pro Pro Ser His Pro Cys Ala Asn Asn Thr Ser Val
  1               5                  10                  15

Cys Leu Pro Pro Asp Lys Leu Cys Asp Gly Asn Asp Asp Cys Gly Asp
                 20                  25                  30

Gly Ser Asp Glu Gly Glu Leu Cys
             35                  40

<210> SEQ ID NO 42
<211> LENGTH: 42
<212> TYPE: PRT
<213> ORGANISM: Homo sapiens

<400> SEQUENCE: 42

Ser Ser Cys Arg Ala Gln Asp Glu Phe Glu Cys Ala Asn Gly Glu Cys
  1               5                  10                  15

Ile Asn Phe Ser Leu Thr Cys Asp Gly Val Pro His Cys Lys Asp Lys
                 20                  25                  30

Ser Asp Glu Lys Pro Ser Tyr Cys Asn Ser
             35                  40

<210> SEQ ID NO 43
<211> LENGTH: 39
<212> TYPE: PRT
<213> ORGANISM: Homo sapiens

<400> SEQUENCE: 43

Arg Arg Cys Lys Lys Thr Phe Arg Gln Cys Ser Asn Gly Arg Cys Val
  1               5                  10                  15

Ser Asn Met Leu Trp Cys Asn Gly Ala Asp Asp Cys Gly Asp Gly Ser
                 20                  25                  30

Asp Glu Ile Pro Cys Asn Lys
             35

<210> SEQ ID NO 44
<211> LENGTH: 39
<212> TYPE: PRT
<213> ORGANISM: Homo sapiens

<400> SEQUENCE: 44

Thr Ala Cys Gly Val Gly Glu Phe Arg Cys Arg Asp Gly Thr Cys Ile
  1               5                  10                  15

Gly Asn Ser Ser Arg Cys Asn Gln Phe Val Asp Cys Glu Asp Ala Ser
                 20                  25                  30

Asp Glu Met Asn Cys Ser Ala
```

-continued

<210> SEQ ID NO 45
<211> LENGTH: 49
<212> TYPE: PRT
<213> ORGANISM: Homo sapiens

<400> SEQUENCE: 45

Thr Asp Cys Ser Ser Tyr Phe Arg Leu Gly Val Lys Gly Val Leu Phe
1               5                   10                  15

Gln Pro Cys Glu Arg Thr Ser Leu Cys Tyr Ala Pro Ser Trp Val Cys
            20                  25                  30

Asp Gly Ala Asn Asp Cys Gly Asp Tyr Ser Asp Glu Arg Asp Cys Pro
        35                  40                  45

Gly

<210> SEQ ID NO 46
<211> LENGTH: 38
<212> TYPE: PRT
<213> ORGANISM: Homo sapiens

<400> SEQUENCE: 46

Pro Arg Cys Pro Leu Asn Tyr Phe Ala Cys Pro Ser Gly Arg Cys Ile
1               5                   10                  15

Pro Met Ser Trp Thr Cys Asp Lys Glu Asp Asp Cys Glu His Gly Glu
            20                  25                  30

Asp Glu Thr His Cys Asn
        35

<210> SEQ ID NO 47
<211> LENGTH: 40
<212> TYPE: PRT
<213> ORGANISM: Homo sapiens

<400> SEQUENCE: 47

Lys Phe Cys Ser Glu Ala Gln Phe Glu Cys Gln Asn His Arg Cys Ile
1               5                   10                  15

Ser Lys Gln Trp Leu Cys Asp Gly Ser Asp Asp Cys Gly Asp Gly Ser
            20                  25                  30

Asp Glu Ala Ala His Cys Glu Gly
        35                  40

<210> SEQ ID NO 48
<211> LENGTH: 43
<212> TYPE: PRT
<213> ORGANISM: Homo sapiens

<400> SEQUENCE: 48

Lys Thr Cys Gly Pro Ser Ser Phe Ser Cys Pro Gly Thr His Val Cys
1               5                   10                  15

Val Pro Glu Arg Trp Leu Cys Asp Gly Asp Lys Asp Cys Ala Asp Gly
            20                  25                  30

Ala Asp Glu Ser Ile Ala Ala Gly Cys Leu Tyr
        35                  40

<210> SEQ ID NO 49
<211> LENGTH: 40
<212> TYPE: PRT
<213> ORGANISM: Homo sapiens

<400> SEQUENCE: 49

```
Ser Thr Cys Asp Asp Arg Glu Phe Met Cys Gln Asn Arg Gln Cys Ile
1               5                   10                  15

Pro Lys His Phe Val Cys Asp His Asp Arg Asp Cys Ala Asp Gly Ser
            20                  25                  30

Asp Glu Ser Pro Glu Cys Glu Tyr
        35                  40

<210> SEQ ID NO 50
<211> LENGTH: 44
<212> TYPE: PRT
<213> ORGANISM: Homo sapiens

<400> SEQUENCE: 50

Pro Thr Cys Gly Pro Ser Glu Phe Arg Cys Ala Asn Gly Arg Cys Leu
1               5                   10                  15

Ser Ser Arg Gln Trp Glu Cys Asp Gly Glu Asn Asp Cys His Asp Gln
            20                  25                  30

Ser Asp Glu Ala Pro Lys Asn Pro His Cys Thr Ser
        35                  40

<210> SEQ ID NO 51
<211> LENGTH: 39
<212> TYPE: PRT
<213> ORGANISM: Homo sapiens

<400> SEQUENCE: 51

His Lys Cys Asn Ala Ser Ser Gln Phe Leu Cys Ser Ser Gly Arg Cys
1               5                   10                  15

Val Ala Glu Ala Leu Leu Cys Asn Gly Gln Asp Asp Cys Gly Asp Ser
            20                  25                  30

Ser Asp Glu Arg Gly Cys His
        35

<210> SEQ ID NO 52
<211> LENGTH: 40
<212> TYPE: PRT
<213> ORGANISM: Homo sapiens

<400> SEQUENCE: 52

Ser Asn Cys Thr Ala Ser Gln Phe Val Cys Lys Asn Asp Lys Cys Ile
1               5                   10                  15

Pro Phe Trp Trp Lys Cys Asp Thr Glu Asp Asp Cys Gly Asp His Ser
            20                  25                  30

Asp Glu Pro Pro Asp Cys Pro Glu
        35                  40

<210> SEQ ID NO 53
<211> LENGTH: 39
<212> TYPE: PRT
<213> ORGANISM: Homo sapiens

<400> SEQUENCE: 53

Phe Lys Cys Arg Pro Gly Gln Phe Gln Cys Ser Thr Gly Ile Cys Thr
1               5                   10                  15

Asn Pro Ala Phe Ile Cys Asp Gly Asp Asn Asp Cys Gln Asp Asn Ser
            20                  25                  30

Asp Glu Ala Asn Cys Asp Ile
        35

<210> SEQ ID NO 54
<211> LENGTH: 40
```

```
<212> TYPE: PRT
<213> ORGANISM: Homo sapiens

<400> SEQUENCE: 54

His Val Cys Leu Pro Ser Gln Phe Lys Cys Thr Asn Thr Asn Arg Cys
  1               5                  10                  15

Ile Pro Gly Ile Phe Arg Cys Asn Gly Gln Asp Asn Cys Gly Asp Gly
             20                  25                  30

Glu Asp Glu Arg Asp Cys Pro Glu
         35                  40

<210> SEQ ID NO 55
<211> LENGTH: 41
<212> TYPE: PRT
<213> ORGANISM: Homo sapiens

<400> SEQUENCE: 55

Val Thr Cys Ala Pro Asn Gln Phe Gln Cys Ser Ile Thr Lys Arg Cys
  1               5                  10                  15

Ile Pro Arg Val Trp Val Cys Asp Arg Asp Asn Asp Cys Val Asp Gly
             20                  25                  30

Ser Asp Glu Pro Ala Asn Cys Thr Gln
         35                  40

<210> SEQ ID NO 56
<211> LENGTH: 42
<212> TYPE: PRT
<213> ORGANISM: Homo sapiens

<400> SEQUENCE: 56

Met Thr Cys Gly Val Asp Glu Phe Arg Cys Lys Asp Ser Gly Arg Cys
  1               5                  10                  15

Ile Pro Ala Arg Trp Lys Cys Asp Gly Glu Asp Asp Cys Gly Asp Gly
             20                  25                  30

Ser Asp Glu Pro Lys Glu Glu Cys Asp Glu
         35                  40

<210> SEQ ID NO 57
<211> LENGTH: 39
<212> TYPE: PRT
<213> ORGANISM: Homo sapiens

<400> SEQUENCE: 57

Arg Thr Cys Glu Pro Tyr Gln Phe Arg Cys Lys Asn Asn Arg Cys Val
  1               5                  10                  15

Pro Gly Arg Trp Gln Cys Asp Tyr Asp Asn Asp Cys Gly Asp Asn Ser
             20                  25                  30

Asp Glu Glu Ser Cys Thr Pro
         35

<210> SEQ ID NO 58
<211> LENGTH: 38
<212> TYPE: PRT
<213> ORGANISM: Homo sapiens

<400> SEQUENCE: 58

Arg Pro Cys Ser Glu Ser Glu Phe Ser Cys Ala Asn Gly Arg Cys Ile
  1               5                  10                  15

Ala Gly Arg Trp Lys Cys Asp Gly Asp His Asp Cys Ala Asp Gly Ser
             20                  25                  30

Asp Glu Lys Asp Cys Thr
```

<210> SEQ ID NO 59
<211> LENGTH: 39
<212> TYPE: PRT
<213> ORGANISM: Homo sapiens

<400> SEQUENCE: 59

Pro Arg Cys Asp Met Asp Gln Phe Gln Cys Lys Ser Gly His Cys Ile
1               5                   10                  15

Pro Leu Arg Trp Arg Cys Asp Ala Asp Ala Asp Cys Met Asp Gly Ser
            20                  25                  30

Asp Glu Glu Ala Cys Gly Thr
        35

<210> SEQ ID NO 60
<211> LENGTH: 41
<212> TYPE: PRT
<213> ORGANISM: Homo sapiens

<400> SEQUENCE: 60

Arg Thr Cys Pro Leu Asp Glu Phe Gln Cys Asn Asn Thr Leu Cys Lys
1               5                   10                  15

Pro Leu Ala Trp Lys Cys Asp Gly Asp Asp Cys Gly Asp Asn Ser
            20                  25                  30

Asp Glu Asn Pro Glu Glu Cys Ala Arg
        35                  40

<210> SEQ ID NO 61
<211> LENGTH: 41
<212> TYPE: PRT
<213> ORGANISM: Homo sapiens

<400> SEQUENCE: 61

Phe Val Cys Pro Pro Asn Arg Pro Phe Arg Cys Lys Asn Asp Arg Val
1               5                   10                  15

Cys Leu Trp Ile Gly Arg Gln Cys Asp Gly Thr Asp Asn Cys Gly Asp
            20                  25                  30

Gly Thr Asp Glu Glu Asp Cys Glu Pro
        35                  40

<210> SEQ ID NO 62
<211> LENGTH: 40
<212> TYPE: PRT
<213> ORGANISM: Homo sapiens

<400> SEQUENCE: 62

Thr His Cys Lys Asp Lys Lys Glu Phe Leu Cys Arg Asn Gln Arg Cys
1               5                   10                  15

Leu Ser Ser Ser Leu Arg Cys Asn Met Phe Asp Asp Cys Gly Asp Gly
            20                  25                  30

Ser Asp Glu Glu Asp Cys Ser Ile
        35                  40

<210> SEQ ID NO 63
<211> LENGTH: 10
<212> TYPE: PRT
<213> ORGANISM: Artificial Sequence
<220> FEATURE:
<223> OTHER INFORMATION: Synthetic

<400> SEQUENCE: 63

```
Val Gly Ala Gly Glu Lys Ala Leu Lys Leu
 1               5                  10
```

<210> SEQ ID NO 64
<211> LENGTH: 16
<212> TYPE: PRT
<213> ORGANISM: Artificial Sequence
<220> FEATURE:
<223> OTHER INFORMATION: Synthetic

<400> SEQUENCE: 64

```
Ser Tyr Ile Val Val Gly Ala Gly Glu Lys Ala Leu Lys Leu Ser Trp
 1               5                  10                  15
```

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

```
Ile Gly Val Glu Pro Gly Gln Leu Lys Leu
 1               5                  10
```

<210> SEQ ID NO 66
<211> LENGTH: 7
<212> TYPE: PRT
<213> ORGANISM: Artificial Sequence
<220> FEATURE:
<223> OTHER INFORMATION: Synthetic

<400> SEQUENCE: 66

```
Glu Lys Asp Ser Pro Val Asn
 1               5
```

<210> SEQ ID NO 67
<211> LENGTH: 30
<212> TYPE: PRT
<213> ORGANISM: Artificial Sequence
<220> FEATURE:
<223> OTHER INFORMATION: Synthetic

<400> SEQUENCE: 67

```
Glu Lys Asp Ser Pro Val Asn Val Glu Ala Glu Pro Pro Leu Gly Asp
 1               5                  10                  15

Ser Tyr Ile Ile Ile Gly Val Glu Pro Gly Gln Leu Lys Leu
            20                  25                  30
```

<210> SEQ ID NO 68
<211> LENGTH: 16
<212> TYPE: PRT
<213> ORGANISM: Artificial Sequence
<220> FEATURE:
<223> OTHER INFORMATION: Synthetic

<400> SEQUENCE: 68

```
Ser Tyr Ile Ile Ile Gly Val Glu Pro Gly Gln Leu Lys Leu Asn Trp
 1               5                  10                  15
```

<210> SEQ ID NO 69
<211> LENGTH: 16
<212> TYPE: PRT
<213> ORGANISM: Artificial Sequence
<220> FEATURE:
<223> OTHER INFORMATION: Synthetic

<400> SEQUENCE: 69

```
Ser Asn Ile Val Ile Gly Ile Gly Asp Lys Ala Leu Lys Ile Asn Trp
  1               5                  10                  15

<210> SEQ ID NO 70
<211> LENGTH: 16
<212> TYPE: PRT
<213> ORGANISM: Artificial Sequence
<220> FEATURE:
<223> OTHER INFORMATION: Synthetic

<400> SEQUENCE: 70

Ser Tyr Ile Val Ile Gly Val Gly Asn Ser Ala Leu Thr Leu His Trp
  1               5                  10                  15

<210> SEQ ID NO 71
<211> LENGTH: 16
<212> TYPE: PRT
<213> ORGANISM: Artificial Sequence
<220> FEATURE:
<223> OTHER INFORMATION: Synthetic

<400> SEQUENCE: 71

Ser Tyr Ile Val Val Gly Arg Gly Asp Lys Gln Ile Asn His His Trp
  1               5                  10                  15

<210> SEQ ID NO 72
<211> LENGTH: 16
<212> TYPE: PRT
<213> ORGANISM: Artificial Sequence
<220> FEATURE:
<223> OTHER INFORMATION: Synthetic

<400> SEQUENCE: 72

Ser Tyr Ile Val Val Gly Arg Gly Glu Gln Gln Ile Asn His His Trp
  1               5                  10                  15

<210> SEQ ID NO 73
<211> LENGTH: 12
<212> TYPE: PRT
<213> ORGANISM: Artificial Sequence
<220> FEATURE:
<223> OTHER INFORMATION: Synthetic

<400> SEQUENCE: 73

Asn Ile Ile Tyr Val Gly Asp Leu Asn His Gln Trp
  1               5                  10

<210> SEQ ID NO 74
<211> LENGTH: 16
<212> TYPE: PRT
<213> ORGANISM: Artificial Sequence
<220> FEATURE:
<223> OTHER INFORMATION: Synthetic

<400> SEQUENCE: 74

Ser Tyr Ile Val Val Gly Arg Gly Asp Lys Gln Ile Asn His His Trp
  1               5                  10                  15

<210> SEQ ID NO 75
<211> LENGTH: 9
<212> TYPE: PRT
<213> ORGANISM: Artificial Sequence
<220> FEATURE:
<223> OTHER INFORMATION: Synthetic

<400> SEQUENCE: 75

Phe Lys Leu Glu Lys Glu Val Ala Glu
```

```
                1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Cys Thr Glu Lys Asp Ser Pro Cys
  1               5

<210> SEQ ID NO 77
<211> LENGTH: 12
<212> TYPE: PRT
<213> ORGANISM: Artificial Sequence
<220> FEATURE:
<223> OTHER INFORMATION: Synthetic

<400> SEQUENCE: 77

Asn Ile Ile Tyr Val Gly Asp Leu Ser Gln Gln Trp
  1               5                  10

<210> SEQ ID NO 78
<211> LENGTH: 16
<212> TYPE: PRT
<213> ORGANISM: Artificial Sequence
<220> FEATURE:
<223> OTHER INFORMATION: Synthetic

<400> SEQUENCE: 78

Ser Tyr Ile Val Val Gly Arg Gly Thr Thr Gln Ile Asn Tyr His Trp
  1               5                  10                  15

<210> SEQ ID NO 79
<211> LENGTH: 12
<212> TYPE: PRT
<213> ORGANISM: Artificial Sequence
<220> FEATURE:
<223> OTHER INFORMATION: Synthetic

<400> SEQUENCE: 79

Asn Ile Ile Tyr Val Gly Glu Leu Ser His Gln Trp
  1               5                  10

<210> SEQ ID NO 80
<211> LENGTH: 16
<212> TYPE: PRT
<213> ORGANISM: Artificial Sequence
<220> FEATURE:
<223> OTHER INFORMATION: Synthetic

<400> SEQUENCE: 80

Ser Tyr Ile Val Val Gly Arg Gly Glu Gln Gln Ile Asn His His Trp
  1               5                  10                  15

<210> SEQ ID NO 81
<211> LENGTH: 16
<212> TYPE: PRT
<213> ORGANISM: Homo sapiens

<400> SEQUENCE: 81

Ser Tyr Ile Ile Val Gly Arg Gly Asp Ser Arg Leu Thr Tyr Gln Trp
  1               5                  10                  15

<210> SEQ ID NO 82
```

```
<211> LENGTH: 12
<212> TYPE: PRT
<213> ORGANISM: Homo sapiens

<400> SEQUENCE: 82

Val Thr Ala Ala Pro Gln Ser Val Cys Ala Leu Arg
  1               5                  10

<210> SEQ ID NO 83
<211> LENGTH: 11
<212> TYPE: PRT
<213> ORGANISM: Homo sapiens

<400> SEQUENCE: 83

Leu Pro Pro Asn Val Val Glu Glu Ser Ala Arg
  1               5                  10

<210> SEQ ID NO 84
<211> LENGTH: 10
<212> TYPE: PRT
<213> ORGANISM: Homo sapiens

<400> SEQUENCE: 84

Val Gly Glu Tyr Ser Leu Tyr Ile Gly Arg
  1               5                  10

<210> SEQ ID NO 85
<211> LENGTH: 13
<212> TYPE: PRT
<213> ORGANISM: Homo sapiens

<400> SEQUENCE: 85

Ile Val Leu Gly Gln Glu Gln Asp Ser Tyr Gly Gly Lys
  1               5                  10

<210> SEQ ID NO 86
<211> LENGTH: 11
<212> TYPE: PRT
<213> ORGANISM: Homo sapiens

<400> SEQUENCE: 86

Leu Ile Cys Gln Ala Thr Gly Phe Ser Pro Arg
  1               5                  10

<210> SEQ ID NO 87
<211> LENGTH: 20
<212> TYPE: PRT
<213> ORGANISM: Homo sapiens

<400> SEQUENCE: 87

Leu Thr Cys Leu Val Thr Asp Leu Thr Thr Tyr Asp Ser Val Thr Ile
  1               5                  10                  15

Ser Trp Thr Arg
             20

<210> SEQ ID NO 88
<211> LENGTH: 17
<212> TYPE: PRT
<213> ORGANISM: Homo sapiens

<400> SEQUENCE: 88

Val Phe Asp Glu Phe Lys Pro Leu Val Glu Glu Pro Gln Asn Leu Ile
  1               5                  10                  15

Lys
```

```
<210> SEQ ID NO 89
<211> LENGTH: 13
<212> TYPE: PRT
<213> ORGANISM: Homo sapiens

<400> SEQUENCE: 89

Gln Asn Cys Glu Leu Phe Glu Gln Leu Gly Glu Tyr Lys
 1               5                  10

<210> SEQ ID NO 90
<211> LENGTH: 14
<212> TYPE: PRT
<213> ORGANISM: Homo sapiens

<400> SEQUENCE: 90

Asp Ser Thr Tyr Ser Leu Ser Ser Thr Leu Thr Leu Ser Lys
 1               5                  10

<210> SEQ ID NO 91
<211> LENGTH: 27
<212> TYPE: PRT
<213> ORGANISM: Artificial Sequence
<220> FEATURE:
<223> OTHER INFORMATION: Synthetic

<400> SEQUENCE: 91

Lys Gly Met Ser Tyr Ser Met Cys Thr Gly Lys Phe Lys Asn Gly Gln
 1               5                  10                  15

Tyr Glu Gly Asp Gly Ser Pro Cys Lys Ile Pro
            20                  25
```